US008415118B2

(12) United States Patent
Huang et al.

(10) Patent No.: US 8,415,118 B2
(45) Date of Patent: Apr. 9, 2013

(54) PORCINE DC-SIGN, ICAM-3 AND LSECTIN AND USES THEREOF

(75) Inventors: Yaowei Huang, Blacksburg, VA (US); Xiang-Jin Meng, Blacksburg, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 0 days.

(21) Appl. No.: 12/739,744

(22) PCT Filed: Oct. 29, 2008

(86) PCT No.: PCT/US2008/012251
§ 371 (c)(1),
(2), (4) Date: Apr. 25, 2010

(87) PCT Pub. No.: WO2009/058285
PCT Pub. Date: May 7, 2009

(65) Prior Publication Data
US 2010/0317054 A1      Dec. 16, 2010

Related U.S. Application Data

(60) Provisional application No. 61/000,800, filed on Oct. 29, 2007.

(51) Int. Cl.
*C12P 21/06* (2006.01)
*C12N 15/00* (2006.01)
*C12N 1/20* (2006.01)
*C07H 21/02* (2006.01)

(52) U.S. Cl. .................. 435/69.1; 435/320.1; 435/252.3; 435/6.1; 536/23.1

(58) Field of Classification Search ............ 435/6.1, 435/69.1, 252.3, 320.1; 536/23.2
See application file for complete search history.

(56) References Cited

FOREIGN PATENT DOCUMENTS

| WO | 2005/014040 A2 | 2/2005 |
|---|---|---|
| WO | 2005/014040 A3 | 2/2005 |
| WO | 2005/113003 A2 | 12/2005 |
| WO | 2005/113003 A3 | 12/2005 |

OTHER PUBLICATIONS

Database EMBL, Oct. 14, 2004, "Sus scrofa mRNA, clone: MLN01F030001, 5' end, expressed in mesenteric lymph node," Accession No. CJ007777.
Geijtenbeek, Teunis, et al., "Identification of DC-SIGN, a Novel Dendritic Cell-Specific ICAM-3 Receptor that Supports Primary Immune Responses," Cell, vol. 100, No. 5, pp. 575-585, Mar. 3, 2000.
Database Genbank, Sep. 26, 2007, "*Homo sapiens* CD209 molecule (CD209)," Accession No. NM_021155.
Database EMBL, Sep. 16, 2006, "Sus scrofa mRNA, clone: THY010118Al2, expressed in thymus," Accession No. AK239636.
Database EMBL, Sep. 16, 2006, "Sus scrofa mRNA, clone: LVRM10084C09, expressed in liver," Accession No. AK233123.
Fawcett, Jonathan, et al., "Molecular cloning of ICAM-3, a third ligand for LFA-1, constitutively expressed on resting leukocytes," Nature, vol. 360, No. 6403, pp. 481-484, Dec. 3, 1992.
Database EMBL, Sep. 17, 2007, "intercellular adhesion molecule 3 precursor [*Homo sapiens*]," Accession No. NP_002153.
Database EMBL, Sep. 16, 2006, "Sus scrofa mRNA, clone: LVR010098C02, expressed in liver," Accession No. AK232603.
Liu, Wanli, et al., "Characterization of a Novel C-type Lectin-like Gene, LSECtin—Demonstration of carbohydrate binding and expression in sinusoidal endothelial cells of liver and lymph node," Journal of Biological Chemistry, vol. 279, No. 18, pp. 18748-18758, Apr. 30, 2004.
Dominguez-Soto, Angeles, et al., "The DC-SIGN-related lectin LSECtin mediates antigen capture and pathogen binding by human myeloid cells," Blood, vol. 109, No. 12, pp. 5337-5345, Jun. 15, 2007.
Database EMBL, Sep. 26, 2007, "C-type lectin superfamily 4, member G [*Homo sapiens*]," Accession No. NP_940894.
Halary, Franck, et al., "Human Cytomegalovirus Binding to DC-SIGN Is Required for Dendritic Cell Infection and Target Cell *trans*-Infection," Immunity, vol. 17, pp. 653-664, Nov. 1, 2002.
Tassaneetrithep, Boonrat, et al., "DC-SIGN (CD209) Mediates Dengue Virus Infection of Human Dendritic Cells," Journal of Experimental Medicine, vol. 197, No. 7, pp. 823-829, Apr. 7, 2003.

*Primary Examiner* — Maryam Monshipouri
(74) *Attorney, Agent, or Firm* — Michael J. Moran; Gloria K. Szakiel; Anne M. Rosenblum

(57) ABSTRACT

The present invention relates to the cloning, identification and characterization of the unique and entire genomic sequences encoding new porcine DC-SIGN and LSECtin proteins, including the novel nucleotide sequences of the full-length cDNA and genes of both pDC-SIGN gene and pLSECtin. Also provided are the nucleic acid molecules encoding newly discovered porcine ICAM-3 isoforms from porcine monocyte-derived dendritic cells and the use thereof. Specifically, the invention is drawn to an isolated nucleic acid molecule comprising a nucleotide sequence encoding one or more of porcine DC-SIGN, porcine ICAM-3, porcine LSECtin, a complement of the nucleotide sequence or a functional, defined portion of the nucleotide sequence or a protein fusion product linked to a protein that may be of porcine or human origin. Methods for isolating and cloning the new porcine genes and for using the new nucleotide sequences in improved methods for propagating viruses, particularly enveloped viruses, are additionally described herein. The invention further includes new transfected cells or cell lines that can stably express the porcine proteins, new antibodies and the like.

31 Claims, 36 Drawing Sheets

```
GGAGAGGAACAGAGAGAGGATGGCAGAGATATGTGACCCCAAGGAGGAGAAGACATGGACGGGGCCCAGTATTGGTGAGCGAGATCTT    100
                        M  A  E  I  C  D  P  K  E  E  K  T  W  T  G  P  V  L  V  E  R  D  L    25

GGACTACTGCGCAGATTAAGGAACTCACCAGGGTGTCTGAGACTTGGCCCTCCTCTGCTGCTCTTCGTTTCTTCATGCTCCTCGTGA    200
 G  L  L  R  R  L  R  N  S  P  G  C  L  T  W  P  L  L  L  L  L  F  V  S  L  G  F  F  M  L  L  V    58

CCACCCTGGTTCAAGTTTCCAGGATCCACCAGTCTCTGCAGAGAGAGACCCAGCCCACAGCCCAGGAGAAGATACAATCAAGCCTGGA    300
 T  T  L  V  Q  V  S  R  I  H  Q  S  L  Q  R  E  R  E  T  S  R  R  P  T  A  Q  E  K  I  Q  S  S  L  D    92

TAAGTTCCTGCAGCAGATGACCTGGATGAATGCCACCCTGGCCGGCCTGTGCCATCCCTGCCCCTGGCATTGGGAATTCTTCCAGGGAAGATGCTACTTA    400
                K  F  L  Q  Q  M  T  W  M  N  A  T  L  A  G  L  C  H  P  C  P  W  H  W  E  F  F  Q  G  R  C  Y  L    125

TTCTCCCAGACCCAGAGTGTCCAGCTGACTGGAAATCCTCTCTCTCCGGCCTGTAAGGACATTGGGGCCCAGCTGGTTATCATCAATAGCACTGCCGAGCAGAAATTCC    500
 F  S  Q  T  Q  S  D  W  K  S  S  L  S  A  C  K  D  I  G  A  Q  L  V  I  I  N  S  T  A  E  Q  K  F    158

TGAAGTCTTGGTATGTCAGATATAATAAAGCCACCTGGATTGGCCTCAGTGATGACACCAATGAAGGTTCCTGGCAATGGGTGGAACACAGCCCCCTCCA    600

FIG. 2a
```

```
L K S W Y V R Y N K A T W I G L S D D T N E G S W Q W V D N S P L Q      192
      ↓
ACTCAGCTTCTGGAAAGAAGGAGAACCCAACAATCACGGAGATGAAGACTGTGCAGAATTGCACAACGATGGCTGGAATGATAGCAAATGTACGGTAGAA      700
 L S F W K E G E P N N H G D E D C A E L H N D G W N D S K C T V E
AAGGCCTGGATCTGTGAGAAGCCCTCGTCTCCCGCCCAGCTGCCCACTGCCCAGCCTCTACTCCCATCAGCAGAGAATAGGCAACAGGCC             800
 N A W I C E K P S S P C P M L *                                         240
CTCAGCTGGTTCCCTTGGCTCCACCCTCTTCCATCTTTACCCTTGGTGAATTCCCATCCCTTCTTGAACGACGGTCTCTTTTAGATCCTACGAGAGAT    900
TCTGAAACCCCCTTATCCTCGAACCCTCTCCTTCCATAGGCTACAAACCCTCTCTTCATCTGAGATGGTCTCAGCAGCCCTCCGCCCCGGCCCCCCCC    1000
ATGACATCCCCTT AATAAA GTCACATTGCATTATGTGTTCCAAAAAAAAAAAAAAAAAAAAA                                      1069
```

FIG. 2b

5' GATGGCAGAGATATGTGACCCCAAGGAGCCAGGTAGCCCCAGTGAGGGTGACCCCATTCTGGGAGTGATGATGGGGGAGGACAGGGCT  90
    ━━━ Exon 1 ━━━■
          ━━1F━━▶

5' CCTGGGTCCTGAGGGCACCGCAGGGGCGGGCCTAGCATCCCAGCTTGCAATCCTGCAGAGCAGGCCCAGCAGTCTTCCAAGTTCAAATGAATAT  180

5' GCTCTGTCCTATTCAGAGGAGAAGACATGGACGGGCCAGTATTGGTTGAGCAGCCAGATCTTGGACTACTGCGCAGATTAAGGAACTCACCA  270
                                                          ━━━━━━ Exon 2 ━━━━━━■

5' GGTACTAGGGTGGCTGGTTCAGGAGTAGGCCACTGGGGAAGGGGTGGTAGGGGGTAGGGTGGGGCAGGGTCTGCCTCTGAGCCCCTAGC  360

5' GCTGCCCATCTGCTGGTCCTGCAGGGTCTCTGACTTGGCCCCTCCTTCTGCTGCTCCTCGTCTCATTGGGTTTCTTCATGCTCCTGG  450
    ━━━━━━ Exon 3 ━━━━━━
   ■

5' TGACCACCCTGGTTCAAGGTGAGTCAGGGTTGGGGGCTTCGAGTCCTGGGTCCCGTTGGGTTTTCTCTCTGGGATGGTTTTTGACCTTT  540
   ━━ Exon 3 ━━■                                                             ◀━━2F━━

5' TCCCTAGTCCTGAAACCTACTGGGGCTGGGCATTTGGACTCTGTGTTGCCCCTCTGTGTGACTGGGGCCAGTTACTCCCTTCTCTGG  630

5' ACCTGTTTCCTTATGTGAAATGTAGCTCATCCTCCCCTGTGGGGAGCTTAGCCTGCACTTGAAATGAACTTGGCAGTTCCCGTTGTGGC  720

5' ACAGTGGTTAACGAATCCGACTAGGAACCATGAGGTTTCGGGTTCGGTCCCTGCCTTGCCTCAGTGGGTTAACGATCCCGCGTTGCTGTG  810

5' AGCTGGTGGTGTAGATTGCAGATGCGGGCTGGGATCCCGCGTTGCTGTGGGTCTGGGCATAGGCCAGTGGCTACAGCTCCACCCCTA  900

5' ACCTGGGAACCTCCATATGCCACCGGAGCGGCCCAAAGAAATAGTAAAAAGACAAAAAAAAAAAAAAAAAGAAAAAGAAAATGAAC  990

FIG. 5a

5' TCCTGTTGGGGCTGGGTCATAGGGCTGGTCAACAAAGAGCCTTCTGCCACCCTCCTCTGCCCCCTGAGAGATGGAGGTCCAGTGGATAGC 1980

5' TGGAGATGGGAGGGTAATGCAGTCAGGGAAGGCTTCCTGGAGGAGGAACCATAACGGACTCAGGAAGGTCACATGAGAGAAGAACCAGGA 2070

5' TGGGAGGAGCCCATATATGGATAGAAAAGGAACTCAAGAATGCCCTCGAAGAGTTCCCGTCCTGGCTCAGCAGTGAACTAATCTGACTCT 2160

5' CATCCATGAGGATGCAGGTTCGATTCCTGCCTTGCTCTGTGGGTTAAGGATCCGACATTGCTGTGGTATAGGACAGCAGCTACAGCTCT 2250

5' GATTCAGTCCCTAGCCCTGGGAACCTCTATATGTGGCTGGTCCTAAGAAGCAAGAAAAAAAGAATGCCCTTGGAACCATCCATAACGTAG 2340

5' GGTCAACTGGAGATACAAGTTAACATATCCACACATGTATGGGTACGAATACACATTCACAGCCTACTTGCACATGTGAACATACACAAC 2430

5' TTGAGTAGAGGCTATGGACTAGACTGCAGAAGGAACTTTTGTGAGAGGCAGGGGACAGAGGGAACGTGGAAGACATGTGACAGATGTCA 2520

5' TTGAGGGAATCTTCCCCACCCCAGAAATTCCTGAAGTCTTGGTATGTCAGATATAATAAAGCCACCTGGAT 2610
                                                                    ─── Exon 7 ───

5' TGGCCTCAGTGATGACACCAATGAAGGTTCCTGGCAATGGGTGACAACAGCCCCCTCCAACTCAGTGACCTCCCAGTGACAATGGCCC 2700
   ─── Exon 7 ───

5' AGGAAGGGGTGGGCAGGGAAAAAACCACCTTTCCCAAACCAGGGTGCTCAGATTCTGGGACTGAAAAGTACCACCTGAAGAGCTTGGT 2790

5' GAACGATGCAGCGTCCCCGGCTCCACGGCTGCTGTTGGGGGACGGGGAGGGGGGCTCGAGTCAGTACCGGGCCCCAGGAACCTGCATTTTTACTTT 2880

5' GCCAGAGCTGATTCTGATGGAGGTGGTATTTGAGCCCACATTTTGAAACCACCCTCTGGCTACCTGGCAATCAACTGCCACAGC 2970

5' CTAGGGACAGCTTCTCCAAGGGGGGGTGGGGTGGAGGGGTTCTGGGTAGAGTAGGGGTCCAGAGCTCTGATGGGGTTCACAGCTT 3060

FIG. 5c

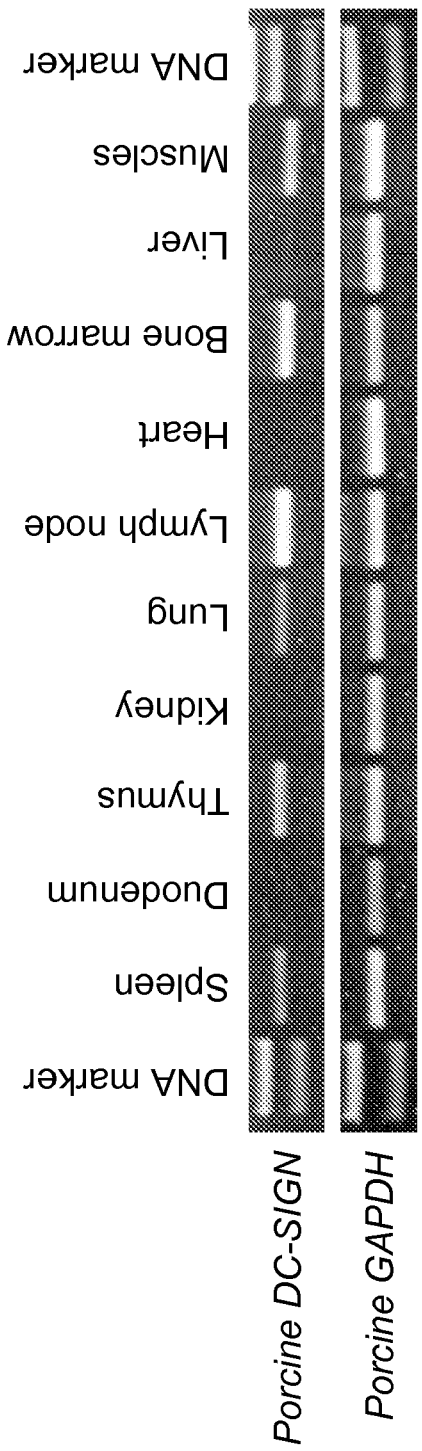

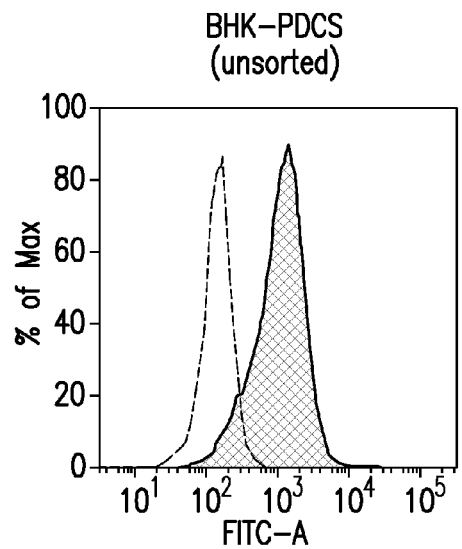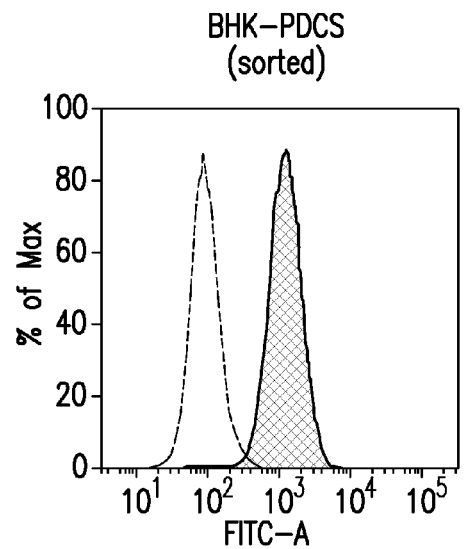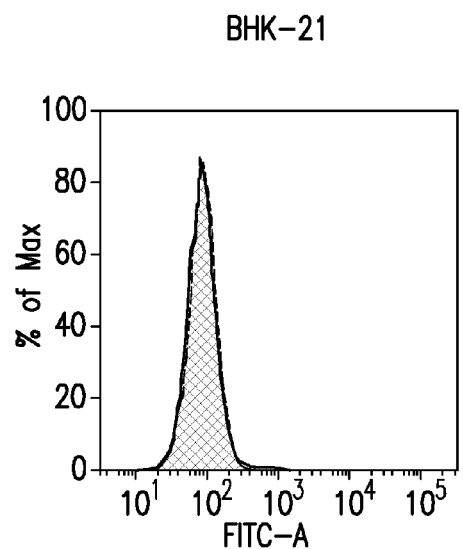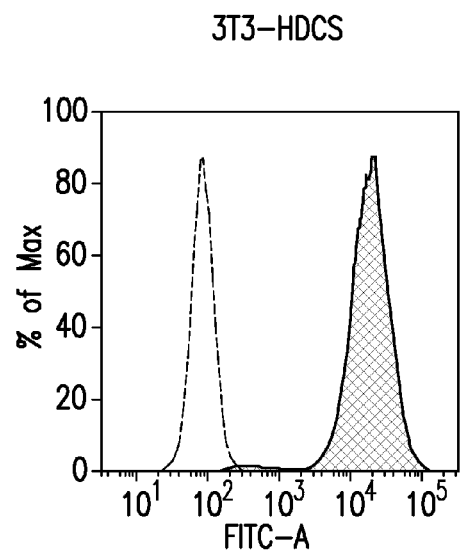
FIG.8a

FIG. 11b

```
                                                                                                              Exon 1 ↓ Exon 2
tttatatctatgcccagagcaggcacctgcttaccatggacactgccggtaccagcaggtgggaggtccctgaggcactgggacactgggg                                                    110

M  D  T  A  G  Y  S  K  W  D  H  K  L  E  E  V  P  G  G  H  W  G  H  W  G                                                    34
                                              Exon 2 ↓ Exon 3
acagagatccctcctcctgcttggtctgtggtcgtcacagtctcgtgggccctcgttctgagcatcctattttccaaggcctccacagagccggggcgctgttg                                     220

Q  R  S  L  L  L  A  F  G  L  V  V  V  T  V  L  W  A  L  V  L  S  I  L  F  S  K  A  S  T  E  R  G  A  L  L                                    70
                       Exon 3 ↓ Exon 4                                        Exon 4 ↓ Exon 5
gccaccaggatctactgaggagcaaacgctcgaagcggagactctgaaggtcttgaaggaggagtccgagcctgcaacactgctgcctggggtgcaggcgcag                                      330

G  H  D  D  L  L  R  T  N  A  S  K  D  T  A  T  L  K  V  L  K  E  E  V  R  A  C  N  S  C  C  L  G  V  D  A  Q                                 107
                                                                              Exon 5 ↓ Exon 6
ctgcagacgtgcacaccagctggagaggcaaaggcaagctgttggagcaggagagccctgaggaactgagcgagcgtgaccagggcgtgaccggactggctgaagcgg                                 440

L  Q  T  V  H  T  Q  L  G  E  A  K  L  L  E  Q  E  S  A  L  K  E  L  S  E  R  V  T  Q  G  L  A  E  A  G                                       144
                                    Exon 6 ↓ Exon 7
tagggaccgtgagaacatccgcagtgagctcttccgggactgaaagaagtccgttccagaacagctcctgcgagcagtgcccaagtgctgcattccagggct                                       550

R  D  R  E  H  I  R  S  E  L  F  R  E  L  E  R  V  R  F  Q  H  S  S  C  E  Q  C  P  K  S  W  L  P  F  Q  G                                    180
                                                                              Exon 7 ↓ Exon 8
cttgttacttttctcggcgcaaggggccacgtggggctcaggcgctcagggccactgcgggggcgcacctggtgattgttgggggcctgaaggagcagggcttc                                     660

S  C  Y  F  F  S  A  Q  G  A  T  W  V  E  A  Q  S  H  C  E  G  A  G  A  H  L  V  I  V  G  G  L  E  E  Q  G  F                                 217
                                                                                                      Exon 8 ↓
ctggtcggaatactgccagccggctactgctgggctgaggctgccgaggctgtgccagggcgcgcaaatccagagctaccagtggtggatggagtcccactcagcttcag                                770
```

Exon 9
ccactgaatctgggggaaccccatgactctctggggcgcgaggactgcatcatgatgctacggacgggggatgtggaatgacgaccgtgcaacagcaaagacgacagct 880

H W N L G E P N D S L G R E D C I M M L R T G M W N D A P C N S K D D S 290 ggatctgcgagaagaggcacaaactgct gacctagccagcccagtgcccagagccaagccactgccacttgtccaatcgcctgagctgcttactgcctgctccgccacca 990

W I C E K R H N C 299 ctataatccctcccactgcttccagcaaaaacaccccttcacccagagccaataactgagctcagctccaaccccgctgcatccctcaccccatgagcctaa 1100
tgtatctacattgctccaaaatctgagctcctctgcctgatctggccccataccctaaccaggtcagtcacctcagggatggagctgtttggtttgcttg 1210
cttttaccccagaaggggggcctcaaagatagagattttgtggcttttcttcacagacccctagggagcatcAATAAAtgagaaatgaatcttaaaaaaaaaaaaaaa 1320
aaaaaa 1327

FIG. 14c

PORCINE DC-SIGN, ICAM-3 AND LSECTIN AND USES THEREOF

CROSS-REFERENCE TO RELATED APPLICATIONS

This application commences the national stage under 35 U.S.C. §371 of PCT International Application No. PCT/US2008/012251, filed on Oct. 29, 2008, which claims the priority benefit of U.S. Provisional Application No. 61/000,800, filed on Oct. 29, 2007, now abandoned. The prior application is incorporated herein by reference in its entirety.

STATEMENT REGARDING FEDERALLY SPONSORED RESEARCH OR DEVELOPMENT

Not Applicable

NAMES OF PARTIES TO A JOINT RESEARCH AGREEMENT

Not Applicable

BACKGROUND OF THE INVENTION

1. Field of the Invention

The present invention concerns novel porcine DC-SIGN and porcine LSECtin genes, cDNA derived from the respective porcine monocyte-derived dendritic and liver cells, porcine DC-SIGN and porcine LSECtin proteins, transfected cells or cell lines stably expressing the new proteins, fusion products, antibodies, methods for isolating and cloning the porcine genes and the use of the porcine proteins for propagating viruses. Also provided is the nucleotide sequence encoding newly discovered porcine ICAM-3 isoforms from porcine monocyte-derived dendritic cells.

2. Description of Related Art

All patents and publications cited in this specification are hereby incorporated by reference in their entirety.

Dendritic cells (DCs) are professional antigen-presenting cells (APCs) located throughout the peripheral immune system. Invading foreign antigens trigger the migration of immature DCs from the blood into tissues where they detect and capture the antigens (K. Palucka and J. Banchereau, "Dendritic cells: a link between innate and adaptive immunity," J. Clin. Immunol. 19:12-25 (1999)). Activated DCs process captured proteins into immunogenic peptides through MHC molecules (a set of membrane glycoproteins called the MHC molecules or the Major Histocompatibility Complex) and present to T cells. Recognition of invading pathogens by DCs is mediated by pattern-recognition receptors (PRRs) including Toll-like receptors (TLRs) and lectins (S. Thoma-Uszynski et al., "Induction of direct antimicrobial activity through mammalian toll-like receptors," Science 291:1544-1547 (2001); W. I. Weis et al., "The C-type lectin superfamily in the immune system," Immunol. Rev. 163:19-34 (1998)). The lectins expressed on the surface of DCs are members of the calcium-dependent C-type lectin receptor (CLRs) family and play a key role in the antigen capture and internalization of DCs (Weis et al., 1998, supra). CLRs are also expressed on other APCs including macrophages.

The CLR family includes a large number of proteins that perform protein-carbohydrate interactions by binding to the polysaccharide chains on glycoprotein ligands in a calcium-dependent manner. Numerous CLRs belong to PRRs expressed on the surface of APCs that recognize foreign pathogens, playing a key role in host immune responses. The type II CLRs are classified by their $NH_2$ terminus domain, cytoplasmic tail (CT), located in the cytoplasm of the cell. Other type II CLR domains include the transmembrane domain (TMD) following the CT, a single carbohydrate recognition domain (CRD) at the carboxyl terminus exposed extracellularly and the neck domain between the TMD and CRD.

A human lectin gene cluster of type II CLRs, CD23/LSECtin/DC-SIGN/L-SIGN, which is localized at human chromosome 19p13.3, has received increasing interest. Human DC-SIGN, hL-SIGN and hLSECtin, which have analogous genomic structures (W. Liu et al., "Characterization of a novel C-type lectin-like gene, LSECtin: demonstration of carbohydrate binding and expression in sinusoidal endothelial cells of liver and lymph node," J. Biol. Chem. 279:18748-58 (2004)), are important C-type lectins capable of mediating pathogen recognition. Human CD23 (FCER2) is a low affinity IgE receptor that plays an important role in cell-cell adhesions, B cells survival and antigen presentation. Dendritic cells-specific intercellular-adhesion-molecule-3 ("ICAM-3")-grabbing nonintegrin (human CD209, also known as "DC-SIGN," a 44 kDa type II transmembrane protein), a CLR, was identified as an ICAM-3 binding protein mediating DCs and T cell interaction (T. B. Geijtenbeek et al., "Identification of DC-SIGN, a novel dendritic cell-specific ICAM-3 receptor that supports primary immune responses," Cell 100:575-585 (2000)) and a HIV-1 gp120 receptor mediating transmission of HIV-1 to susceptible cells in trans (T. B. Geijtenbeek et al, "DC-SIGN, a dendritic cell-specific HIV-1-binding protein that enhances trans-infection of T cells," Cell 100:587-597 (2000)). Additionally, DC-SIGN was found to interact with ICAM-2 binding protein, regulating chemokine-induced trafficking of DCs across both resting and activated endothelium (T. B. Geijtenbeek et al., "DC-SIGN-ICAM-2 interaction mediates dendritic cell trafficking," Nat. Immunol. 1:353-357 (2000)). A second human DC-SIGN (hDC-SIGN) homologue, hL-SIGN (CD209L) or DC-SIGNR, was subsequently identified and shown to have similar function, but subtly distinct property of pathogen recognition, to hDC-SIGN (A. A. Bashirova et al., "A dendritic cell-specific intercellular adhesion molecule 3-grabbing nonintegrin (DC-SIGN)-related protein is highly expressed on human liver sinusoidal endothelial cells and promotes HIV-1 infection," J. Exp. Med. 193:671-678 (2001)).

Human DC-SIGN is expressed mainly on monocyte-derived human DCs in vitro, on immature and mature DCs in the normal human lymph node, dermis, mucosa and spleen and on macrophages in alveoli of the lung in vivo (T. B. Geijtenbeek et al., "Identification of DC-SIGN, a novel dendritic cell-specific ICAM-3 receptor that supports primary immune responses," Cell 100:575-585 (2000); T. B. Geijtenbeek et al., "DC-SIGN, a dendritic cell-specific HIV-1-binding protein that enhances trans-infection of T cells," Cell 100:587-597 (2000); L. Tailleux et al., "DC-SIGN induction in alveolar macrophages defines privileged target host cells for mycobacteria in patients with tuberculosis," PLoS Med. 2:e381 (2005); E. J. Soilleux et al., "Constitutive and induced expression of DC-SIGN on dendritic cell and macrophage subpopulations in situ and in vitro," J. Leukoc. Biol. 71:445-457 (2002)), whereas L-SIGN is highly expressed in sinusoidal endothelial cells of the liver and lymph node (Bashirova et al., 2001, supra). It has been observed that L-SIGN homologues only exist in human and non-human primates but not in other non-primates mammalian species.

Recently, a third human DC-SIGN-related C-type lectin (identified as "CLEC4G" and named "LSECtin"), which is co-expressed with hL-SIGN on liver and lymph node sinusoidal endothelial cells (LSECs), was identified with similar property of pathogen recognition and antigen capture (A. Dominguez-Soto et al., "The DC-SIGN-related lectin LSECtin mediates antigen capture and pathogen binding by human myeloid cells," Blood 109:5337-45 (2007)). Besides hLSECtin, LSECtin homologues in other mammalian species have not been experimentally identified although limited gene information can be searched from the genome databases.

Due to similarities in organ size and physiology with humans, pig is considered to be the preferred source animal for xenotransplantation (Y. G. Yang and M. Sykes, "Xenotransplantation: current status and a perspective on the future," Nat. Rev. Immunol. 7:519-31 (2007)). Understanding the compatibilities across the human-pig species barrier of the molecular interactions is very critical for the clinical application of pig-to-human xenotransplantation. Interactions of the receptors on porcine hematopoietic cells with ligands on human endothelial cells play a crucial role in the event that porcine hematopoietic cells are used to induce tolerance in the human recipient (A. N. Warrens et al., "Human-porcine receptor-ligand compatibility within the immune system: relevance for xenotransplantation," Xenotransplantation 6:75-8 (1999)). T-cell-mediated xenograft rejection, a phenomenon probably caused by induction of stronger human T cell responses against pig antigen than that against alloantigens, also involved potential interactions of adhesion molecules between porcine APCs such as DCs and human T cells (A. Dorling et al., "Detection of primary direct and indirect human anti-porcine T cell responses using a porcine dendritic cell population," Eur. J. Immunol. 26:1378-87 (1996)). DC-SIGN has been further shown as the endogenous adhesion receptor for ICAM-2 and ICAM-3 (T. B. Geijtenbeek et al., "Identification of DC-SIGN, a novel dendritic cell-specific ICAM-3 receptor that supports primary immune responses," Cell 100:575-585 (2000)); T. B. Geijtenbeek et al., "DC-SIGN-ICAM-2 interaction mediates dendritic cell trafficking," Nat. Immunol. 1:353-357 (2000); D. A. Bleijs et al., "DC-SIGN and LFA-1: a battle for ligand," Trends Immunol. 22:457-63 (2001)).

Porcine reproductive and respiratory syndrome virus (PRRSV), an economically important swine pathogen worldwide, is a member of the family *Arteriviridae* in the order of the *Nidovirales*. PRRSV isolates identified thus far worldwide are divided into two distinct genotypes, European (type 1) and North American (type 2) genotypes, which cause the same disease symptoms but are antigenically different. Like other enveloped viruses such as HIV and HCV, the entry of PRRSV into the host cells, namely, the porcine alveolar macrophages, is a complex multistep process that involves the presence of several entry factors including sialoadhesin, CD163 and heparan sulphate (P. L. Delputte et al., "Analysis of porcine reproductive and respiratory syndrome virus attachment and internalization: distinctive roles for heparan sulphate and sialoadhesin," J. Gen. Virol. 86:1441-5 (2005)). However, the potential interaction between PRRSV and porcine PRRs on APCs has not yet been reported. Since human L-SIGN was shown to be associated with SARS-coronavirus entry in lung, the porcine DC-SIGN/L-SIGN homologue may play a similar role during PRRSV infection in pig lung since PRRSV and coronavirus both belong to the Nidovirales order but significant experimentation is warranted before a conclusion can be drawn.

Although the monkey kidney cell line (as described in U.S. Pat. No. 6,146,873 and elsewhere) and primary porcine alveolar macrophages (PAMs) have been the only two cells known to support productive PRRSV replication, other cells such as the BHK-21 cell line have been shown to be replication-competent, that is, having the necessary ability to support PRRSV replication (H. Nielsen et al., "Generation of an infectious clone of VR-2332, a highly virulent North American-type isolate of porcine reproductive and respiratory syndrome virus," J. Virol. 77:3702-11 (2003); J. J. Meulenberg et al., "Infectious transcripts from cloned genome-length cDNA of porcine reproductive and respiratory syndrome virus," J. Virol. 72:380-7 (1998)). For example, when BHK cells were transfected with viral RNA or in vitro synthesized RNA transcripts from full-length genomic cDNA of European strain LV or North American strain VR-2332, evidence of PRRSV replication was detected in BHK cells. PRRSV virions were produced and excreted into the medium; and when the supernatant from transfected BHK-21 cells was transferred to PRRSV-permissive cells, cythopathic effects (CPE) was observed. Unfortunately, the replicating virus in transfected BHK-21 cells does not spread from cell-to-cell, indicating the lack of receptors on BHK-21 cells. A putative PRRSV binding receptor was reportedly identified from alveolar macrophages to be 210-kDa membrane protein (E. H. Wissink et al., "Identification of porcine alveolar macrophage glycoproteins involved in infection of porcine respiratory and reproductive syndrome virus," Arch. Virol. 148:177-87 (2003)) but functional confirmation of this receptor candidate at the level of virus entry is still lacking Recently, it has been shown that porcine sialoadhesin (pSn) mediates internalization of PRRSV in PAMs (N. Vanderheijden et al., "Involvement of sialoadhesin in entry of porcine reproductive and respiratory syndrome virus into porcine alveolar macrophages," J. Virol. 77(15):8207-15 (2003)), and that pSn is a sialic acid binding lectin and interactions between sialic acid on the PRRS virion and pSn are essential for PRRSV infection of PAMs (P. L. Delputte and H. J. Nauwynck, "Porcine arterivirus infection of alveolar macrophages is mediated by sialic acid on the virus," J. Virol. 78(15):8094-101 (2004)). In human, mice and swine, sialoadhesin is only expressed on discrete subsets of tissue macrophages. PRRSV is known to infect macrophages in the respiratory and lymphoid systems of the pig in vivo. Since PRRSV also infects other monocyte-derived lymphocytes in vivo such as dendritic cells and since the structure of PRRSV virion is very complex, it is likely that multiple alternative receptors and/or co-receptors exist on these cells. In addition, PPRSV receptor on the susceptible monkey kidney cells has not yet been identified.

Macrophages and dendritic cells are important for recognition of pathogens and play important roles in immunity against invading pathogens. Human DC-SIGN and the related liver endothelial cell lectin L-SIGN have been characterized and found to express abundantly on the surface of dendritic-like cells (A. Puig-Kroger et al., "Regulated expression of the pathogen receptor dendritic cell-specific intercellular adhesion molecule 3 (ICAM-3)-grabbing nonintegrin in THP-1 human leukemic cells, monocytes, and macrophages," J. Biol. Chem. 279(24):25680-8 (2004)). Furthermore, the C-type mannose binding lectins hDC-SIGN and hL-SIGN (or DC-SIGNR) have generated considerable interest for their ability to bind and uptake pathogens including enveloped viruses such as HIV, bacteria (*Mycobacterium*), fungi and parasites in vitro (Y. van Kooyk and T. B. Geijtenbeek, "DC-SIGN: escape mechanism for pathogens," Nat. Rev. Immunol. 3:697-709 (2003)), Dengue virus (E. Navarro-Sanchez et al., "Dendritic-cell-specific ICAM3-grabbing non-integrin is essential for the productive infection of human dendritic cells by mosquito-cell-derived dengue viruses," EMBO Rep. 4(7): 723-8 (2003)), Ebola virus (C. P. Alvarez et al., "C-type lectins DC-SIGN and L-SIGN mediate cellular entry by Ebola virus in cis and in trans," J. Virol. 76(13):6841-4

(2002)), Marburg virus (A. Marzi et al., "DC-SIGN and DC-SIGNR interact with the glycoprotein of Marburg virus and the S protein of severe acute respiratory syndrome coronavirus," J. Virol. 78(21):12090-5 (2004)), SARS-coronavirus (id.), cytomegalovirus (F. Halary et al., "Human cytomegalovirus binding to DC-SIGN is required for dendritic cell infection and target cell trans-infection," Immunity 17(5): 653-64 (2002)), and hepatitis C virus (P. Y. Lozach et al., "C-type lectins L-SIGN and DC-SIGN capture and transmit infectious hepatitis C virus pseudotype particles," J. Biol. Chem. 279(31):32035-45 (2004); E. G. Cormier et al., "L-SIGN (CD209L) and DC-SIGN (CD209) mediate transinfection of liver cells by hepatitis C virus," Proc. Natl. Acad. Sci. USA 101:14067-72 (2004)) to facilitate entry into cells and infection. Both hDC-SIGN and hL-SIGN contain C-type-lectin-specific carbohydrate recognition domains (CRD) that tightly bind to asparagines-linked high mannose glycans in viral enveloped glycoproteins on a broad spectrum of enveloped viruses in a calcium ($Ca^{2}$)-dependent manner (T.B. Geijtenbeek et al., "Identification of different binding sites in the dendritic cell-specific receptor DC-SIGN for intercellular adhesion molecule 3 and HIV-1," J. Biol. Chem. 277:11314-11320 (2002)). The C-type lectins therefore concentrate viruses on cells expressing DC-SIGN or L-SIGN, and facilitate binding and entry of viruses into cells.

It has been reported that DC-SIGN binds to HIV gp120 and facilitate HIV transmission to T cells (J. F. Arrighi et al., "DC-SIGN-mediated infectious synapse formation enhances X4 HIV-1 transmission from dendritic cells to T cells," J Exp Med. 200(10):1279-88 (2004); T. B. Geijtenbeek et al., "Rhesus macaque and chimpanzee DC-SIGN act as HIV/SIV gp120 trans-receptors, similar to human DC-SIGN," Immunol Lett. 79:101-7 (2001); M. Satomi et al., "Transmission of macrophage-tropic HIV-1 by breast-milk macrophages via DC-SIGN," J. Infect. Dis. 191(2):174-81 (2005); E. J. Soilleux et al., "Placental expression of DC-SIGN may mediate intrauterine vertical transmission of HIV," J. Pathol. 195: 586-592 (2001)). DC-SIGN and L-SIGN have been shown to be high affinity binding rectors for hepatitis C virus glycoprotein E2 (P. Y. Lozach et al., "DC-SIGN and L-SIGN are high affinity binding receptors for hepatitis C virus glycoprotein E2," J. Biol. Chem. 278(22):20358-66 (2003)), and mediate transinfection of liver cells by hepatitis C virus (Lozach et al., 2004, supra; Cormier et al., 2004, supra). DC-SIGN has also been found to mediate Dengue virus infection of human dendritic cells (Navarro-Sanchez et al., 2003, supra). Both DC-SIGN and L-SIGN have been shown to mediate cellular entry by Ebola virus in cis and in trans (Alvarez et al., 2002, supra; G. Simmons et al., "DC-SIGN and DC-SIGNR bind Ebola glycoproteins and enhance infection of macrophages and endothelial cells," Virology 305(1):115-23 (2003)). In other reports, a broad spectrum of enveloped viruses including *Retroviridae* (human immunodeficiency virus (HIV), simian immunodeficiency virus (SIV) and feline immunodeficiency virus (FIV)), *Flaviviridae* (Dengue virus, West Nile virus and hepatitis C virus (HCV)), *Filoviridae* (Ebola and Marburg virus), *Coronaviridae* (severe acute respiratory syndrome coronavirus (SARS-CoV)), *Togaviridae* (Sindbis virus) and *Herpesviridae* (human cytomegalovirus (human CMV)), has been reported to use DC-SIGN and/or L-SIGN as recognition and adhesion receptor for enhanced infection in vitro (P. Y. Lozach et al., "The C type lectins DC-SIGN and L-SIGN: receptors for viral glycoproteins," Methods Mol. Biol. 379:51-68 (2007)).

DC-SIGN and L-SIGN are homotetrameric type II membrane proteins and can recognize a relatively large number of N-linked carbohydrates, such as mannose-containing glycoconjugates and fucose-containing Lewis bloodgroup antigen, on viral enveloped glycoproteins through a C-terminal carbohydrate recognition domain (D. A. Mitchell et al., "A novel mechanism of carbohydrate recognition by the C-type lectins DC-SIGN and DC-SIGNR. Subunit organization and binding to multivalent ligands," J. Biol. Chem. 276:28939-28945 (2001); H. Feinberg et al., "Structural basis for selective recognition of oligosaccharides by DC-SIGN and DC-SIGNR," Science 294:2163-2166 (2001)). Of the four glycoproteins on PRRSV virion envelope, GP2a, GP3, GP4 and GP5 contain 2 to 7 N-glycosylation sites, respectively, based on the computer prediction. Endoglycosidase treatment suggested that all putative sites are occupied by complex-type N-glycans (Meulenberg et al., 1998, supra). These observations suggest that DC-SIGN/L-SIGN may interact with one or more glycoproteins on PRRSV virion, thus mediating PRRSV entry and endocytosis. DC-SIGN is expressed on DCs and some types of macrophages, which are both important targets for PRRSV replication. L-SIGN was found to be expressed on sinusoidal endothelial cells and on placental macrophages. Placental expression of DC-SIGN was found to mediate intrauterine vertical transmission of HIV (Soilleux et al., 2001, supra). Coincidently, PRRSV is known to cause severe reproductive diseases in pregnant sows.

SARS-Coronavirus, belonging to the family *Coronaviridae* in the order *Nidovirales* together with the *Arteriviridae* family in which PRRSV is a member, was also shown to use the S glycoprotein to bind to DC-SIGN and L-SIGN during virus infection and pathogenesis (Marzi et al., 2004, supra; Z. Y. Yang et al., "pH-dependent entry of severe acute respiratory syndrome coronavirus is mediated by the spike glycoprotein and enhanced by dendritic cell transfer through DC-SIGN," J. Virol. 78(11):5642-50 (2004)). Although PRRSV and coronaviruses belong to the same super family, further testing is necessary to determine whether PRRSV will similarly use the DC-SIGN or L-SIGN for infection and pathogenesis.

A recent study reported that the Nipah virus surface glycoprotein protein (NiV-G) was able to bind to hLSECtin and hLSECtin was the putative receptor for Nipah virus surface glycoprotein protein (NiV-G) (T. A. Bowden et al., "Crystal Structure and Carbohydrate Analysis of Nipah Virus Attachment Glycoprotein: A Template for Antiviral and Vaccine Design," J. Virol. in press 2008). The interaction was mediated by the GlcNAcβ1-2Man terminal structures in NiV-G. The envelope surface glycoproteins of Ebola virus (the truncated glycans) as well as the spike protein of severe acute respiratory syndrome coronavirus (SARS-CoV) bear these carbohydrate motifs and are uniquely recognized by hLSECtin (T. Gramberg et al., "LSECtin interacts with filovirus glycoproteins and the spike protein of SARS coronavirus," Virology 340(2):224-36 (2005)). Unlike hDC-SIGN and hL-SIGN, the hLSECtin selectively bound to the glycoproteins terminating in the disaccharide GlcNAcβ1-2Man.

Furthermore, DC-SIGN and L-SIGN are considered two independent genes in the genomic level in human. Due to conserved sequences, they may have similar but distinct functions as shown in previous DC-SIGN/L-SIGN human studies. However, the biological or physiological role of L-SIGN is limited to the liver (mRNA of L-SIGN is only expressed in the liver) whereas DC-SIGN functions in the dendritic cells throughout the body.

Other related art has been published on human C-type lectin and human DC-SIGN. For instance, U.S. Pat. No. 6,190,886 (Hoppe et al.) describes a polypeptide comprising a collectin C-type lectin domain of human SP-D and the neck-region-lectin domain purified from lysates of bacterial cultures induced to express the recombinant proteins, wherein the polypeptide is able to trimerize in the collectin neck region. The suggested uses for the trimerized polypeptides are seeding collagen formation, as peptide-ligands for receptors, especially low-affinity binding (e.g., neuropeptides, interleukins), antigens, chemical compounds that are reactive upon activation, e.g., photo-activatable chemical crosslinkers, organic compounds such as caffeine and morphine, low affinity binding domains especially for the screening of potential inhibitors in pharmaceutical research, etc.

U.S. Pat. No. 6,455,683 (Yang et al.) describes isolated cDNA sequences encoding a human C-type lectin and three homologues referred to as "CLAX" (C-type Lectin, Activation Expressed) proteins. The patent discloses methods of using the nucleic acid sequences, polypeptides, fusion proteins having all or a portion (e.g., an extracellular region) of the human CLAX proteins, antibodies specific for the CLAXs, ligands and inhibitors for the human CLAXs. It is suggested that pharmaceutical compositions containing the proteins are used for the prevention and treatment of infectious, inflammatory and allergic diseases.

U.S. Pat. No. 6,280,953 (Messier et al.) provides methods for identifying polynucleotide and polypeptide sequences in human and/or non-human primates which may be associated with a physiological condition, such as disease including susceptibility (human) or resistance (chimpanzee) to development of AIDS. The physiological trait includes resistance to the progression of AIDS; the polynucleotide may be a human DC-SIGN gene; and the modulated function is then increased resistance to the progression of AIDS. It is suggested that the sequences are useful as host therapeutic targets and/or in screening assays.

U.S. Pat. No. 6,365,156 (Lee) relates to methods of increasing the half-life of a viral-specific ligand to be administered on a mucosal membrane wherein said membrane is colonized with bacteria, such as *Lactobacillus, Streptococcus, Staphylococcus, Lactococcus, Bacteriodes, Bacillus,* and *Neisseria,* by modifying the bacterial-specific ligand to bind the bacteria colonized on the mucosal membrane. The patent also discloses a chimeric molecule comprising a viral-specific ligand such as CD4, DC-SIGN, ICAM-1, HveA, HveC, poliovirus receptor, vitronectin receptor, CD21, or IgA receptor sequences and a bacterial-specific ligand such as an antibody, a peptide, a polypeptide, a protein or a carbohydrate.

U.S. Pat. No. 6,391,567 (Littman et al.) concerns human DC-SIGN as a receptor that is specifically expressed on dendritic cells and facilitates infection of T lymphocytes with Human Immunodeficiency Virus (HIV). The patent provides assays for identifying compounds that modulate the interaction of DC-SIGN and HIV and/or T cells and macrophage wherein the compounds inhibit the trans-enhancement of HIV entry into a cell.

U.S. Pat. No. 7,148,329 (Figdor et al.) deals with the use of mannose, fucose, plant lectins, antibiotics, proteins or antibodies against C-type lectins, that binds to a C-type lectin on the surface of a dendritic cell, in the preparation of a composition for modulating the immune response by modulating the adhesion of C-type lectin receptors on the surface of dendritic cells to the ICAM-receptors on the surface of T cells. The patent discloses antibodies that inhibit binding between dendritic cells and T-cells, that is, between DC-SIGN on the surface of a dendritic cell and an ICAM-3 receptor on the surface of a T-cell. The compositions are proposed for preventing/inhibiting immune responses to specific antigens, for inducing tolerance, for immunotherapy, for immunosuppression, for the treatment of auto-immune diseases, the treatment of allergy, and/or for inhibiting HIV infection.

As noted above, there is a biological relationship between DC-SIGN and ICAM-3 as part of an immunological superfamily. The intercellular adhesion molecules (ICAMs) are type I transmembrane glycoproteins belonging to a subfamily in the immunoglobulin (Ig) superfamily. Thus far, five members of the ICAM family (ICAMs 1-5) have been identified in mammals (C. G. Gahmberg et al., "Leukocyte adhesion--structure and function of human leukocyte beta2-integrins and their cellular ligands," Eur. J. Biochem. 245:215-232 (1997)). They share functional and structural Ig-like domains and mediate cell-to-cell adhesion interactions relevant for the function of the immune system (T. A. Springer, "Traffic signals for lymphocyte recirculation and leukocyte emigration: the multistep paradigm," Cell 76:301-314 (1994)). Except for ICAM-5, all other ICAM members bind to the integrin LFA-1 (CD11a/CD18) but showing large variation in tissue distributions (Gahmberg et al., 1997, supra). These adhesive interactions play important roles in mediating leukocyte trafficking through inflamed and uninflamed tissues and contribute to antigen-specific T-cell response. Of the ICAM members, ICAM-3 is thought to be the dominant ligand for LFA-1 during the initiation of the immune response, since both ICAM-1 and ICAM-2 are not expressed, or expressed at a very low level, on resting leukocytes and antigen-presenting cells (APC) (A. R. de Fougerolles et al., "Cloning and expression of intercellular adhesion molecule 3 reveals strong homology to other immunoglobulin family counter-receptors for lymphocyte function-associated antigen 1," J. Exp. Med. 177:1187-1192 (1993)). The binding of ICAM-2 and ICAM-3 to the C-type lectin, human DC-SIGN, has been reported in that interaction of ICAM-3 with DC-SIGN establishes initial contact between dendritic cells and resting T-cells during antigen presentation whereas binding of ICAM-2 to human DC-SIGN regulates emigration of dendritic cells and transmigration through endothelium (T. B. Geijtenbeek et al., "Identification of DC-SIGN, a novel dendritic cell-specific ICAM-3 receptor that supports primary immune responses," Cell 100:575-585 (2000); T. B. Geijtenbeek et al., "DC-SIGN-ICAM-2 interaction mediates dendritic cell trafficking," Nat. Immunol. 1:353-357 (2000)).

Full-length ICAM molecules contain a signal peptide sequence, two (ICAM2 and ICAM4), five (ICAM1 and ICAM3) or nine (ICAM-5) extracellular Ig-like domains, a hydrophobic transmembrane domain (TMD), and a cytoplasmic tail (CT). Each Ig-like domain is encoded by a distinct exon (G. Voraberger et al., "Cloning of the human gene for intercellular adhesion molecule 1 and analysis of its 5'-regulatory region. Induction by cytokines and phorbol ester," J. Immunol. 147:2777-2786 (1991); C. M. Ballantyne et al., "Characterization of the murine Icam-1 gene," Genomics 14:1076-1080 (1992)). Isoforms of murine ICAM-1 generated by alternative splicing have been identified in ICAM-1-deficient mice (P.D. King et al., "Novel isoforms of murine intercellular adhesion molecule-1 generated by alternative RNA splicing," J. Immunol. 154:6080-6093 (1995); N.K. van Den Engel et al., "Circulating forms of intercellular adhesion molecule (ICAM)-1 in mice lacking membranous ICAM-1," Blood 95:1350-1355 (2000)). Each murine ICAM-1 isoform is generated from the complete skipping of exons encoding Ig-like domains 2, 3, and/or 4. In addition, the existence of an alternative 5' splice site in exon 6 also yields a murine ICAM-1 isoform with a 69-nt deletion from the 3'-terminus of exon 6 (J. P. Mizgerd et al., "Exon truncation by alternative splicing of murine ICAM-1," Physiol. Genomics 12:47-51 (2002)). In murine ICAM-4, a transmembrane-domain-lacking isoform causing by intron retention was also identified (G. Lee et al., "Novel secreted isoform of adhesion molecule ICAM-4: potential regulator of membrane-associated ICAM-4 interactions," Blood 101:1790-1797 (2003)). All the ICAM isoforms identified to date are fully functional, indicating that alternative mRNA splicing plays distinct roles in different immune response pathways.

Two comparative sequence analysis studies based on human-pig-mouse-rat or human-dog-mouse-rat genomic regions revealed that the ICAM3 gene has been lost in the rodent genome (H. Sugino, "ICAM-3, a ligand for DC-SIGN, was duplicated from ICAM-1 in mammalian evolution, but was lost in the rodent genome," FEBS Lett. 579:2901-2906 (2005); T. Leeb and M. Muller, "Comparative human-mouse-rat sequence analysis of the ICAM gene cluster on HSA 19p13.2 and a 185-kb porcine region from SSC 2q," Gene 343:239-244 (2004)). The organization of ICAM3 genes in human, non-human primates and bovine is similar, which contains seven putative exons, and exons 3 to 7 are clustered at the 3'-proximal region of the gene (P. Kilgannon et al., "Mapping of the ICAM-5 (telencephalin) gene, a neuronal member of the ICAM family, to a location between ICAM-1 and ICAM-3 on human chromosome 19p13.2," Genomics 54:328-330 (1998); E. K. Lee et al., "Cloning and sequencing of a cDNA encoding bovine intercellular adhesion molecule 3 (ICAM-3)," Gene 174:311-313 (1996)). For porcine ICAM-3, the gene sequence is not yet completely known since only the region from exon 1 to partial exon 5 has been identified and sequenced (Leeb and Muller, 2004, supra). In addition, the cDNA of porcine ICAM-3 has not been identified thus far.

Nonsense mutations falling within an exon can induce exon skipping during the pre-mRNA splicing process, which is designated as nonsense-associated altered splicing (NAS) (L. Cartegni et al., "Listening to silence and understanding nonsense: exonic mutations that affect splicing," Nat. Rev. Genet. 3:285-298 (2002); L.E. Maquat, "The power of point mutations," Nat. Genet. 27:5-6 (2001); H. C. Dietz et al., "The skipping of constitutive exons in vivo induced by nonsense mutations," Science 259:680-683 (1993)). NAS is usually disease-associated, as has been shown in a few disease-causing genes (Cartegni et al., 2002, supra), since premature termination of translation would result in failing to produce a functional protein. The mechanisms of NAS are believed to be due to the occurrence of a translation-like nucleus scanning before slicing, indirect nonsense-mediated mRNA decay (NMD) or exonic splicing enhancer (ESE) disruption (id.).

While human DC-SIGN is involved in the transmission of various enveloped viruses such as human immunodeficiency virus, hepatitis C virus, Dengue virus and SARS-Coronavirus to their respective target cells, the characteristics and properties of DC-SIGN proteins obtained from other species have not been shown to mimic hDC-SIGN as a rule. Therefore, further testing is necessary to allocate the function of any given DC-SIGN. Before the current discovery, the DC-SIGN and other LSECtin related homologues from the pig species had not yet been isolated, identified or characterized.

It is therefore an important object of the present invention to obtain the cloning and characterization of the full nucleic acid molecule encoding new porcine DC-SIGN and porcine LSECtin proteins heretofore not described in the pig genome database.

It is another important object of the invention to identify and characterize the complete nucleic acid molecules encoding new porcine ICAM-3 isoforms from in vitro cultured porcine monocyte-derived dendritic cells.

It is an additionally significant object of the invention to use pDC-SIGN, pLSECtin, pICAM-3 alone or in certain combinations as fused proteins with hDC-SIGN, hL-SIGN or hLSECtin in a new method for propagating viruses, particularly enveloped viruses with an emphasis on porcine enveloped viruses, making use of new transfected cells or cell lines stably expressing pDC-SIGN, pLSECtin and/or pICAM-3.

It is a further object of the invention to raise an antibody that specifically binds to an amino acid sequence of the pDC-SIGN protein and is utilizable to enhance the immunogenic activity of poor antigenic substances. Raising an antibody that specifically binds to an amino acid sequence of the pLSECtin and pICAM-3 proteins is also highly desirable.

Further purposes and objects of the present invention will appear as the specification proceeds.

The foregoing objects are accomplished by providing and isolating the new and complete nucleic acid sequences encoding pDC-SIGN, pICAM-3 and pLSECtin, using the nucleotide sequences encoding the proteins in specially designed vectors to propagate enveloped viruses, raising antibodies and the like.

BRIEF SUMMARY OF THE INVENTION

The present invention concerns the entire porcine DC-SIGN gene and the cDNA clone obtained from porcine monocyte-derived dendritic cells, plus the novel porcine DC-SIGN protein encoded by the new gene. The invention also relates to the full gene and cDNA obtained from liver tissue of a pig and the novel encoded pLSECtin protein. In addition, the invention encompasses two new cDNA isoforms of porcine ICAM-3 isolated from in vitro cultured porcine monocyte-derived dendritic cells. Specifically, the invention is drawn to an isolated nucleic acid molecule comprising a nucleotide sequence encoding one or more of porcine DC-SIGN, porcine ICAM-3, porcine LSECtin, a complement of the nucleotide sequence or a functional, defined portion of the nucleotide sequence or certain protein fusion products that may be linked with another protein that may be of porcine or human origin. Also included within the scope of the invention are biologically functional plasmids, viral vectors and the like that contain the new nucleic acid molecules described herein, stable cells or cell lines transfected transiently by the plasmid or the vector of the present invention and the polypeptide expression products. An important embodiment of this invention further embraces a new use for the porcine homologues in a method for propagating viruses, particularly enveloped viruses.

BRIEF DESCRIPTION OF THE DRAWINGS

The background of the invention and its departure from the art will be further described herein below with reference to the accompanying drawings, wherein:

FIG. 1(a) shows the morphologic development of porcine MDDCs after 7-day in vitro culture of CD14 monocytes in the presence of rpGM-CSF and rpIL-4 at magnification=400×. FIG. 1(b) shows the detection of a ~210-bp product with expected size by RT-PCR with degenerate primers. FIG. 1(c) shows the results of 5'-RACE and 3'-RACE PCR.

FIGS. 2a and 2b represent the complete nucleotide sequence of pDC-SIGN cDNA (which corresponds to SEQ ID NO:1) and its deduced amino acid sequence (which corresponds to SEQ ID NO:2). The 1,069-nucleotide sequence contains an open reading frame encoding a 240-aa protein beginning at nt position 26. The predicted transmembrane domain (TMD) is indicated by a dash-lined box and the carbohydrate recognition domain (CRD) is underlined. The polyadenylation signal is boxed. Arrows show the boundary of exons.

FIG. 3(a) provides the immunofluorescence assay (IFA) results at 48 hours post transfection with a pDC-SIGN-specific anti-peptide polyclonal antibody (magnification=200x). Most cells had a spreading cytoplasmic and membrane staining FIG. 3(b) shows that a few cells only had cell membrane staining Inner panels indicate the magnification (400x) of the stained cells. FIG. 3(c) represents the transfection of cells with the vector pCI-neo as a negative control (200x). FIG. 3(d) shows Western blot analysis using cell lysates of BHK-21 cells transfected with plasmids pCI-PDCS or pCI-neo.

FIGS. 4a and 4b illustrate the cloning of the porcine DC-SIGN gene in which FIG. 4(a) shows the amplification results of the porcine DC-SIGN gene pig genomic DNA by one-step genomic PCR and FIG. 4(b) shows the assembly of one of the three clones (GDCS-6) of porcine DC-SIGN gene from five individual sequences using the respective sequencing primers, M13F, 2F, 3F, 4F and M13R.

FIGS. 5a, 5b, 5c and 5d represent the complete nucleotide sequence (includes exons and introns) of the porcine DC-SIGN gene localized on the chromosomal DNA (which corresponds to SEQ ID NO:3). The positions of exons 1-8, the genomic PCR primers 1F and 4R and the sequencing primers 2F, 3F and 4F are indicated.

FIGS. 6a to 6d show the detection of pDC-SIGN expression in selected pig tissues and cell populations by RT-PCR and flow cytometry. FIG. 6a represents the RT-PCR expression profile showing the mRNA expression of pDC-SIGN. Pig tissue cDNA were used as templates in PCR reactions with primers PDCS-E56F/PDCS-E78R or porcine GAPDH-specific primers. FIGS. 6b to 6d demonstrate the detection of pDC-SIGN expression on defined porcine cell populations and cell lines. Porcine PBMC were isolated by centrifugation on Ficoll and assessed for forward and side scatter properties. The peripheral blood lymphocytes (PBL, CD14$^-$ cells) and monocytes (CD14$^+$ cells) were separated by immunomagnetic labeling MACS system using anti-CD14 monoclonal antibody. In the other panels, the expression of pDC-SIGN on PBL, monocytes, monocyte-derived dendritic cells (MD-DCs), monocyte-derived macrophages (MDMΦs), porcine alveolar macrophages (PAM), porcine monocytic cell line 3D4/31 and porcine kidney epithelial cell line PK15 were assessed by staining with anti-pDC-SIGN antibody (cross-hatched histograms). Dashed open histograms indicate background controls. Data are representative of three independent experiments.

FIG. 7(a) shows that pDC-SIGN protein was preferentially expressed in lymph node sinuses (supcapsular sinuses). FIG. 7(b) shows that pDC-SIGN protein was not expressed in pig liver. FIG. 7(c) shows that most of the cells immunostained with pDC-SIGN-specific anti-peptide antibody in sinuses were morphologically macrophage-like (arrow) and dendritic-like cells (arrowhead). FIG. 7(d) shows that lymphatic vessel endothelial cells in parenchyma were also immunostained with pDC-SIGN-specific antibody.

FIGS. 8a to 8e show the binding of human ICAM-3 and ICAM-2 immunoadhesins to BHK cells stably expressing pDC-SIGN. FIG. 8a provides the detection of surface expression of pDC-SIGN protein on stable BHK cell lines. BHK-21, and unsorted or sorted BHK-PDCS cell lines were stained with anti-pDC-SIGN antibody and FITC-labeled goat anti-rabbit IgG, respectively, and analyzed by flow cytometry. Dashed open histograms represented the background staining The expression of pDC-SIGN was indicated by the cross-hatched histograms. Expression of hDC-SIGN on the surface of 3T3-HDCS cell line was also verified by staining with a hDC-SIGN monoclonal antibody (right, bottom panel). FIGS. 8b to 8e illustrate the calcium-dependent binding of human ICAM-3 and ICAM-2 immunoadhesins to BHK-PDCS and 3T3-HDCS cells. Dashed open histograms represent cells staining only with a FITC labeled anti-human IgG Fc antibody. Results are representative of three independent experiments. Data are expressed as histogram analysis of 10,000 cells.

FIG. 9a shows that PRRSV is replication-competent in BHK-PDCS cells by transfection with a modified PRRSV infectious cDNA clone expressing GFP (left panel) and the released virus is able to infect target MARC-145 cells (right panel). GFP signal was directly monitored at 48 hours post-transfection in BHK-PDCS cells or at 72 hours post infection in MARC-145 cells (magnification=100x). FIG. 9b shows the comparison of PRRSV binding on BHK-PDCS and BHK-21 cell lines. Dotted open histograms represent control cells incubated without PRRSV inoculation but stained with anti-PRRSV mAb SDOW17-A and FITC-labeled goat anti-mouse IgG. Cells inoculated with the virus and incubated with the two antibodies are indicated by cross-hatched histograms. FIG. 9c shows that both PRRSV strain PGXG and strain VR2385 blocked hICAM-3 binding to the BHK-PDCS cell line. BHK-PDCS cells were incubated with either PGXG or VR2385 (M.O.I.=10 FFU per cell) for 60 min at 4° C. before the addition of hICAM-3-Fc. The stained cells were analyzed using FACS as described herein. Data are presented as the mean fluorescence intensity normalized to the untreated control (addition of a hICAM-3-Fc and a FITC labeled anti-human IgG Fc antibody only)±SD. Asterisks indicated statistical difference compared with the untreated control ($p<0.05$). FIG. 9d shows that PRRSV transmission mediated by BHK cells was enhanced by pDC-SIGN. Transmission of either PRRSV PGXG or PRRSV VR2385 using BHK-PDCS, BHK-21 and MARC-145 cells as donor cells and MARC-145 cells as target cells and titration of PRRSV were performed as described in the examples. Donor cells co-cultured with MARC-145 target cells not exposed to PRRSV were used as mock-transmission control and the results were not shown in the figure (no virus detected). Asterisk indicated statistical difference for PRRSV VR2385 strain between BHK-PDCS and BHK-21 cells ($p<0.05$).

FIG. 10 illustrates the amplification of porcine ICAM-3 cDNA from in vitro cultured porcine monocyte-derived dendritic cells (MDDCs) by RACE-PCR. FIG. 10(*a*) demonstrates the identification of two isoforms (~800 by each) by 5'-RACE PCR. FIG. 10(*b*) confirms the detection of a ~700 by products by 3'-RACE PCR.

FIGS. 11*a* and 11*b* provide the complete nucleotide sequence of porcine ICAM-3 cDNA (which corresponds to SEQ ID NO:4) and predicted protein sequence (which corresponds to SEQ ID NO:5). The nucleotide position is labeled on the right and the amino acid (aa) position is labeled under each residue. A small open reading frame predicted to encode a 63-aa peptide (which corresponds to SEQ ID NO:38), which is upstream the putative ICAM-3 coding region in the large 5'-RACE PCR product, is indicated in parenthesis. The sequence of the deletion nucleotide region found in the small 5'-RACE PCR product (which corresponds to SEQ ID NO:39) is shown in a dashed box. The putative signal peptide is indicated by a double-dashed line and the potential polyadenylation signal is indicated by a dashed line. The heavy underlined sequence represents the predicted transmembrane region. Potential N-glycosylation sites are indicated by —N—. Proposed start points for Ig-like domains 1-3 and transmembrane domain (TMD) plus cytoplasmic tail (CT) are marked with arrows above the corresponding nucleotide sequence.

FIG. 12a shows the comparison of the pre-mRNA splicing and protein expression between porcine ICAM-3 and primates/bovine ICAM-3. All the ICAM-3s share similar genomic structure, which contains seven putative exons (E1 to E7), and exons 3 to 7 are clustered at the 3'-proximal region of the genome. In primates and bovine species, routine pre-mRNA splicing occurs, resulting in the inclusion of all 7 exons (illustrated with heavy lines and arrows). Exon 1 encodes the signal peptide, exons 2 through 6 encode D1 through D5, respectively, and exon 7 encodes transmembrane domain plus cytoplasmic tail. In porcine specie from this study, absence of D4 and D5 in the predicted ICAM-3 protein is proposed to result from continuous skipping of exons 5 and 6 (e5 and e6) during the pre-mRNA splicing process (illustrated with light lines and arrows). The partial, known genomic DNA sequence of porcine ICAM-3 is referred from AJ632303 (clone RP44-379M9) while the remaining unknown sequence of porcine ICAM-3 is determined in the experiments for the present invention. FIG. 12b gives the determination of the sequence of the unknown region between e5 and E7 of porcine ICAM-3 gene by genomic PCR amplification of a genomic DNA fragment using primers PIC53 and PIC58 (series of sequences from left to right box correspond to SEQ ID NO:40, SEQ ID NO:41 and SEQ ID NO:42, respectively). Compared to primates/bovine ICAM-3s, porcine ICAM-3 exon 5 contains a 3-nt in-frame nonsense mutation (CTT to TGA, underlined) while exon 6 contains four in-frame nonsense mutations (underlined) due to an upstream 4-nt deletion (AAAG). The point mutation (g to a) at the first nucleotide of putative splice donor site in intron 6 (I6) is indicated with asterisk.

FIGS. 14a to 14c show the gene structure and nucleotide sequence of the cDNA of pLSECtin. FIG. 14a provides the gene structure of pLSECtin gene. The top row displayed the exon allocation of domains. The below row represented the domain structure of the putative pLSECtin coding region. CT: Cytoplasmic tail; TMD: Transmembrane domain; CRD: Carbohydrate recognition domain. Un-translated regions in exons 1 and 9 were shown as open boxes. FIGS. 14b and 14c provide the complete nucleotide sequence of pLSECtin cDNA (which corresponds to SEQ ID NO:36) and its deduced amino acid sequence (which corresponds to SEQ ID NO:37). Extra nucleotide sequences at both termini in the noncoding region of pLSECtin cDNA that were not determined in this study were included with dashed underlines. The two in-frame initiation codons and the stop codon were boxed. Two potential internalization motifs, YSKW and EE in the CT, were indicated by dashed-lined boxes. The putative TMD was indicated by a double-lined box and the carbohydrate recognition domain (CRD) is underlined. Two predicted glycosylation sites in the neck region were marked by dotted underlines. The polyadenylation signal (AATAAA) was indicated by capitals. Arrows show the boundary of exons.

DETAILED DESCRIPTION OF THE INVENTION

Figure 1:
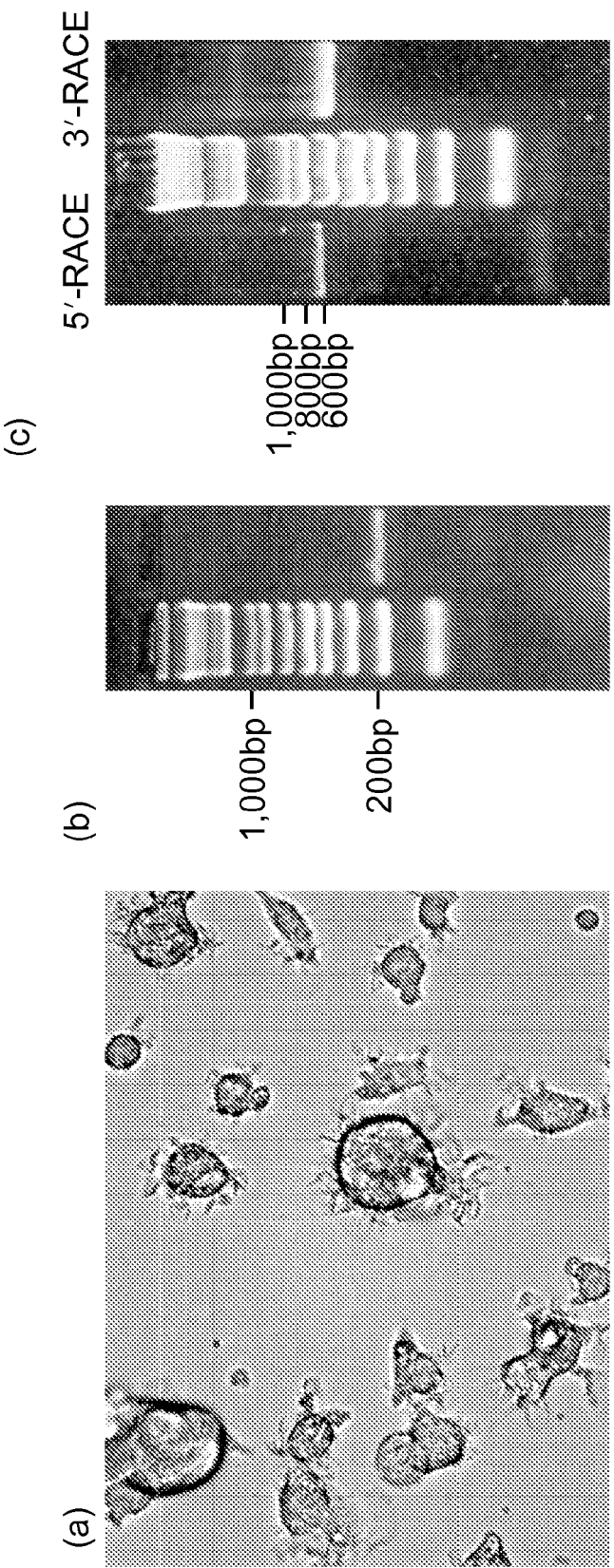
FIG. 1 shows the amplification of pDC-SIGN cDNA from in vitro cultured porcine monocyte-derived dendritic cells (MDDCs) by RT-PCR or RACE-PCR and amplification of pDC-SIGN gene from pig genomic DNA by genomic PCR.

In accordance with the present invention, there are provided isolated nucleic acid molecules, heretofore unknown, comprising nucleotide sequences encoding one or more proteins selected from the group consisting of porcine DC-SIGN (pDC-SIGN), porcine ICAM-3 (pICAM-3), porcine LSECtin (pLSECtin), complements of at least one of the nucleotide sequences and the functional fragments that comprise a functional, defined portion of at least one of the nucleotide sequences.

Using genomic PCR techniques, this invention shows the molecular cloning and characterization of the entire gene and cDNA sequence encoding the unique pDC-SIGN isolated from in vitro cultured porcine monocyte-derived dendritic cells of Sus scrofa (wild boar, a member of the pig family). Unlike the computer-based screening of DC-SIGN homologues in the genome databases of mouse and other species previously described in the literature, DC-SIGN-related porcine gene sequences have not been available in the pig genome database and, thus, provided a challenge to clone the full nucleic acid sequence.

Also included in the scope of the present invention is the complete gene and cDNA sequence encoding the new pLSECtin protein isolated from porcine liver tissue. The disclosure of this invention depicts the tissue and cellular distribution of the relevant porcine proteins, illustrates the cross-interactions between pDC-SIGN and hICAM-3, shows the cross-interactions between pDC-SIGN and hICAM-2 and, of particular significance, demonstrates the enhancement of PRRSV transmission to target cells in trans by pDC-SIGN.

The basis for the present invention lies in the reports that hDC-SIGN and hL-SIGN may be binding receptors for many enveloped viruses, especially those viruses that replicate in macrophages and dendritic cells such as PRRSV. Human DC-SIGN may also mediate PRRSV pathogenesis in the reproductive system and be involved in reproductive failure. Now that the porcine-specific DC-SIGN and pLSECtin genes are herein identified and compared to hDC-SIGN and hL-SIGN with the present observation of unexpected similarities in protein structures, it is herein determined that PRRSV may utilize pDC-SIGN to facilitate entry into macrophages and dendritic cells, and the expression of pDC-SIGN in replication-competent cells such as BHK-21 can result in productive PRRSV replication. As such, the present invention is further drawn to genetically engineered stable, transfected cells or cell lines that will efficiently support productive PRRSV replication.

Surprisingly observed in connection with the present invention is that porcine LSECtin is highly identical with human LSECtin at the amino acid level, which shows that pLSECtin shares the same carbohydrate-protein interaction pattern as hLSECtin. Previous studies reported the ability of the Nipah virus surface glycoprotein protein (NiV-G) to bind to human LSECtin and the possible function of the hLSECtin as the putative receptor for NiV-G (T. A. Bowden et al., in press 2008, supra). Other studies reported that the envelope protein of Ebola virus as well as the spike protein of SARS-CoV bear the same carbohydrate motifs and are also recognized by hLSECtin (T. Gramberg et al., 2005, supra). Due to the similarities now seen between the newly discovered pLSECtin of the invention and hLSECtin, the new pLSECtin may serve as a pathogen recognition receptor (PRR) to trigger the host innate immune responses and facilitate the transmission and spread of Nipah virus or other pathogenic porcine enveloped viruses during the infection in pig. As such, the utility of pLSECtin includes the design of specific antivirus drugs (for instance, carbohydrate ligands, siRNA, etc.) to block the virus-pLSECtin interaction, the development of virus vaccines that contain factors stimulating the pLSECtin-dependent antigen recognition and improving host innate immune responses to enhance the efficacy of the vaccines, and the like.

Also included in the present invention are fused or fusion proteins. While the fusion protein may comprise pLSECtin linked to pDC-SIGN, the fused protein may also comprise pLSECtin or pDC-SIGN linked to the functional, defined portions of the other protein. Either alone or fused, pLSECtin, pDC-SIGN or the functional, defined portions thereof may be further fused to at least one protein selected from the group consisting of hDC-SIGN, hL-SIGN, hLSECtin and a combination thereof, or a functional, defined portion thereof The functional, defined portions of the proteins relate to those domains or regions identified as having immunogenic function, receptor activity or binding capacity in the pig or human homologues, for example, the carbohydrate recognition domain of pDC-SIGN or pLSECtin, the cytoplasmic tail, the transmembrane domain or the repeat neck region of hDC-SIGN, hL-SIGN, hLSECtin or a combination thereof.

In a preferred embodiment, the fused or fusion protein may contain the carbohydrate recognition domain (CRD) of pDC-SIGN or pLSECtin that is responsible for capturing antigens and the cytoplasmic tail (CT), the transmembrane domain (TMD) and the repeat neck region of hDC-SIGN, hLSECtin or hL-SIGN responsible for absorbing or engulfing the captured antigens into the cells by endocytosis.

Certain enveloped viruses such as PRRSV can only grow in limited cell lines such as the MARC-145 cell line to a limited extent and are difficult to cultivate in sufficient titers. Other cell lines such as a culture of BHK-21 cells allow PRRSV to replicate inside the cell but it does not allow PRRSV to spread from cell-to-cell, which means the virus cannot enter into other uninfected BHK-21 cells making antigen production and hence the manufacture of viable vaccine products a challenge. Advantageously, the PRRSV receptor, namely, the pDC-SIGN, pICAM-3, pLSECtin, etc., but desirably, the pLSECtin, pDC-SIGN or its fused protein construct, can be stably expressed on the surface of BHK-21 cells (i.e., the bioengineered BHK-21 cell line) allowing the virus to enter into other uninfected cells and propagate to sufficient titers.

An important aspect to the present invention, therefore, embraces a new and highly beneficial method of propagating viruses, preferably enveloped viruses (which are mainly RNA viruses) and particularly those viruses that cannot be propagated in cell culture at all or to a limited degree, in a suitable cell line. Of particular advantage to the method is the plasmid or vector stably expressing the proteins or fused protein construct of the invention for use in culturing enveloped porcine viruses, such as, for instance, Porcine Reproductive and Respiratory Syndrome virus (PRRSV), Porcine Respiratory Coronavirus (PRCV), Porcine Epidemic Diarrhea Virus (PEDV), porcine endogenous retroviruses, porcine cytomegalovirus, Swine Influenza Virus (SIV), African swine fever virus, classical swine fever virus, swine poxvirus, Porcine Hemagglutinating Encephalomyelitis Virus (PHEV) and the like, as well as Transmissible Gastroenteritis Virus (TGEV), Japanese Encephalitis Virus (JEV), human immunodeficiency virus (HIV), Dengue virus, West Nile virus, Ebola virus, Marburg virus, Severe Acute Respiratory Syndrome Coronavirus (SARS-CoV), feline coronavirus, human cytomegalovirus (human CMV), hepatitis C virus (HCV), herpes simplex virus, type A influenza virus, type B influenza virus, type C influenza virus, Simian Immunodeficiency Virus (SIV), feline immunodeficiency virus (FIV), Sindbis virus, Nipah virus, Hendra virus, bovine viral diarrhoea virus, pseudorabies virus, vesicular stomatitis virus, rabies virus, Eastern equine encephalitis virus, equine arteritis virus (EAV), etc. Preferably, the new method is employed to significantly improve the propagation of PRRSV for purposes of manufacturing porcine vaccines. Non-enveloped viruses like hepatitis E virus (HEV), porcine circovirus type 2 and others can also be used in the new method.

According to this novel method of the invention, a new bioengineered cell or cell line stably expressing pDC-SIGN, pICAM-3, pLSECtin, a complement of at least one of the nucleotide sequences, a functional, defined portion thereof or the related fused protein product is used to propagate the viruses. The expressed protein serves as the viral receptor to capture and uptake the virions into the cells. The presence of the porcine protein in this method provides a surprising advantage by aiding in cell-to-cell transfer of the virus thereby significantly enhancing the propagation of the viruses.

In one regard, the improved method employs the following steps: (a) providing a transfected cell or cell line containing a nucleotide sequence encoding one or more proteins selected from the group consisting of pDC-SIGN, pICAM-3 and pLSECtin, a complement of at least one of the nucleotide sequences and a functional, defined portion of at least one of the nucleotide sequences; (b) growing the transfected host cell or cell line in cell growth medium to form a culture; (c) inoculating said culture with the virus; and (d) incubating the inoculated culture in suitable virus medium under conditions effective to propagate the virus in the culture. The method may optionally and further comprise incubating the inoculated culture until cytopathic effect is observed or high titer is achieved; or lysing the cells to release intracellular virions; and (g) harvesting virus antigen.

The unique method for propagating viruses for process development may also involve the basic steps of: (a) transfecting a suitable cell with a vector comprising a nucleotide sequence encoding one or more proteins selected from the group consisting of pDC-SIGN, pICAM-3 and pLSECtin, a complement of at least one of the nucleotide sequences and a functional, defined portion of at least one of the nucleotide sequences or a fused protein as described herein in a manner allowing expression of the polypeptide product; (b) growing the cell that stably expresses the protein or the fusion polypeptide product to monolayer with an appropriate cell growth medium; (c) removing growth medium, inoculating virus stock into the cells followed by an initial short incubation period for usually one hour at 37° C.; (d) adding virus medium and culturing the virus for 2 to 3 days until the quantity of virus reaches a sufficient level as shown by CPE (cytopathic effect) or high titer depending on the virus; and (e) lysing the cells to release intracellular virions, performing virus titration and freezing the virus stock.

The unique porcine DC-SIGN gene is found to be homologous to human DC-SIGN and mouse SIGNR family but with certain variations as described herein. The new porcine DC-SIGN protein is found to have 240 amino acids and to be a type II transmembrane protein. Its C-terminus extracellular region contains a carbohydrate recognition domain (CRD). Surprisingly, the deduced amino acid sequence of porcine DC-SIGN is phylogenetically more closely-related to mouse SIGNR7 and SIGNR8 than to human DC-SIGN, non-human primate DC-SIGNs or other mouse SIGNR homologues, indicating a distinct evolutionary pathway of porcine DC-SIGN. Transient expression of porcine DC-SIGN protein on the surface of BHK-21 cells transfected with a eukaryotic expression plasmid containing the gene was confirmed by immunofluorescence assay with a specific anti-peptide porcine DC-SIGN antibody.

By using degenerate RT-PCR primers based upon the human, non-human primates and mouse DC-SIGN genes, a short fragment with sequence homologous to human DC-SIGN (hDC-SIGN) was amplified from in vitro cultured porcine monocyte-derived dendritic cells. Based upon the initial resulting sequence, both the complete cDNA and the gene of porcine DC-SIGN homologue were subsequently determined by rapid amplification of cDNA ends (RACE)-PCR. Further, expression of the porcine DC-SIGN gene was found to localize to the cell surface, confirming the transmembrane property of the protein. Subsequently, a pDC-SIGN-specific antibody was generated and a stable cell line expressing pDC-SIGN was developed. The gene structure, tissue and cellular distributions and in vitro binding property of pDC-SIGN to human ICAM-3 and ICAM-2 immunoadhesins as well as the potential interaction between pDC-SIGN and PRRSV were characterized.

An important embodiment of the present invention, therefore, is drawn to the isolated or purified nucleic acid molecule encoding pDC-SIGN or a cDNA clone thereof or the protein fusion product constructed from pDC-SIGN, alone or linked to hDC-SIGN, hL-SIGN, hLSECtin or any combination thereof Desirably, the nucleotide sequence encoding pDC-SIGN comprises SEQ ID NO:1 or its complementary strand. Conventional methods that are well known in the art can be used to make the complementary strands or the nucleotide sequences possessing high homology to SEQ ID NO:1, for instance, by the art-recognized standard or high stringency hybridization techniques.

Another important embodiment of the present invention is directed to the identification and characterization of the cDNA and complete gene encoding pLSECtin. Full-length pLSECtin cDNA encodes a type II transmembrane protein of 290 amino acids. It is now found that porcine LSECtin gene has the same gene structure as the human LSECtin gene as well as the predicted bovine, canis, mouse and rat LSECtin genes with nine exons. A multi-species-conserved site at the extreme 3'-untranslated region of LSECtin mRNAs was predicted to be targeted by microRNA miR-350 in domesticated animals and by miR-145 in primates, respectively. Similar to human LSECtin, pLSECtin mRNA expression was distributed in liver, lymph node and spleen. A series of sequential intermediate products of pLSECtin pre-mRNA were also identified during splicing from pig liver.

Also included within the scope of the present invention are biologically functional plasmids, viral vectors and the like that contain the new nucleic acid molecule or fusion product described herein, suitable cells transfected transiently by the plasmid or the vector of the present invention and the polypeptide expression products. For purposes of the invention, the vector, in a broad sense, may be any commercially available, standard viral vector or comparable biologically functional plasmid known to those of ordinary skill in the art, but is preferably pTriEx-1.1 Neo to achieve optimal and advantageous results from the exemplified recombinant bicistronic vector pTriEx-PDCS of the present invention.

Figure 3:
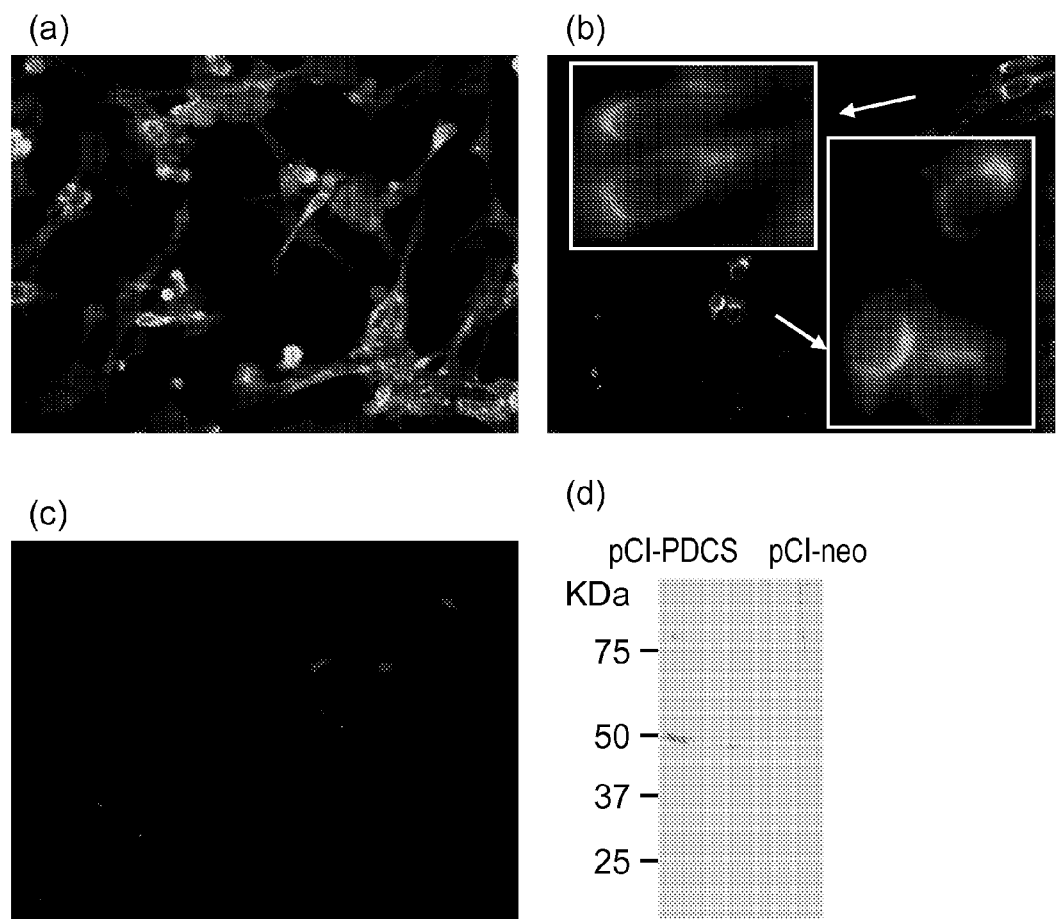
FIG. 3 demonstrates the expression of pDC-SIGN (construct pCI-PDCS) in transfected BHK-21 cells.
Figure 8B:
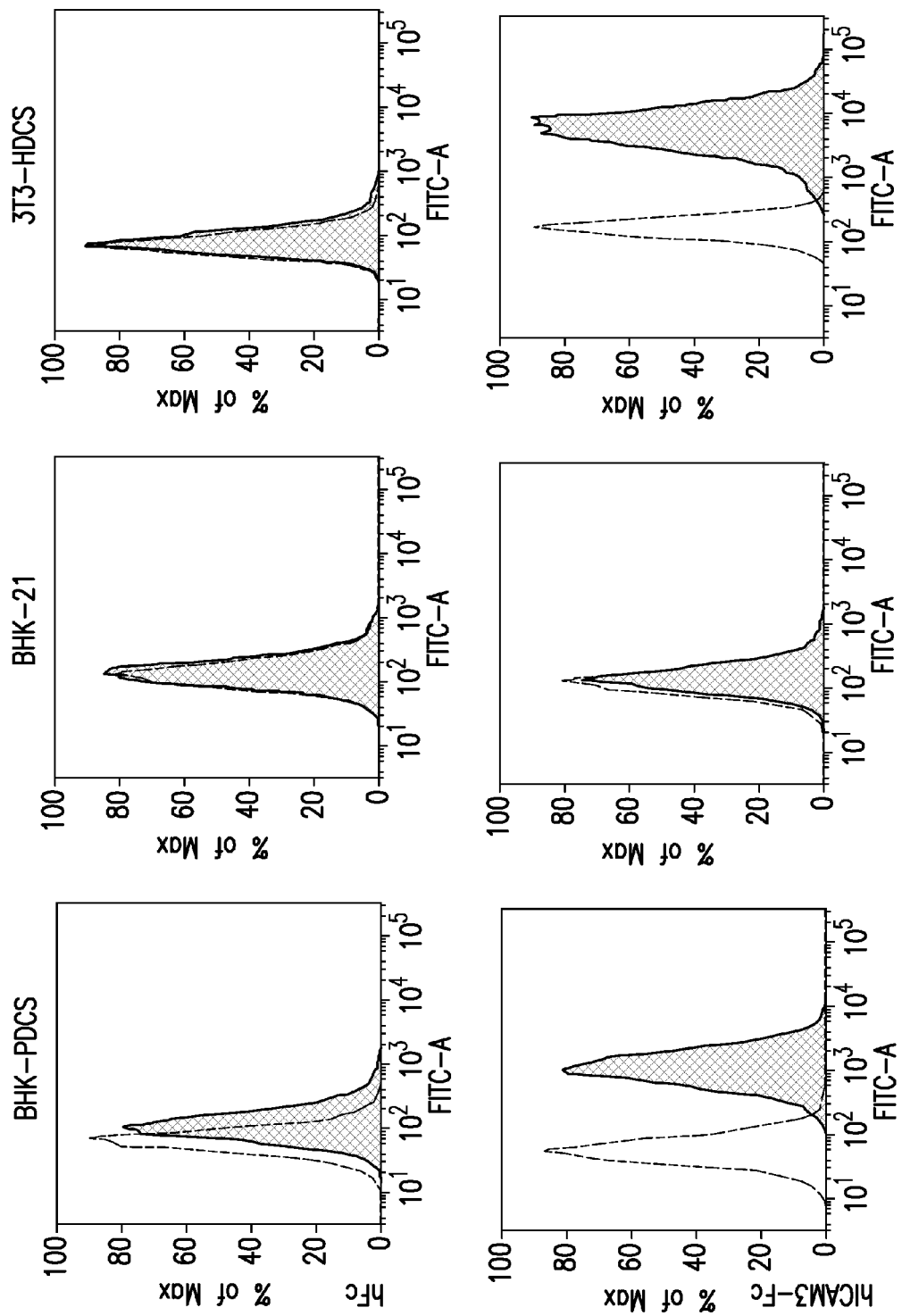
Figure 8C:
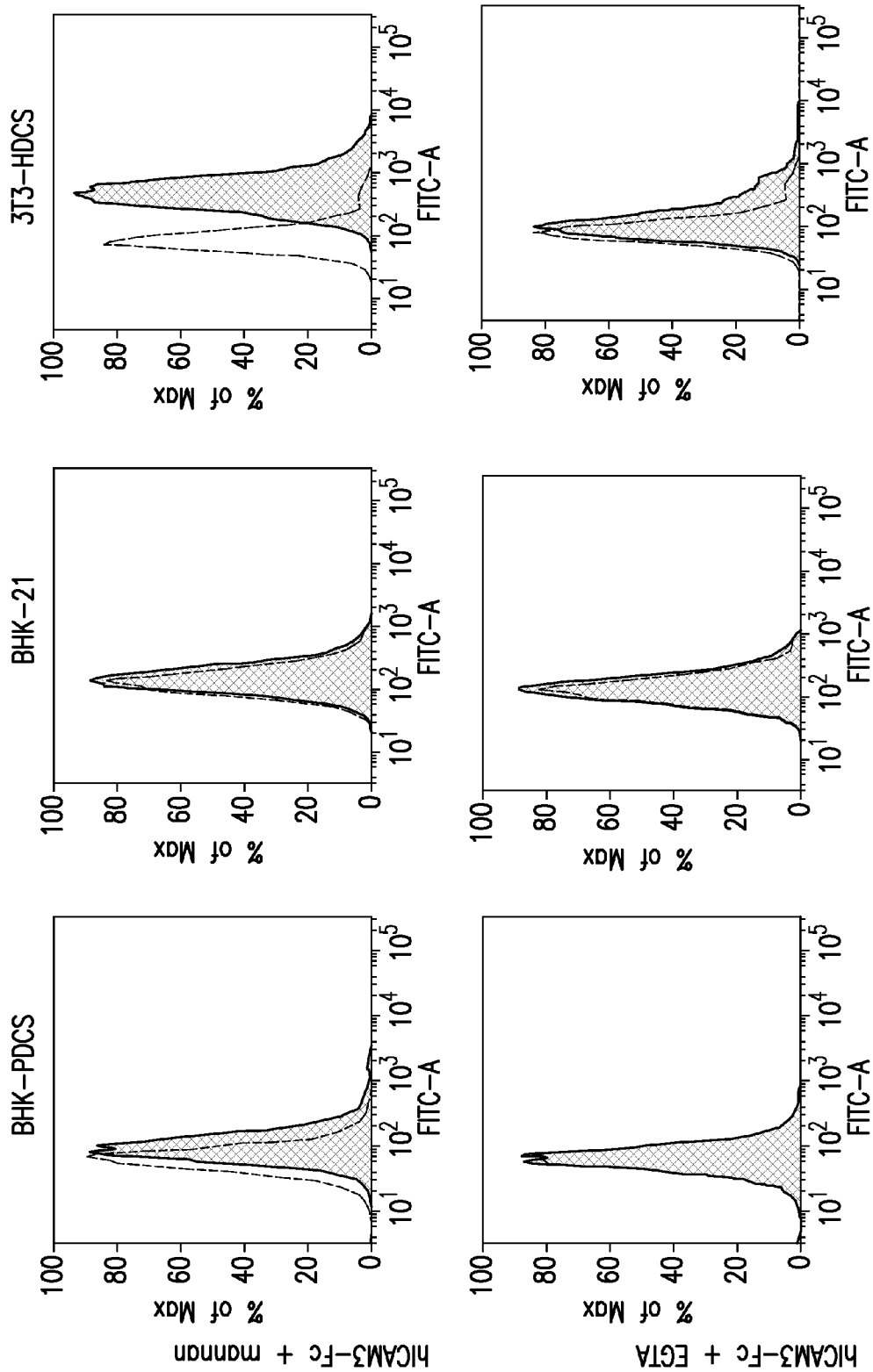
Figure 8D:
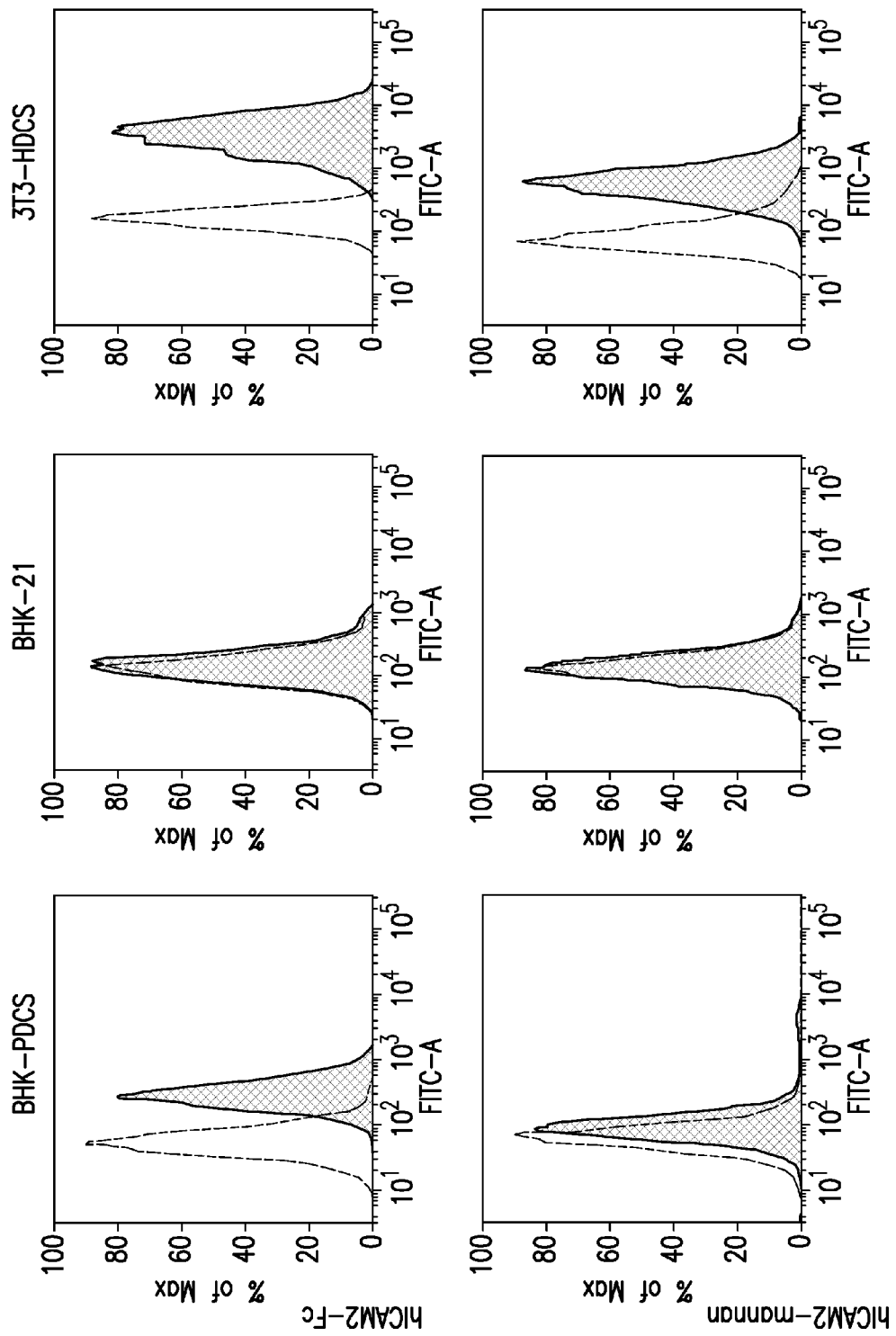
Figure 8E:
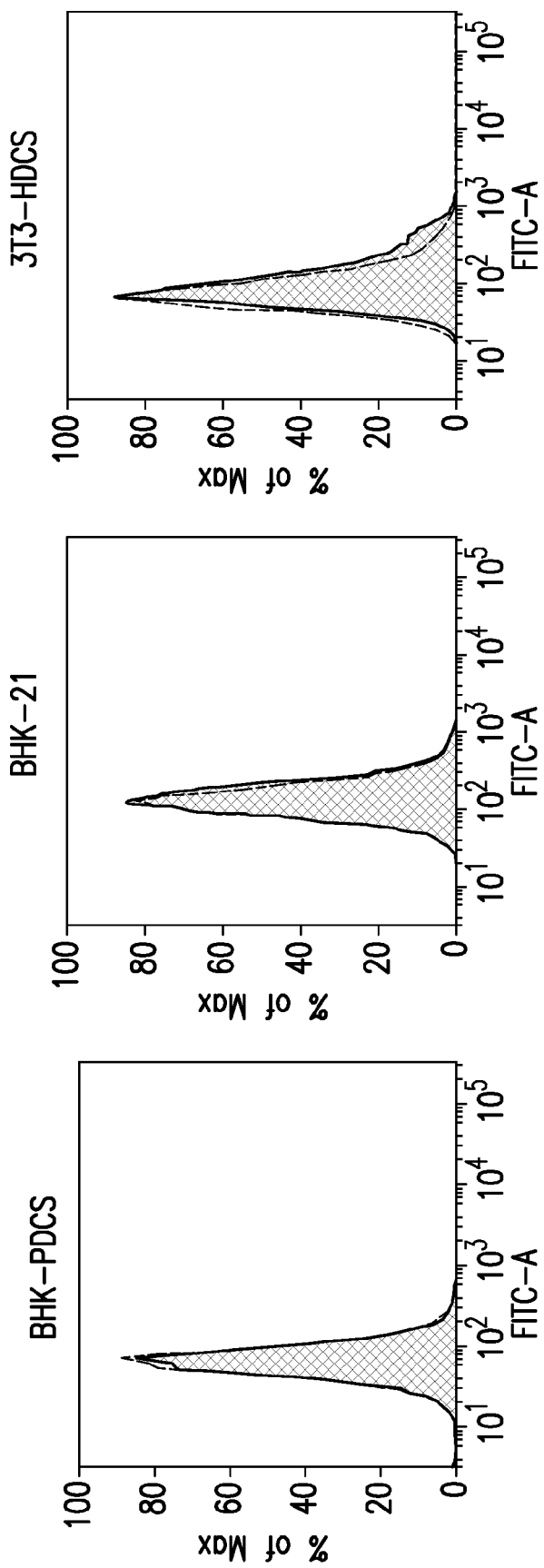

By way of illustration and comparison, pTriEx-1.1 Neo for the construction of the recombinant bicistronic vector pTriEx-PDCS and the generation of a BHK-21 cell line stably expressing porcine DC-SIGN as described herein provides a significant advantage over other vectors. The pTriEx-PDCS and pCI-PDCS constructs were each designed to generate the BHK-21 cell line stably expressing pDC-SIGN and then tested by flow cytometry analysis to estimate the percentage of cells transfected transiently. The results of the pCI-PDCS construct showed approximately 10% to 30% expression (FIG. 3) of pDC-SIGN by transient transfection of the pCI-PDCS plasmid. In sharp contrast, the flow cytometry sorting shown in the upper second panel of FIG. 8a demonstrates more than 95% of the cells in the new constructed cell line expressed pDC-SIGN with the use of pTriEx-PDCS compared to the vector-transfected control. Details of both experiments are described hereinbelow.

It is highly desirable for the process to utilize G418 resistance screening or similar screening techniques known to those of ordinary skill in the art for optimal transfection results and the construction of cells or cell lines stably expressing the proteins of the invention. Suitable cells or cell lines that can be transfected to stably express pDC-SIGN, pICAM-3 and/or pLSECtin, being particularly useful for virus propagation, increasing virus yields and inducing immune responses, especially increasing the immune responses to the porcine antigens, include, but are not limited to, a culture of BHK-21, MARC-145, PK-15, COS-7, VERO, CV-1, LLC-MK2, MDCK, MDBK, Raji B, CHO-K1, 3D4/31, SJPL, IPEC-J2, THP-1, RAW 264.7, ST cells, MA-104, 293T, etc., though preferably the host cell comprises the culture of BHK-21 cells, MARC-145 cells or other dendritic, macrophagic, monocytic, trophoblastic, lymphocytic cell lines and the like, desirably monocyte-derived dendritic cells, interstitial dendritic cells, etc. The novel expression, propagation and related methods described herein makes use of such suitable cell or cell line stably expressing pDC-SIGN or its derived fusion construct that is generated as a viral receptor that would allow virus entry into the host cells. While the terms are used herein interchangeably for purposes of the present invention, the term "host cell" refers to primary cells that are cultured directly from and outside of an animal or person, that is, the host cells of the invention are intended to be on a microscopic or microbial level, and not based on the infection of a whole animal or human. The term "cell" refers to the initial type of isolated cells that do not belong to a host (for example, pig) cell line. The term "cell line" refers to an established cell line representative of a particular cell type.

Figure 11A:
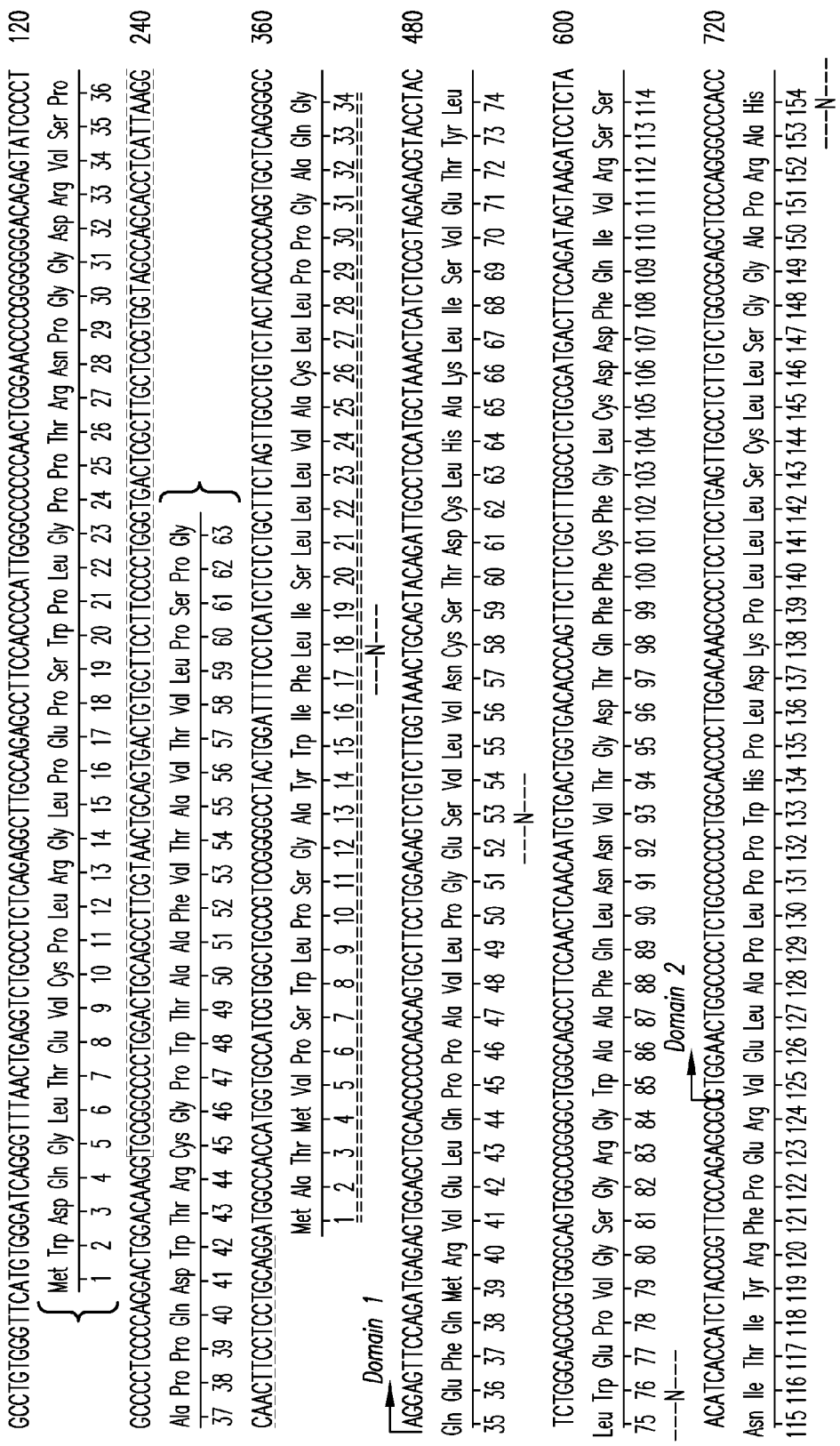

A particularly preferred protein or polypeptide, as the common terms are used interchangeably, embraces the isolated pDC-SIGN polypeptide having the amino acid sequence set forth in SEQ ID NO:2 and FIGS. 2a-2b, the isolated pICAM-3 polypeptide having the amino acid sequence set forth in SEQ ID NO:5 and FIGS. 11a-11b, and the isolated pLSECtin polypeptide having the amino acid sequence set forth in SEQ ID NO:37 and FIGS. 14b-14c. The biologically active variants of the porcine proteins are further encompassed by the invention. One of ordinary skill in the art would know how to modify, substitute, delete, etc., amino acid(s) from the polypeptide sequence and produce biologically active variants that retain the same, or substantially the same, activity as the parent sequence without undue effort.

To produce or express the polypeptide products of the invention, particularly pDC-SIGN, pLSECtin or its fusion protein construct, the process may include the following steps: growing, under suitable nutrient conditions, prokaryotic or eucaryotic host cells transfected with the selected nucleic acid molecule in a manner allowing expression of the polypeptide product or polypeptide fusion product, and isolating the desired polypeptide product of the expression of said nucleic acid molecule by standard methods known in the art. The nucleic acid molecules for transfection include, for example, the nucleotide sequence encoding one or more proteins selected from the group consisting of pDC-SIGN, pICAM-3 and pLSECtin, a complement of at least one of the nucleotide sequences and a functional, defined portion of at least one of the nucleotide sequences, or the fusion protein described herein. It is contemplated that the porcine proteins, fused proteins, etc. of the invention may be prepared by other techniques such as, for example, biochemical synthesis and the like.

Another important embodiment of the present invention is directed to the isolated monoclonal or polyclonal antibodies that are raised against and specifically bind to pDC-SIGN and particularly to the amino acid sequence of SEQ ID NO:2 but also the antibodies raised against pICAM-3 and pLSECtin which would specifically bind to the respective amino acid sequences of SEQ ID NO:5 and SEQ ID NO:37. Preferably, the antibody is polyclonal and the polyclonal antibody specifically binds to the peptide regions comprising SEQ ID NO:13, SEQ ID NO:14 or a combination of SEQ ID NO:13 and SEQ ID NO:14. Also included within the scope of the invention are natural or artificially synthesized oligosaccharide ligands, such as, for example, mannose-, fucose- or galactose-containing oligosaccharides and the like, that specifically bind to pDC-SIGN and particularly to the amino acid sequence of SEQ ID NO:2 or pICAM-3 or pLSECtin as well as the hybridoma cell line that produces the antibodies recognizing pDC-SIGN, pICAM-3 and pLSECtin but desirably pLSECtin or pDC-SIGN. The antibodies, the oligosaccharide ligand and the hybridoma cell lines may be prepared by the methods described herein as well as by standard methods known to those of ordinary skill in the art.

The binding of an oligosaccharide ligand to one or more of the porcine proteins such as pDC-SIGN may be mediated, for instance, by generation of a polypeptide antigen-oligosaccharide complex through a biotin-streptavidin system. First, the polypeptide antigen is chemically coupled to streptavidin. Subsequently, streptavidin-antigen conjugates are linked to oligosaccharide-PAA-biotin via streptavidin-biotin binding. For an in vitro study, a cell line stably expressing the porcine protein such as, for example, pDC-SIGN is incubated with antigen-oligosaccharide conjugates, to investigate the ligand internalization, to confirm its activity and to compare the activation of antigen-specific effector T-cell with that induced by polypeptide only. In addition to oligosaccharide ligands, the anti-pDC-SIGN antibody, anti-pICAM-3 antibody or anti-pLSECTin antibody can be used to cross-link to a polypeptide antigen to target the respective pDC-SIGN, pICAM-3 or pLSECtin receptors. Adding pDC-SIGN-specific oligosaccharide or anti-pDC-SIGN antibody concentrates the antigen to the immature dendritic cells that initiate the immune response.

Basically, the hybridoma cell line of the present invention may be prepared by: Immunization of mice with a porcine protein antigen of this invention and selection of mouse donors for generation of hybridoma cells; screening of mice for antibody production; preparation of myeloma cells; fusion of myeloma cells with immune spleen cells; cloning of hybridoma cell lines by limiting dilution; and expansion and stabilization of clones by ascites production. It is contemplated that the skilled artisan will appreciate how to produce a hybridoma cell line through other routine steps or methods published in the literature.

The present invention further includes a new immunogenic composition and method of using the porcine protein antibodies in which the antigen-specific immune response can be enhanced by targeting pDC-SIGN, pICAM-3 and/or pLSECtin. As used within the context of this invention, "targeting" pDC-SIGN or pICAM-3 means that the immature dendritic cells throughout the body would recognize the immunized antigen-oligosaccharide conjugates or antigen-anti-protein antibody complex by the interaction between ligand (e.g., oligosaccharide or anti-DC-SIGN antibody) and receptor (e.g., DC-SIGN) on dendritic cells, which is more efficient than being immunized with naked antigen. A comparable use of the appropriate antibody complex for targeting the pLSECtin receptor would involve liver cells.

The invention also embraces a novel veterinary composition comprising a nontoxic, physiologically acceptable carrier and an immunogenic amount of the monoclonal or polyclonal antibody described herein in admixture with or covalently attached to an antigen or, alternatively, the carrier with the porcine proteins described herein. Preferably, a conjugate vaccine is used and may be created by standard processes to covalently attach a poor antigen to the antibody acting as a carrier protein, thereby conferring the immunological attributes of the carrier on the attached antigen.

When administered to pigs, the veterinary composition of the invention may contain one or more porcine antigens such as, for example, porcine circovirus type 2 (PCV-2), Porcine Reproductive and Respiratory Syndrome Virus (PRRSV), *Mycoplasma hyopneumoniae, Haemophilus parasuis, Pasteurella multocida, Streptococcum suis, Actinobacillus pleuropneumoniae, Bordetella bronchiseptica, Salmonella choleraesuis, Erysipelothrix rhusiopathiae*, leptospira bacteria, swine influenza virus (SIV), porcine parvovirus, *Escherichia coli*, porcine respiratory coronavirus, rotavirus, a pathogen causative of Adjezky's Disease, Swine Transmissible Gastroenteritis, etc. The compositions of the invention optionally contain a variety of typical, non-toxic, pharmaceutically acceptable carriers, additives, diluents and adjuvants. By way of an illustration, a veterinary composition may be prepared, for example, to contain the anti-peptide polyclonal antibody specific to pDC-SIGN, pICAM-3 or pLSECtin in admixture or conjugated to one or more antigens such as PCV-2 and PRRSV in combination with a suitable carrier, preservative and adjuvant system.

Genetically engineered vaccines, which are desirable in the present invention, are produced by techniques known in the art. Such techniques involve, but are not limited to, further manipulation of recombinant DNA, modification of or substitutions to the amino acid sequences of the DC-SIGN proteins and the like.

The fused protein product of the invention may be made, for example, by fusing the cytoplasmic tail (CT), the transmembrane domain (TMD) and the repeat neck region of human DC-SIGN/L-SIGN with the carbohydrate recognition domain (CRD) of porcine DC-SIGN. By way of illustration, a fusion PCR technique including two rounds of PCR may be performed to generate the desired fusion fragment. In the first-round PCR, the upstream fragment containing the CT, TMD and neck region of human DC-SIGN/L-SIGN obtained from the full-length human DC-SIGN/L-SIGN cDNA is amplified using the human DC-SIGN/L-SIGN cDNA clone with primers P1 and P2, while the downstream fragment containing the CRD of porcine DC-SIGN derived from the full-length porcine DC-SIGN cDNA is amplified with primers P3 and P4. Primers P2 and P3 are reverse-complementary to each other. The two fragments sharing a short stretch (~25bp) at their 3'- or 5'-end are purified and used as the templates for the second-round PCR to amplify the fusion fragment with primers P1 and P4. The second-round PCR product is double-digested with desired restriction enzymes and cloned into an expression vector that is digested with the same restriction enzymes. This fusion PCR technique is further described in S. U. Emerson et al., "In vitro replication of hepatitis E virus (HEV) genomes and of an HEV replicon expressing green fluorescent protein," J. Virol. 78(9):4838-4846 (2004).

To determine that the fragment is active and useful in the present invention, standard ligand-binding and endocytic activity assays may be performed to confirm the potential roles of either part of the fused protein. Typically, the CRD (carbohydrate recognition domain) part of the fusion protein isolated from the pDC-SIGN or pLSECtin cDNA is responsible for the recognition and capture of the porcine pathogen verifiable by the ligand-binding assay, while the CT (cytoplasmic tail), TMD (transmembrane domain) and repeat neck region of the fusion protein that is derived from the hDC-SIGN, hLSECtin or hL-SIGN is responsible for uptake of the captured pathogen into the cells by endocytosis, which can be substantiated by the endocytic activity assay.

The invention includes a new method of conferring passive immunity against an antigen (i.e., a pathogen acting as an immunogen) in an animal by effectively inducing naïve and recall T-cell responses which comprises administering to the animal an immunologically effective amount of the veterinary composition as described herein. The method, which provides an antigen-specific immune response against the antigen or pathogen, is preferentially designed to enhance the immunogenic activity of a weak antigen or pathogen by targeting pDC-SIGN, pICAM-3 or pLSECtin. In this regard, the covalent vaccine product is particularly useful. The poor antigen or immunogenic substance requiring enhanced immunological potency from the antibody composition comprises a virus, a bacterium, a fungus or a parasite. The antibody of the invention provides enhanced entry of the pathogen at cell receptor sites, aids in the inducement of an immune response and ultimately in the prevention of disease transmission. Preferably, the animal requiring the immunogenic enhancing composition is a pig but it is foreseen that other animals such as bovine or canine may benefit as well.

In the method, an immunologically effective amount of the composition of the present invention is administered to animals, particularly young piglets, in need of protection against disease or infection in order to induce a protective immune response in the animals. Targeting pDC-SIGN, pICAM-3 or pLSECtin produces an enhanced immune response in the animal. An effective immunizing amount is one in which a sufficient immunological response is attained to protect the animal from the harmful effects of the pathogen. A protective immune response is considered to be obtained when the veterinary composition is able to protect at least a significant number of the inoculated animals as required by standard values in the vaccine field. The immunologically effective dosage or the effective immunizing amount that inoculates the animal and elicits satisfactory vaccination effects can be easily determined or titrated by routine testing such as standard titration studies.

The novel immunogenic composition of the present invention is employed for the vaccination of healthy animals, preferably piglets at approximately three months of age. The vaccine may also be given to mature or adult animals such as sows (i.e., older than three months) prior to breeding. The vaccine can be administered in a single dose or in repeated doses if antibody titers decline and a booster shot is deemed necessary. Desirably, the vaccine is administered to healthy animals in a single inoculation to provide long term protection against disease, protecting the animals for at least one year to three years or longer. Appropriate dosages are determined by standard dose titration studies.

The present invention also includes a unique method of cloning an unknown DC-SIGN cDNA homologue from a non-primate large animal species which comprises the following steps: (a) isolating and in vitro culturing monocyte-derived dendritic cells from the venous blood of the animal in a suitable host cell under suitable nutrient conditions that allow growth of said dendritic cells; (b) extracting RNA; (c) performing reverse transcriptase (RT) and PCR using degenerate primers designed to be complementary to conserved sequences in human and mouse DC-SIGN nucleotide sequences based on multiple sequence alignments of the nucleic acid molecules encoding human and mouse DC-SIGN in order to synthesize a first-strand of cDNA and amplify by RT-PCR a short fragment having a sequence homologous to human DC-SIGN; (d) performing reverse transcriptase and RACE-PCR on the short fragment using gene-specific primer PDR-1 comprising SEQ ID NO:9 and gene-specific primer PDF-1 comprising SEQ ID NO:10 designed for 5'-RACE or 3'-RACE, respectively, and based on the sequence information from degenerate PCR products; (e)

cloning the two overlapping fragments of the complete cDNA of the unknown DC-SIGN homologue in the animal by rapid amplification of cDNA ends (RACE)-PCR reaction products; and (f) isolating, purifying or sequencing the DC-SIGN homologue of the animal.

In the above cloning method, the suitable host cell includes, but is not limited to, a culture of CD14 positive peripheral blood monocyte cells (PBMC), spleen-derived lymphocytes, bone-marrow-derived lymphocytes and the like. Preferably, the host cell in the new cloning method uses the culture of CD14 positive PBMC.

As one example of the cell passage phase, cells stably expressing DC-SIGN are grown to the monolayer as observed by the light microscope. Cells are passaged every 3 to 4 days as needed for virus inoculation. Cell growth medium, for example, Dulbecco's Modified Eagle's Medium (DMEM) enhanced with 10% fetal bovine serum (FBS) and 1× antibiotics (10,000 units/mL penicillin G, 10,000 mg/mL streptomycin), is removed from each flask and cells are incubated with 1 mL of a proteolytic enzyme such as trypsin-EDTA (TE). TE is removed upon the first indication of cell detachment. Five milliters of cell growth medium is added to suspend cells; the suspension is aspirated and split over five flasks. Seven milliliters of cell growth medium is added to each flask and subsequently aspirated. Flasks are transferred to a humidified incubator (37° C., 5% CO2) and incubated in the horizontal position for cell growth. Flasks are inoculated with viruses (for example, PRRSV) or used for further cell passage when 90% confluence is observed.

As an example of virus culture, the 10% FBS-DMEM/PS cell growth medium is removed; and cells are inoculated with 1 mL virus stock with appropriate titration. Flasks are incubated horizontally for 1 h (37° C., 5% CO2). Nine milliliters of virus medium (2% FBS-DMEM without antibiotics) is then added to each flask and flasks are returned to the humidified incubator for 2 to 3 days. Virus culture continues until most of the cells show visible signs of cytopathic effect (CPE) under a light microscope. When CPE is observed, the cell culture is terminated by freezing to −80° C. Two more consecutive freeze/thaw cycles from −80° C. to room temperature are performed to lyse the cells and release intracellular virions. The resulting virus stock solution is titrated and frozen at −80° C. until use for process development or virus inoculation for further processing to manufacture virus vaccines.

With respect to the DC-SIGN gene, this invention describes the cloning of the pDC-SIGN cDNA for the first time and, in effect, the first report on cloning the DC-SIGN cDNA homologue (of hDC-SIGN) from a non-primate large animal species. Since there was no relevant sequence available in the Swine Genome Sequencing Project (SGSP) database, this invention used an entirely different and novel strategy to clone the porcine DC-SIGN gene compared to that previously used for mouse SIGNR molecules. Porcine MDDCs are generated in vitro and the total RNA extracted from the MDDC cells are used to clone the porcine DC-SIGN homologue. By using degenerate primers based upon human and mouse DC-SIGN sequences, a 210-bp fragment with sequence homologous to the hDC-SIGN and mouse DC-SIGNR was firstly amplified by RT-PCR. Based upon this initial sequence, the complete cDNA sequence of the porcine DC-SIGN was subsequently obtained in two overlapping fragments by 5'- and 3'-RACE-PCR, respectively. In addition, the complete pDC-SIGN gene was uniquely cloned based upon the cDNA sequence by one-step genomic PCR. The cloning strategy employed herein will be very useful for the identification of the DC-SIGN homologues in other animal species with no available sequence information.

Although the porcine DC-SIGN was cloned from porcine MDDCs, pDC-SIGN could not be amplified from the original purified CD14-positive PBMCs, suggesting that the expression of pDC-SIGN was activated during the development of MDDCs.

For the mouse SIGNR members, only SIGNR3 shares the ability with hDC-SIGN to bind both high-mannose and fucose-containing glycans (Powlesland et al., 2006, supra). SIGNR2 binds almost exclusively to GlcNAc-terminated glycans, and SIGNR7 binds preferentially to the 6-sulfo-sialyl Lewis$^x$ glycan, similar to some members of the siglec family of sialic acid-binding receptor that selectively recognize sialic acids (id.). The pDC-SIGN identified herein has all nine conserved residues involved in calcium-dependent carbohydrate binding in the CRD.

However, although the sequence alignment results suggest that pDC-SIGN probably has distinct carbohydrate binding specificity from hDC-SIGN and L-SIGN, because of the lower sequence homology compared to other DC-SIGN-related proteins, they do share the analogous ligand-binding capacity with hDC-SIGN. This is mainly because both of the porcine and bovine DC-SIGN proteins have all structural conserved residues facilitating in the proper folding of the CRD and involved in calcium-dependent carbohydrate binding. On the other hand, these interactions may involve protein-protein interaction in addition to protein-carbohydrate interaction, which has been implicated by the scanning-mutagenesis analysis of hDC-SIGN binding to hICAM-2 and hICAM-3 (S. V. Su et al., "DC-SIGN binds to HIV-1 glycoprotein 120 in a distinct but overlapping fashion compared with ICAM-2 and ICAM-3," J. Biol. Chem. 279:19122-32 (2004)). Furthermore, it was previously shown that hDC-SIGN has a distinct but overlapping binding fashion for gp120 and ICAM-3 (T. B. Geijtenbeek et al., "Identification of different binding sites in the dendritic cell-specific receptor DC-SIGN for intercellular adhesion molecule 3 and HIV-1," J. Biol. Chem. 277:11314-11320 (2002); Su et al., 2004, supra). A single mutation from valine to glycine at aa position 351 in hDC-SIGN abrogated ICAM-3 binding but not HIV-1 gp120 interaction (Geijtenbeek et al., 2002, supra). However, the binding to either ICAM-3 or ICAM-2 was unaffected when valine was mutated to alanine (Su et al., 2004, supra). The pDC-SIGN protein has the histidine residue at position 204 that is uniquely shared by the bovine, canis and equine DC-SIGN proteins. The change from valine to histidine likely has minimal effect on pDC-SIGN-hICAM-3/hICAM-2 interaction.

It has been shown that recognition of small carbohydrate compounds by individual CRD alone is not sufficient to achieve the high-affinity interactions of DC-SIGN and L-SIGN with pathogens like HIV-1 gp120. Biochemical studies with repeat domain deletion mutants in the neck region also showed that a minimum of three repeats are required to form tetramers, and that additional repeats would stabilize the tetramer (G. A. Snyder et al., "The structure of DC-SIGNR with a portion of its repeat domain lends insights to modeling of the receptor tetramer," J. Mol. Biol. 347:979-989 (2005)). The pDC-SIGN newly identified in the present invention, along with the known bovine, canis and equine DC-SIGN proteins, did not have repeat sequences in the neck region, suggesting that these proteins including the porcine DC-SIGN may be unable to form a tetramer, and thus support the statement that porcine DC-SIGN has a distinct carbohydrate binding specificity.

This is not directly associated with the binding capacity of these proteins since it is now shown that pDC-SIGN is capable of effectively interacting with potential ligands like hICAM-3 and hICAM-2, and capture and transmit PRRSV to the target cells. Similarly, bovine DC-SIGN without repeat sequences in the neck region also has the ability to bind and internalize HIV-1 gp120 as well as *Mycobacterium bovis* BCG (Y. Yamakawa et al., "Identification and functional characterization of bovine orthologue to DC-SIGN," J. Leukoc. Biol. 83:1396-403 (2008)). Another example is the hDC-SIGN-related lectin LSECtin, which is devoid of repeat sequences in the neck region, and yet it is still able to mediate antigen capture and pathogen binding by human myeloid cells (A. Dominguez-Soto et al., "The DC-SIGN-related lectin LSECtin mediates antigen capture and pathogen binding by human myeloid cells," Blood 109:5337-45 (2007)). Although pDC-SIGN is not involved in PRRSV entry, it is shown herein that pDC-SIGN can enhance the in trans virus transmission from the engineered BHK donor cells to target MARC-145 cells despite the fact that both of these two cell lines are not of pig origin.

The binding of pDC-SIGN expressed on the cell surface to soluble hICAM ligands is also demonstrated herein. Improving the binding of hICAM-2 to pDC-SIGN or blocking the binding of hICAM-3 to pDC-SIGN may have therapeutic value. In particular, in vivo cell-cell adhesion interactions may have important implications for clinical applications of pig-to-human xenotransplantation since recipient T cells mediate xenograft rejection. Furthermore, the tissue and cellular location and the property of pDC-SIGN and its cross-binding to human natural ligands strongly implicate analogous physiologic roles for this lectin in cell adhesion. Similar roles for pLSECtin and pICAM-3 are also contemplated.

A surprising finding from the study was that pDC-SIGN is most closely related to mouse SIGNR7 and SIGNR8 than to other mouse SIGNR members. The discovery of eight DC-SIGN homologues in mouse specie indicated they had a widely divergent biochemical and physiological properties (Powlesland et al., 2006, supra). However, none of them were experimentally verified to be the functional orthologue to human DC-SIGN. While the mouse DC-SIGN proteins have not been found to share functions with the human proteins, bovine DC-SIGN was recently shown to express on bovine MDDCs, bind and internalize HIV-1 gp120 as well as *Mycobacterium bovis* bacillus Calmette-Guerin (BCG), suggesting that it is functionally related to hDC-SIGN (Y. Yamakawa et al., "Identification and functional characterization of bovine orthologue to DC-SIGN," J. Leukoc. Biol. 83:1396-403 (2008)), even though they are classified into two different evolutionary pathway. This conclusion is also supported by the evidence of tissue and cellular distribution and binding characteristics of pDC-SIGN with hICAM ligands in the below experiments.

Figure 7:
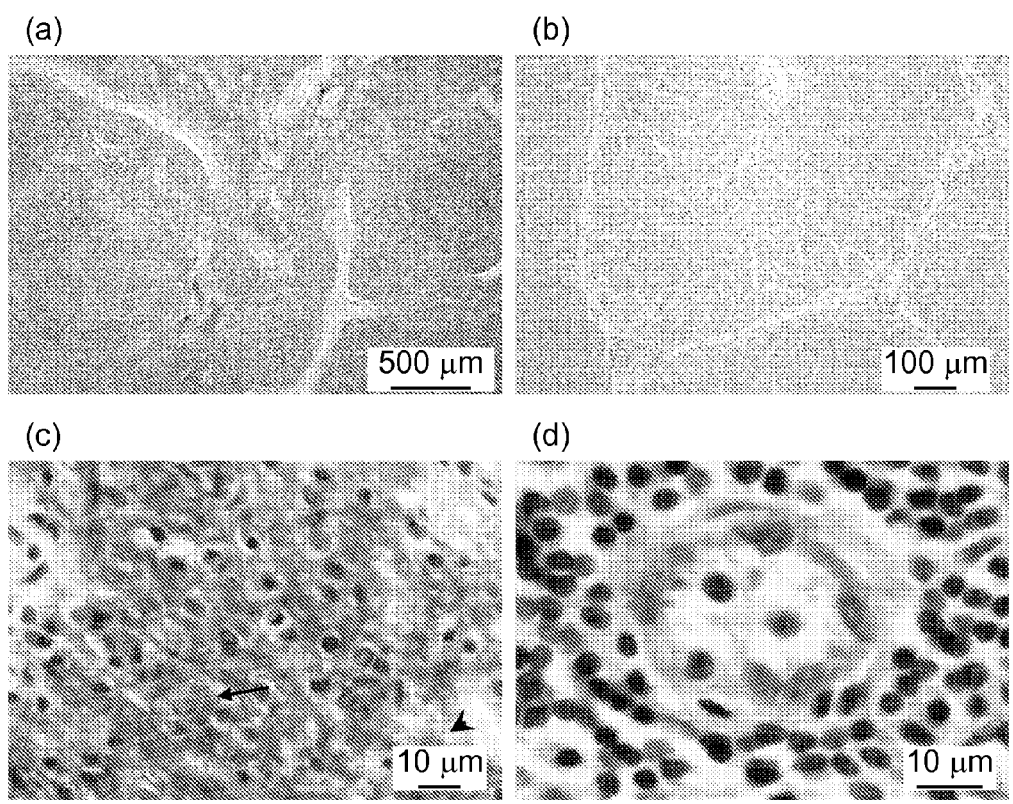
FIG. 7 illustrates the detection of pDC-SIGN protein expression by immunohistochemistry (IHC) in pig lymph node tissues but not in pig liver tissues. Localization of pDC-SIGN protein expression was examined by IHC using ABC method on paraffin sections of pig lymph nodes (a, c, d) and pig livers (b).

In the details of this invention, it is shown that pDC-SIGN mRNA expression is mainly distributed in various lymphoid organs and the protein expression is not detected on the surface of $CD14^+$ monocytes or PBL. Porcine DC-SIGN is not only expressed on MDDCs but also on MDMΦs and PAM, suggesting that it is activated during the development of porcine DCs and macrophages. By using IHC analysis, it is further confirmed that pDC-SIGN was expressed on lymph node sinusoidal APCs including macrophage-like and dendritic-like cells but not on B or T lymphocytes (FIG. 7). Porcine DC-SIGN expression was also detected on lymph node endothelial cells, which shares an analogous pattern with that of hDC-SIGN expression (J. H. Martens et al., "Differential expression of a gene signature for scavenger/ lectin receptors by endothelial cells and macrophages in human lymph node sinuses, the primary sites of regional metastasis," J. Pathol. 208:574-89 (2006)). However, neither pDC-SIGN mRNA nor protein was detectable in pig liver tissues using RT-PCR and IHC analysis, respectively.

Based on these results, it is concluded that the cloned porcine gene is the DC-SIGN homologue (instead of the L-SIGN homologue) although the amino acid sequence of pDC-SIGN does not show significant sequence identity with hDC-SIGN or hL-SIGN. The L-SIGN genes emerged from a duplication event in the common DC-SIGN ancestor of anthropoids and probably does not exist in non-primate mammalian species as shown on the bovine, canis and equine genomic regions where the C-type lectins arrange as a three gene cluster CD23/LSECtin/DC-SIGN instead of a four gene cluster CD23/LSECtin/DC-SIGN/L-SIGN on human chromosome 19p13.3. The evolutionary pathway of DC-SIGN homologues in these non-primate mammalian species is distinct from that in primates resulting in the existence of DC-SIGN as a single gene. Phylogenetic analysis and comparison of gene organization indicated that porcine DC-SIGN is highly related to these non-primate mammalian species and thus should share the same characteristics. Furthermore, the absence of pDC-SIGN expression in pig livers by IHC and RT-PCR also supports this conclusion, since, if the cloned pDC-SIGN were the porcine L-SIGN homologue, its RNA and protein expression should have been detected in liver tissues by RT-PCR and IHC, respectively.

The transmembrane property of porcine DC-SIGN protein is confirmed by experimental evidence in relation to this invention and determined to function as an adhesion receptor on porcine DCs.

Figure 4A:
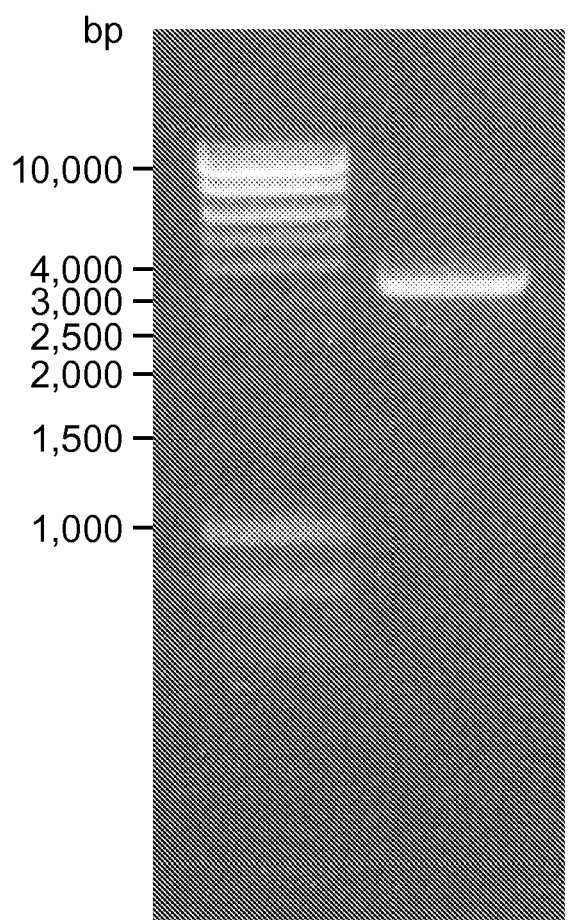
Figure 4B:
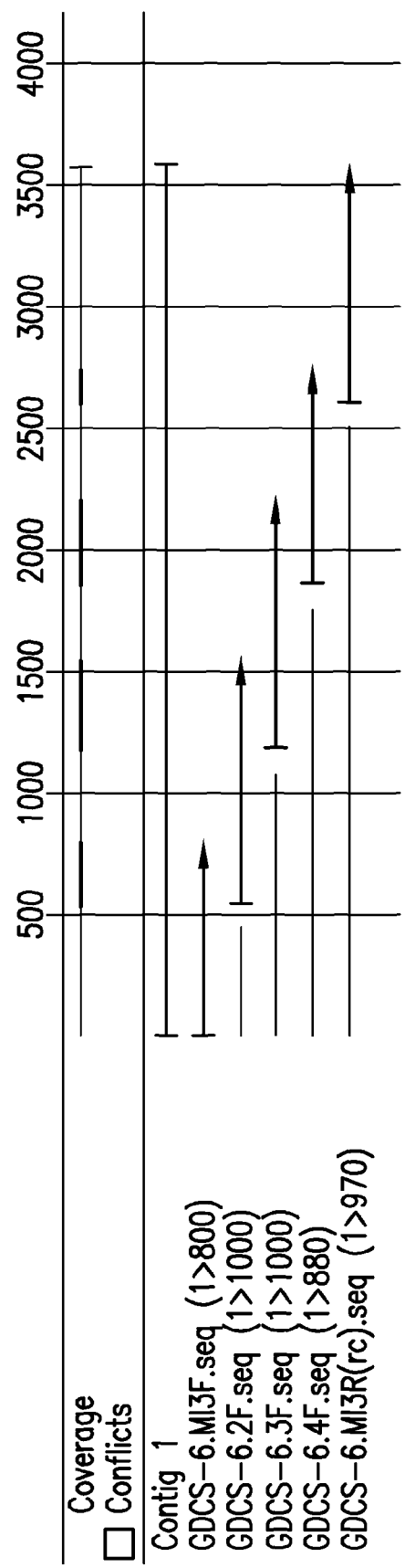
Figure 5B:
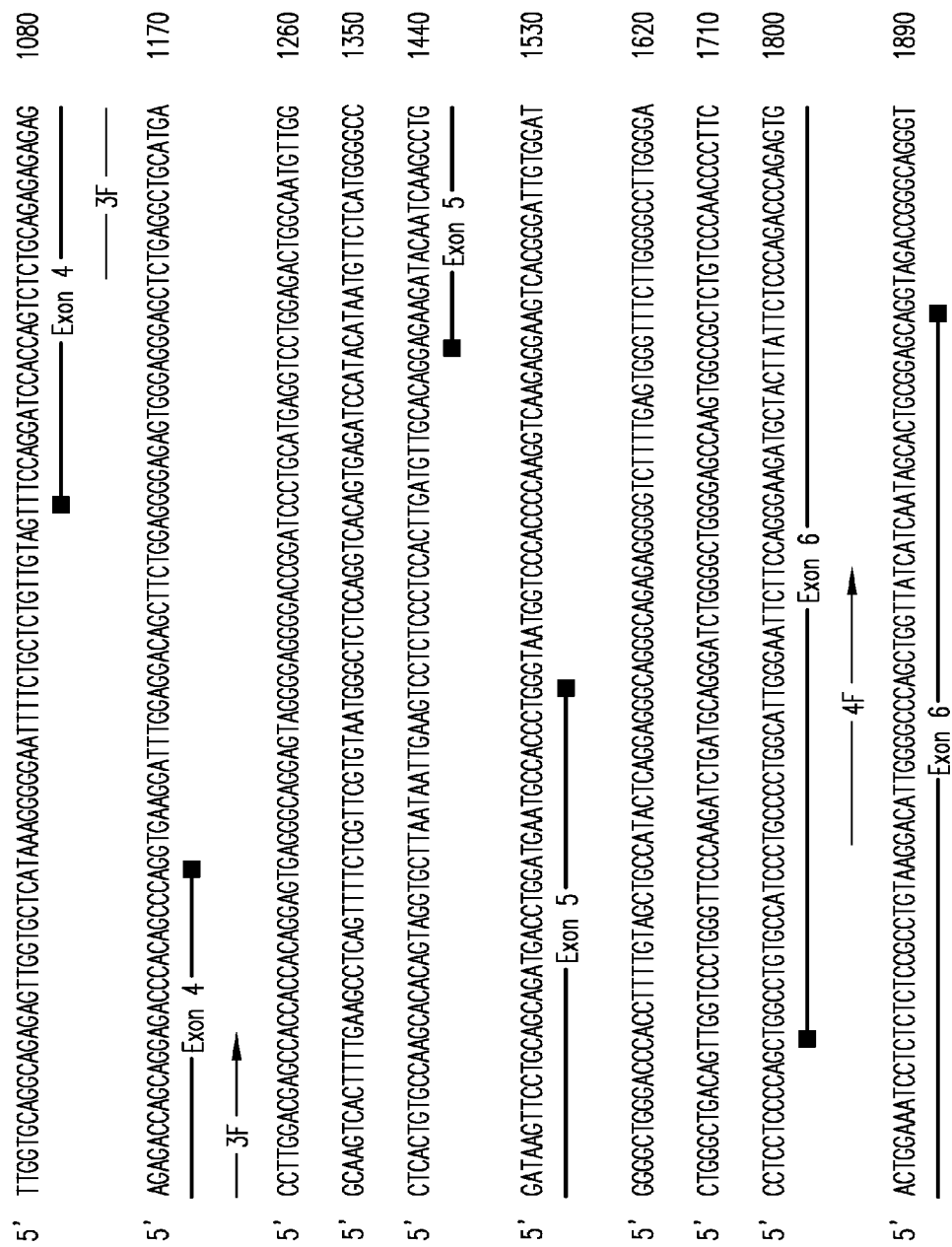
Figure 5D:
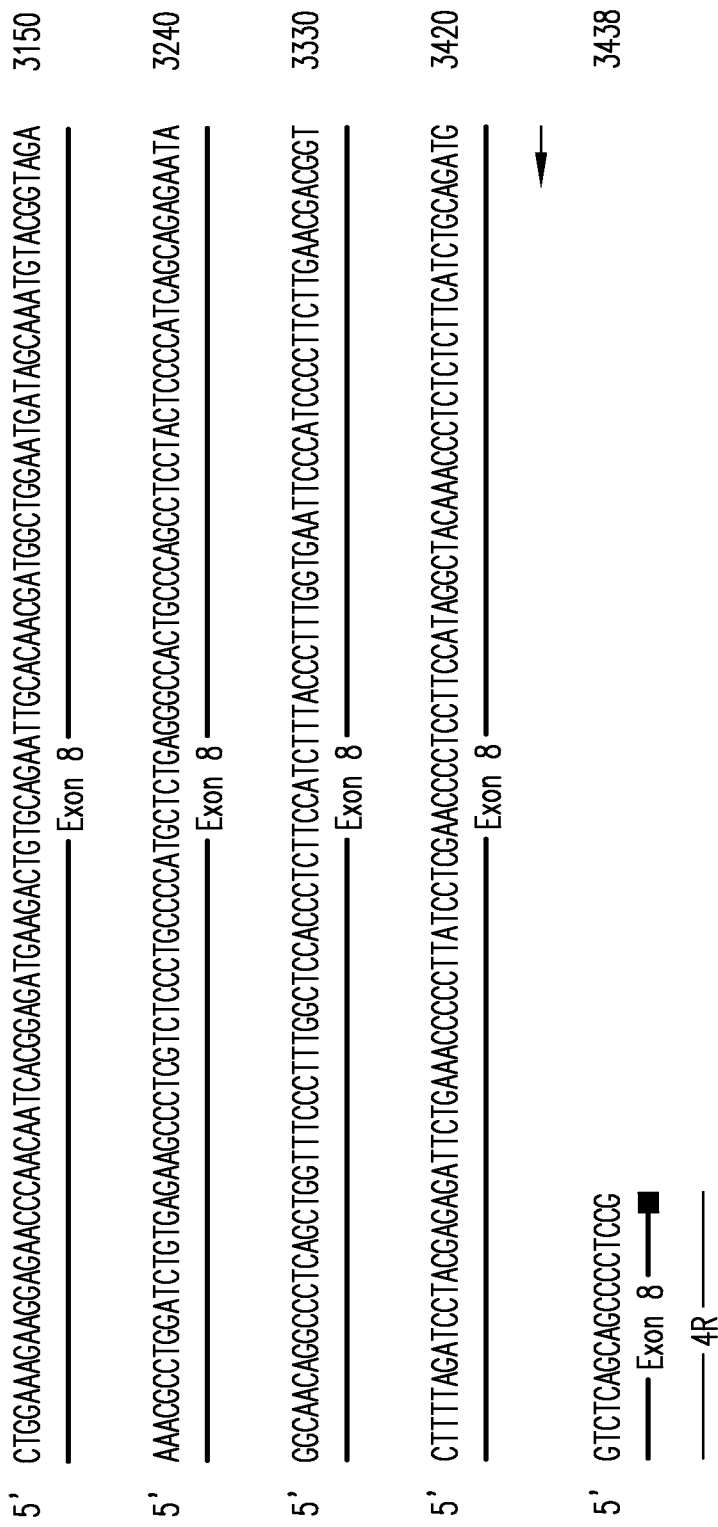

To better characterize the expression of porcine DC-SIGN, determination of the gene in the genomic DNA level was needed. Based on the terminal sequence of the determined porcine DC-SIGN cDNA, the porcine DC-SIGN gene that has not yet been released in GenBank and other pig genomic sequence resources to date was also amplified and cloned by using genomic PCR (FIG. 4). The consensus sequence of the porcine DC-SIGN gene is 3438 by in length, encoding eight exons spanning the complete coding region of the gene in which exons 1 and 8 had unknown size (FIGS. 5a-5d). The intron sizes vary from 113 to 689 by and all acceptor and donor sequences on the introns conform to the GT-AG rule. Additional alternatively spliced mRNA isoforms were not predicted by the computer program, suggesting that the identified cDNA from porcine monocyte-derived dendritic cells is likely the only existing isoform of the porcine DC-SIGN expression, which is consistent with the RACE-PCR result described above (FIG. 1(c)).

Examining the tissue and cellular distribution of pDC-SIGN, it was found that the expression of pDC-SIGN mRNA was detected in both of the primary (thymus and bone marrow) and the secondary lymphoid organs (lymph node and spleen) as well as lung and skeletal muscles but not in duodenum, kidney, heart or liver of pig by RT-PCR (FIG. 6a). The expression level in lymph node and bone marrow was the highest. The detection of DC-SIGN expressed in muscles was intriguing.

Figure 6B:
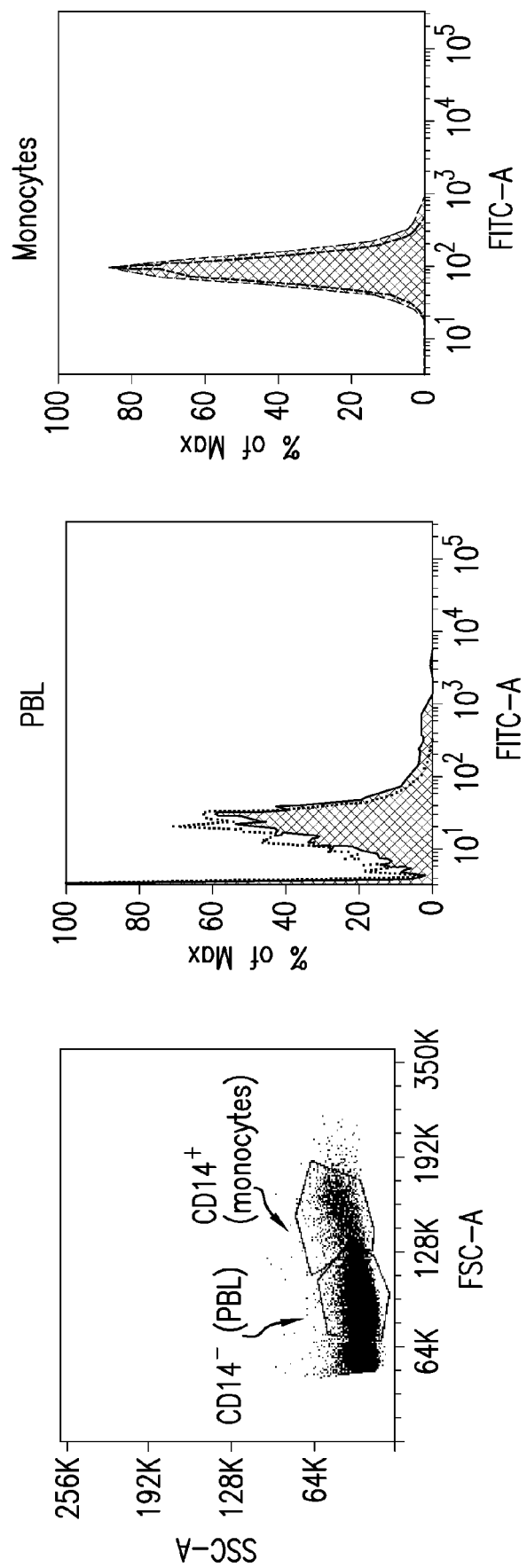
Figure 6C:
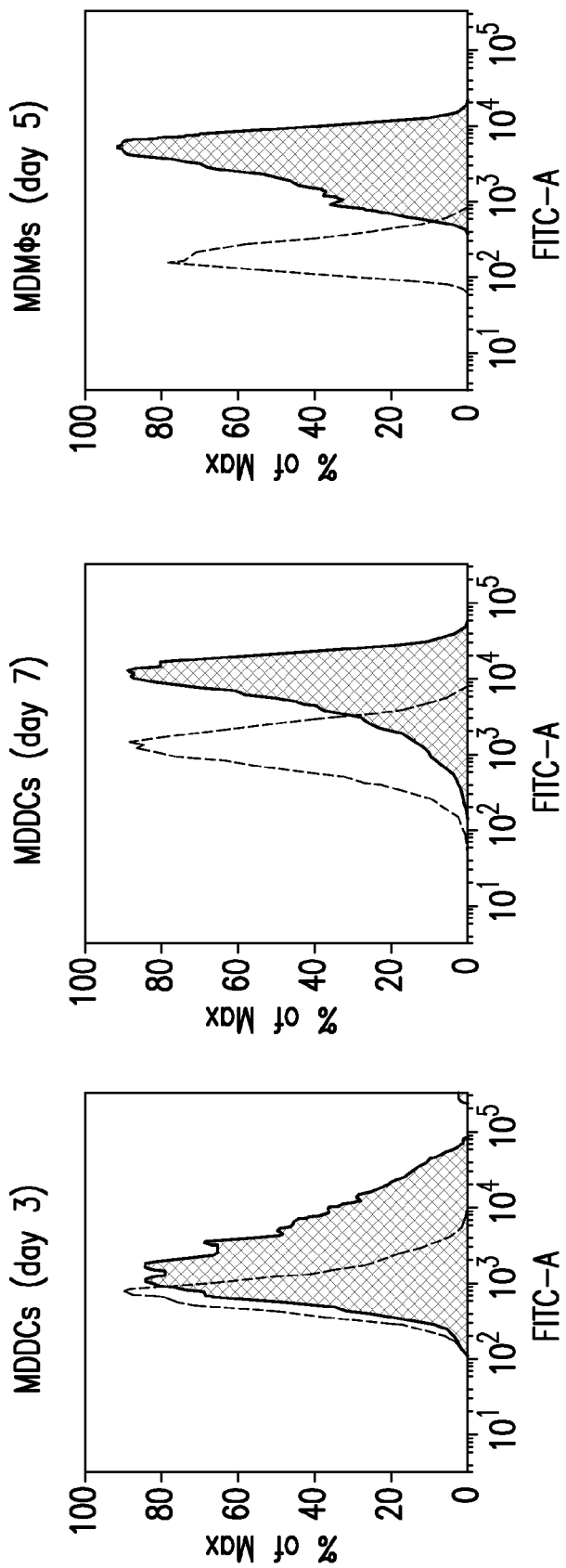
Figure 6D:
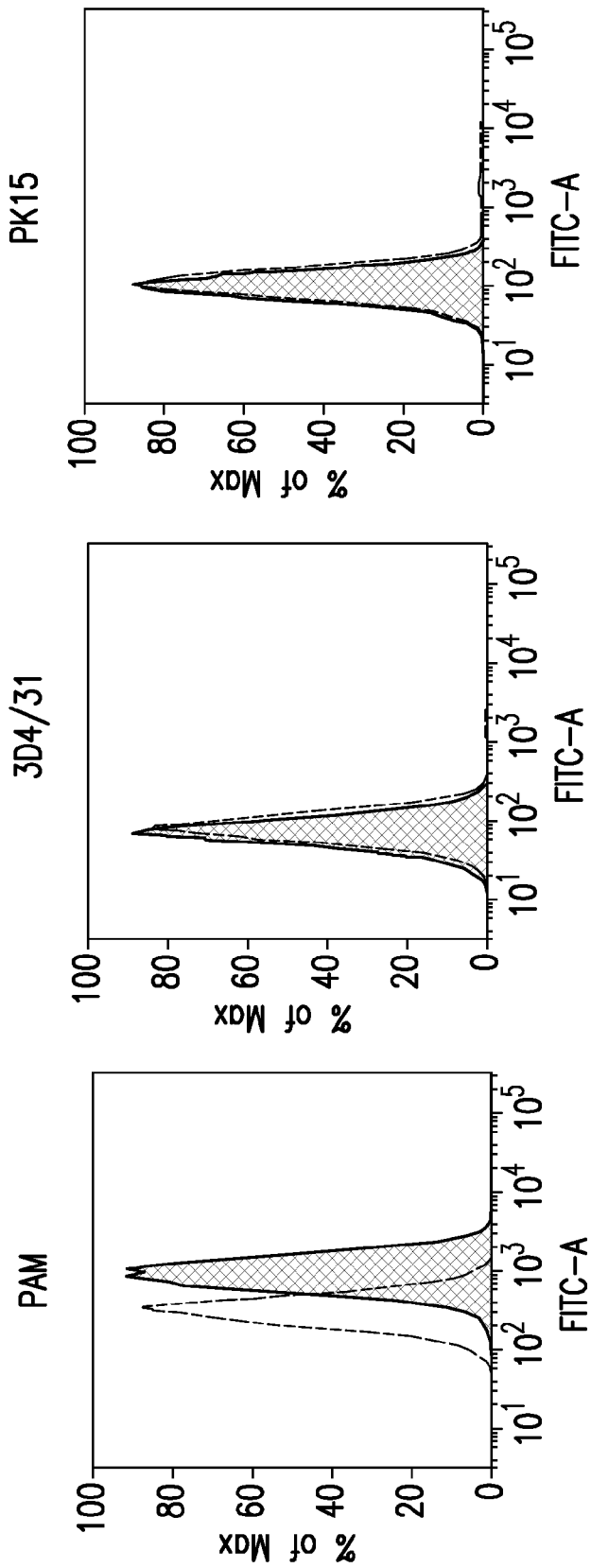

Taking pDC-SIGN expression in various lymphoid organs into account, it was speculated that pDC-SIGN may be also expressed by specific hematopoietic cell populations in addition to MDDCs. Therefore, flow cytometry analysis was performed to detect the surface expression of pDC-SIGN protein on PBL, monocytes, MDDCs, MDMΦs and PAM (FIGS. 6b to 6d). Scatter profile of porcine PBMC clearly indicated two cell populations, PBL and monocytes according to their morphology. Since CD14 molecule is the surface marker for porcine monocytes (H. W. Ziegler-Heitbrock et al., "The antibody MY4 recognizes CD14 on porcine monocytes and macrophages," Scand. J. Immunol. 40:509-14 (1994)), these two cell populations could be separated by immunomagnetic labeling MACS system using anti-porcine CD14 monoclonal antibody. CD14+ monocytes were further used to develop MDDCs with the addition of rpGM-CSF and rpIL-4 or MDMΦs in the absence of the cytokines, respectively. PBL and the monocytes did not show any pDC-SIGN expression, which was expected since hDC-SIGN or L-SIGN is not expressed on lymphocytes or monocytes. Accordingly, there was no detectable pDC-SIGN expression on a porcine monocytic cell line 3D4/31 (FIGS. 6b to 6d). Upon differentiation of the monocytes into MDDCs in culture, the pDC-SIGN expression was up-regulated with an approximately 8-fold increase of median fluorescence intensity from day 3 to day 7. Porcine DC-SIGN expression was also found on MDMΦs. Compared to MDDCs, the majority of MDMΦs gave a pDC-SIGN phenotype. PAMs were also dominated by a pDC-SIGN phenotype, but the expression level was lower than that on MDMΦs. In accordance with undetectable expression of pDC-SIGN mRNA in pig kidney, the protein was not expressed in an epithelial cell line PK15 derived from pig kidney (FIGS. 6b to 6d).

To further confirm whether pDC-SIGN protein was indeed expressed in particular cell populations of lymphoid tissue, IHC analysis on paraffin sections of pig lymph node and liver tissues was performed. It was found that pDC-SIGN protein showed a predominant sinusoidal pattern of expression in lymph nodes (FIG. 7(a)). However, there was no detectable expression in pig livers (FIG. 7(b)), which was consistent with the RT-PCR results (FIG. 6a). Most of the cells immunostained with pDC-SIGN-specific anti-peptide antibody in sinuses of lymph nodes were macrophage-like and dendritic-like cells (FIG. 7(c)). Endothelial cells in lymphatic vessel of parenchyma were also immunostained with pDC-SIGN-specific anti-peptide antibody (FIG. 7(d)). The expression pattern of pDC-SIGN protein in pig lymph nodes is analogous to that of hDC-SIGN in human lymph nodes where hDC-SIGN protein was identified not only on sinusoidal macrophages but also on endothelial cells by IHC (J. H. Martens et al., "Differential expression of a gene signature for scavenger/lectin receptors by endothelial cells and macrophages in human lymph node sinuses, the primary sites of regional metastasis," J. Pathol. 208:574-89 (2006)). The absence of pDC-SIGN expression in pig livers further supported that the cloned pDC-SIGN is not the L-SIGN homologue since the presumed porcine L-SIGN, if exists, should be strongly expressed on LSECs.

In a separate embodiment of the present invention, two new cDNA isoforms of porcine ICAM-3 have now been identified from in vitro cultured porcine monocyte-derived dendritic cells (the nucleotide sequence encoding the larger pICAM-3 isoform corresponds to SEQ ID NO:4 while the smaller nucleotide sequence encoding a smaller pICAM-3 isoform corresponds to SEQ ID NO:39). The smaller of the two isoforms contains a 114-nt deletion in the noncoding region. Intercellular adhesion molecule-3 (human ICAM-3, LD50) is a member of the immunoglobulin (Ig) superfamily that binds both leukocyte integrin LFA-1 (CD11a/CD18) and dendritic cells-specific intercellular-adhesion-molecule-3 (ICAM-3)-grabbing nonintegrin (human DC-SIGN, CD209). ICAM-3 plays important roles in activation of both T lymphocytes and dendritic cells.

Unexpectedly, both of the newly discovered isoforms encode only three Ig-like domains (D1-D3) and lack Ig-like domains 4 and 5 (D4-D5), which is different from human ICAM-3 with five Ig-like domains (D1-D5). The absence of D4 and D5 in porcine ICAM-3 is likely due to continuous skipping of exons 5 and 6 of porcine ICAM-3 gene during the pre-mRNA splicing process. After determining the remaining unknown 3'-proximal region of porcine ICAM-3 genomic DNA sequence, it was found that there exists one in-frame 3-nt nonsense mutation in exon 5 and four in-frame nonsense mutations in exon 6, which are unique in swine specie. A point mutation (G to A) at the putative splice donor site of intron 6 was also identified. Thus, the generation of the porcine ICAM-3 isoforms lacking D4 and D5 is likely caused by nonsense-associated altered splicing (NAS), which is specie-associated and excludes exons 5 and 6 during the pre-mRNA splicing process.

The following examples demonstrate certain aspects of the present invention. However, it is to be understood that these examples are for illustration only and do not purport to be wholly definitive as to conditions and scope of this invention. It should be appreciated that when typical reaction conditions (e.g., temperature, reaction times, etc.) have been given, the conditions both above and below the specified ranges can also be used, though generally less conveniently. The examples are conducted at room temperature (about 23° C. to about 28° C.) and at atmospheric pressure. All parts and percents referred to herein are on a weight basis and all temperatures are expressed in degrees centigrade unless otherwise specified.

A further understanding of the invention may be obtained from the non-limiting examples that follow below.

EXAMPLE 1

Cloning and Characterization of Porcine DC-SIGN cDNA and Gene

Materials and Methods

Pigs: Venous blood samples and porcine alveolar macrophages (PAM) were collected from healthy crossbred conventional pigs of 3 to 7 weeks of age. Pigs were maintained in an isolated room under experimental conditions.

Isolation and culture of porcine alveolar macrophages, porcine peripheral blood lymphocytes, monocytes, monocyte-derived dendritic cells and monocyte-derived macrophages: Porcine alveolar macrophages (PAM) were collected by lung lavage using cold PBS and resuspended in DMEM supplemented with 10% fetal bovine serum (FBS). Fresh or 3-day in vitro cultured PAM cultures were used for staining and subsequent analysis.

Porcine heparinized blood was diluted 1:2 with phosphate-buffered saline (PBS) and centrifuged over Ficoll-Paque PREMIUM (GE Healthcare, Sweden) at 1000 g for 40 min at room temperature. The buffy coat layer containing peripheral blood mononuclear cells (PBMC) was isolated and washed three times with PBS at 250 g for 10 min at 4° C. CD14-positive monocytes on the surface of PBMC were sorted by immunomagnetic labeling MACS system of cells using anti-CD14 mAb (M-M9, VMRD Inc., Pullman, Wash., USA) and goat anti-mouse IgG1-magnetic microbeads (Miltenyi Biotec GmbH, Bergisch Gladbach, Germany). CD14-negative cells, based on the cell morphology determined by flow cytometry analysis, were recognized as porcine peripheral blood lymphocytes (PBL). Purified monocytes were resuspended at 1×10⁵ cells/mL in Dulbecco's modified Eagle's medium (DMEM) supplemented with 10% heat-inactivated fetal bovine serum (FBS), 55 µmol/L of β-mercaptoethanol and antibiotics. Monocytes were then cultured in 6-well plates or 60-mm Petri dishes at 37° C. in the presence of 25 ng/mL of recombinant porcine granulocyte-macrophage colony stimulating factor (rpGM-CSF, R&D Systems, Minneapolis, Minn.) and 25 ng/mL recombinant porcine interleukin-4 (rpIL-4, Endogen, Rockford, Ill.). Half of the culture medium was replaced by fresh medium every 3 days. Cells were observed for characteristic morphology of DC's. The cells were collected on the third or seventh day and used as monocyte-derived dendritic cells (MDDCs). Monocyte-derived macrophages (MDMΦs) were developed in a similar procedure, but cultured in the absence of the two cytokines Cells were collected on the fifth day and used as MDMΦs.

Culture of continuous cell lines: A baby hamster kidney fibroblast cell line BHK-21, a monkey kidney cell line MARC-145 and a porcine kidney epithelial cell line PK15 were grown in MEM supplemented with 10% FBS and antibiotics at 37° C. in an incubator while a porcine monocytic cell line 3D4/31 (ATCC CRL-2844) was grown in RPMI 1640 medium supplemented with 10% FBS and antibiotics at a 37° C. incubator. A mouse fibroblast NIH 3T3 cell line stably expressing hDC-SIGN was obtained through the NIH AIDS Research and Reference Reagent Program (Germantown, Md.) and was renamed as 3T3-HDCS in this study. This cell line was cultured in DMEM supplemented with 10% FBS.

RNA extraction, reverse transcription (RT) and degenerate PCR and rapid amplification of cDNA ends (RACE)-PCR: In vitro cultured porcine monocyte-derived dendritic cells (MDDCs), derived from porcine monocytes in the presence of rpGM-CSF and rpIL-4, were collected between the seventh and tenth days. Total RNA was isolated from MDDCs using the RNeasy mini kit (Qiagen Inc., Valencia, Calif.) followed by an RNase-free DNase I treatment. First-strand cDNA was synthesized from total RNA with SuperScript II reverse transcriptase (Invitrogen Corporation, Carlsbad, Calif.) using oligo-dT (Promega Corporation, Madison, Wis.) as the reverse primer. Several pairs of degenerate primers complementary to conserved sequences in human and mouse DC-SIGN genes were designed based on the multiple sequence alignments of the available human and mouse DC-SIGN related genes. PCR with degenerate primers was performed in 50 µL reaction with an Advantage 2 PCR kit (Clontech, Palo Alto, Calif.) using the following PCR parameters: 94° C. for 2 min, 30 cycles of 94° C. for 15 sec, 57.5° C. for 30 sec and 72° C. for 1 min, and a final incubation at 72° C. for 3 min. A PCR fragment was amplified only when one set of primers (NF-05 and NR-05, Table 1 below) was used for amplification. The obtained PCR products were directly sequenced and compared with the GenBank sequences of the human and mouse DC-SIGN related genes. RT and RACE-PCR were performed with a SMART RACE cDNA amplification kit (Clontech, Palo Alto, Calif.) according to the manufacturer's manual. The gene-specific primers used for 5'-RACE or 3'-RACE were PDR-1 and PDF-1, respectively (Table 1), which were designed based on the sequence information obtained from degenerate PCR products. The RACE reaction products were cloned into a pCR2.1 vector (Invitrogen Corporation, Carlsbad, Calif.) by TA cloning strategy and sequenced.

TABLE 1

Oligonucleotide primers used for degenerate RT-PCR, 5'-RACE and 3'-RACE PCR, genomic PCR, gene sequencing, subcloning and PCR detection in pig tissues of pDC-SIGN

| Primer ID | Sequence (5' to 3')[1] | Position[2] |
|---|---|---|
| NF-05 | ATCAAAASTGMTGAGGAGCAGA (SEQ ID NO: 6) | 473-494 |
| NR-05 | CATTTGTCRTCRTTCCAGCC (SEQ ID NO: 7) | 671-690 |
| NF-06 | AACCGCTTCACCTGGATGG (SEQ ID NO: 8) | 524-543 |
| 5'-RACE PDR-1 | CAGAAGCTGAGTTGGAGGGGCTG (SEQ ID NO: 9) | 589-612 |
| 3'-RACE PDF-1 | GCCACCTGGATTGGCCTCAGTGATG (SEQ ID NO: 10) | 530-554 |
| PCI-XHO | agt*ctcgag*cgccaccATGGCAGAGATATG (SEQ ID NO: 11) | 26-39 |
| DCS3 | tat*ctaga*TCAGAGCATGGGGCAGGGAGA (SEQ ID NO: 12) | 728-748 |
| 1F | GATGGCAGAGATATGTGACCCCAAGGA (SEQ ID NO: 15) | 25-54 |
| 4R | CGGAGGGGCTGCTGAGACCATC (SEQ ID NO: 16) | 966-987 |
| 2F | TCGTCTCATTGGGTTTCTTCATGCTCC (SEQ ID NO: 17) | 168-194 |
| 3F | CTGCAGAGAGAGAGAGAGACCAGCAGGA (SEQ ID NO: 18) | 236-263 |
| 4F | TGCCCCTGGCATTGGGAATTCTT (SEQ ID NO: 19) | 359-381 |
| Nco-DCS-5 | at*acc*ATGGCAGAGATATG (SEQ ID NO: 25) | 26-39 |
| Xho-DCS-3 | agt*ctcgag*TCAGAGCATGGGCAGGGAGA (SEQ ID NO: 26) | 728-748 |
| PDCS-E56F | GAATGCCACCCTGGCTGGCCT (SEQ ID NO: 27) | 328-348 |
| PDCS-E78R | GGGTTCTCCTTCTTTCCAGAAGCTGAGTT (SEQ ID NO: 28) | 600-628 |

[1]The mixed bases (S = C + G, M = A + C, and R = A + G) designed for degenerate primers (NF-05 and NR-05) are shown in bold and underlined. It is noted that the sequences of primers NF-05, NF-06 and NR-05 are not fully identical to that of the final cDNA sequence of pDC-SIGN. For primers PCI-XHO, DCS3, Nco-DCS-5 and Xho-DCS-3, lowercase letters indicate the non-porcine-DC-SIGN sequences; underlined nucleotides represent restriction sites (Xho I, Xba I or Nco I) used for subcloning and italic nucleotides indicate the optimal Kozak sequence before start codon ATG.
[2]Position is corresponding to the full-length cDNA of pDC-SIGN (FIGS. 2a-2b).

Genomic PCR and gene sequencing: The primers used for one-step genomic PCR were based on the sequence of porcine DC-SIGN cDNA as herein determined. The forward primer 1F (5'-GATGGCAGAGATATGTGAC-CCCAAGGA-3' (which corresponds to SEQ ID NO:15)) contains the start codon ATG (underlined) while the reverse primer 4R (5'-CGGAGGGGCTGCTGAGAC-CATC-3' (which corresponds to SEQ ID NO:16)) is complementary to the sequence within the 3'-noncoding region of the cDNA. Genomic PCR was performed with a Platinum PCR HiFi Supermix kit (Invitrogen Corporation, Carlsbad, Calif.) using 150 ng of the pig genomic DNA (purchased from Novagen, Madison, Wis.) in a total volume of 50 µL. The PCR conditions were 35 cycles at 94° C. for 30 sec, 68° C. for 5 min with an initial denaturing of the template DNA at 94° C. for 2 min. The resulting fragment was cloned into a pCR2.1 vector (Invitrogen Corporation, Carlsbad, Calif.) by TA cloning strategy. The M13 forward and reverse primers as well as three gene-specific primers 2F (5'-TCGTCTCATTGGGTTTCTTCATGCTCC-3' (which corresponds to SEQ ID NO:17)), 3F (5'-CTGCA-GAGAGAGAGAGAGACCAGCAGGA-3' (which corresponds to SEQ ID NO:18)) and 4F(5'-TGCCCCTGGCAT-TGGGAATTCTT-3' (which corresponds to SEQ ID NO:19)) were used for sequencing. Assembly of the full-length gene was done with the SeqMan program from Lasergene package (DNASTAR Inc., Madison, Wis.).

Sequence and phylogenetic analyses: Analyses and alignment of DNA and amino acid sequences were performed using Lasergene package (DNASTAR Inc., Madison, Wis.). Sequence analysis and prediction of mRNA splicing of pDC-SIGN gene was performed with online program ASPic (Alternative Splicing Prediction, t.caspur.it/ASPIC/home.php).

Generation of an anti-peptide polyclonal antibody specific to porcine DC-SIGN: To generate a pDC-SIGN-specific anti-peptide polyclonal antibody to detect the expression of pDC-SIGN protein, two peptides corresponding to regions predicted to be exposed within the CRD of porcine DC-SIGN (Acetyl-VDNSPLQLSFWKEGEPNNHGC-amide (which corresponds to SEQ ID NO:13), and Acetyl-AEQKFLKSWYRYNKAC-amide (which corresponds to SEQ ID NO:14)) were commercially synthesized by $21^{st}$ Century Biochemicals Corporation (Marlboro, Mass.) for purposes of the present invention. The peptides were subsequently purified and used together to immunize two New Zealand white rabbits as a custom antibody production service at $21^{st}$ Century Biochemicals Corporation. Porcine DC-SIGN-specific anti-peptide polyclonal antibody was produced from the serum of immunized rabbits by affinity purification at the concentration of 0.73 mg/mL.

Construction of a recombinant vector expressing porcine DC-SIGN and in vitro expression: The complete coding region of pDC-SIGN was amplified by PCR using primers PCI-XHO and DCS3 (Table 1) and subsequently cloned into a pCI-neo vector (Promega Corporation, Madison, Wis.) downstream of the CMV immediate-early enhancer/promoter using Xho I and Xba I restriction sites. The construct was sequenced to verify the identity and designated as pCI-PDCS. For transfection, BHK-21 cells were seeded at $4 \times 10^4$ cells per well onto 8-well Lab-Tek chamber slides (Nalge Nunc International, Rochester, N.Y.), and were grown without antibiotics for 24 hours. Plasmids pCI-PDCS and pCI-neo were transiently transfected into BHK-21 cells using Lipofectamine 2000 (Invitrogen Corporation, Carlsbad, Calif.) according to the manufacturer's protocol with minor modifications. Briefly, 0.4 µg of plasmid DNA was mixed with 1.5 µL Lipofectamine 2000 and 150 µL of Opti-MEM (Invitrogen Corporation, Carlsbad, Calif.) at room temperature for 20 min and subsequently added to the cells. Fresh growth medium was replaced after 6 hours. Cells were cultured for 24 to 48 hours, and were then applied to immunofluorescence assay (IFA) or Western blot to detect the expression of pDC-SIGN protein.

Immunofluorescence assay (IFA) and Western blot: Transfected cells were washed 2 times with PBS, fixed with 4% paraformaldehyde in PBS for 20 min and then permeabilized with 0.5% Triton® X-100 (a nonionic surfactant generically known as polyethylene glycol tert-octylphenyl ether under the registered trademark of Union Carbide Corp., Houston, Tex. and commercially available from Sigma-Aldrich Corp., St. Louis, Mo.) for 10 min. One hundred microliter of the anti-peptide antibody specific to pDC-SIGN at 1:100 dilution in PBS was added over the cells and incubated for 1 hour at 37° C. Cells were washed 3 times with PBS and 100 µL FITC-labeled goat anti-rabbit IgG (KPL, Inc., Gaithersburg, Md.) at 1:100 dilution was then added. After 30 min incubation at 37° C., the cells were washed 3 times with PBS and were visualized under a fluorescence microscope. The IFA was done more than twice using two different dilutions of antibody in PBS at either 1:50 or 1:100 with similar, successful results.

For Western blot analysis, pCI-PDCS or pCI-neo transfected cells were lysed in 125 µL CelLytic M lysis buffer (Sigma-Aldrich Corp., St. Louis, Mo.) per $10^6$ cells. Protein extracts were collected, aliquoted and frozen at −20° C. Samples and protein marker (Precision Plus Protein Kaleidoscope Standards, Bio-Rad Laboratories, Inc., Hercules, Calif.) were resolved on SDS-PAGE and transferred onto polyvinylidene difluoride (PVDF) membrane that was subsequently blocked with Tris-buffered saline (TBS) containing 3% bovine serum albumin (BSA) overnight at 4° C. The pDC-SIGN protein was detected using pDC-SIGN-specific antibody at a 1:200 dilution in TBS for 90 min at room temperature, followed by incubation with horseradish peroxidase (HRP)-conjugated anti-rabbit IgG (KPL, Inc., Gaithersburg, Md.) for 90 min at room temperature. The membrane was then developed with chloronaphthol.

Tissue distribution of pDC-SIGN detected by RT-PCR: Total RNA was isolated from homogenized pig tissues, selected cell populations and cell lines using the RNeasy mini kit (Qiagen Inc., Valencia, Calif.) followed by an RNase-free DNase I treatment, and cDNA was synthesized with Super-Script II reverse transcriptase (Invitrogen Corporation, Carlsbad, Calif.) using oligo-dT (Promega Corporation, Madison, Wis.) as the reverse primer. For pig tissues that were difficult to isolate such as thymus and bone marrow, their tissue cDNA's were purchased from Zyagen Laboratories (San Diego, Calif., USA). PCR was performed in 50 µL reactions with Advantage 2 PCR kit (Clontech, Palo Alto, Calif.), using primer PDCS-E56F spanning the boundary between exon 5 and exon 6 and primer PDCS-E78R spanning the boundary of exon 7 and exon 8 of pDC-SIGN gene (see sequences in above Table 1). The PCR parameters include 30 cycles at 95° C. for 20 sec, 68° C. for 1 min with an initial denaturing of the template DNA for 2 min. The housekeeping gene, porcine glyceraldehyde 3-phosphate dehydrogenase (GAPDH), was also amplified using primers GAPDH5 (5'-GCTGAGTATGTCGTG-GAGTC-3' which corresponds to SEQ ID NO:29) and GAPDH3 (5'-CTTCTGGGTGGCAGTGAT-3' which corresponds to SEQ ID NO:30) by PCR (95° C. for 1 min, 30 cycles at 95° C. for 20 sec, 55° C. for 20 sec, 68° C. for 40 sec and 72° C. for 3 min). The expected size of the PCR products was 301 bp for pDC-SIGN and 285 bp for porcine GAPDH, respectively.

Immunohistochemistry (IHC): Paraffin sections of pig lymph nodes and livers (Zyagen Laboratories, San Diego, Calif.) were immunostained with avidin-biotin complex (ABC) by a previously described method (W. Li et al., "Chronic Relapsing Experimental Autoimmune Encephalomyelitis:

Effects of Insulin-like Growth Factor-I Treatment on Clinical Deficits, Lesion Severity, Glial Responses, and Blood Brain Barrier Defects," J. Neuropath. Exp. Neurol. 57:426-38 (1998)). Briefly, to block endogenous peroxidase activity and nonspecific immunostaining, sections were immersed in 3% $H_2O_2$ for 10 minutes before treatment with 10% normal goat serum (NGS) in PBS (pH=7.4) for 30 minutes at room temperature. The primary antibody, pDC-SIGN-specific anti-peptide polyclonal antibody, and the secondary antibody, biotinylated anti-rabbit IgG (Vector Laboratories, Burlingame, Calif.), were both diluted in 2% NGS in PBS buffer. Primary and secondary antibodies were incubated overnight at 4° C. and 30 minutes at room temperature, respectively. The ABC reagent was prepared and used according to the manufacturer's instructions from VECTASTAIN® Elite ABC kits (complexes between avidin or streptavidin and biotinylated enzymes, designated ABC's commercially available under the registered trademark of Vector Laboratories, Burlingame, Calif.) followed by applying DAB/Ni substrate (Vector Laboratories, Burlingame, Calif.) for 5 minutes. Controls included omission of primary or secondary antibodies, replacement of primary antibody with rabbit IgG, normal rabbit serum, or antigen-antibody complex (pre-antibody absorption). Sections were counterstained with Hematoxylin stain and sealed with Permount slide mounting solution. IHC data were acquired with Nikon DS-Fil digital camera and NIS-Elements software (commercially available from Nikon Instruments, Inc., Melville, N.Y.).

Results and Discussion

Molecular cloning of a full-length porcine cDNA homologue to human DC-SIGN from in vitro cultured porcine MDDCs: It was initially hypothesized that the DC-SIGN homologue of the pig has similar expression and distribution patterns to hDC-SIGN, and thus may be mainly expressed at a high level on the surface of porcine MDDCs which can be used as the source for the cloning of the unknown pDC-SIGN cDNA but further experimentation and determination of unknown cloning parameters were needed to obtain the cDNA and full gene encoding the pDC-SIGN protein. Generation of porcine MDDCs has been previously reported by several groups (C. P. Carrasco et al., "Porcine dendritic cells generated in vitro: morphological, phenotypic and functional properties," Immunology 104:175-84 (2001); R. Paillot et al., "Functional and phenotypic characterization of distinct porcine dendritic cells derived from peripheral blood monocytes," Immunology 102:396-404 (2001); C. L. Loving et al., "Differential type I interferon activation and susceptibility of dendritic cell populations to porcine arterivirus" Immunology 120:217-29 (2007)). Using procedures described in the literature, single and aggregated veiled-shaped cells were observed after three days of culture of adherent porcine CD14-positive monocytes in the presence of rpGM-CSF and rpIL-4. The characteristic dendritic morphology of the cells that had almost transformed from monocytes in the cultured dish was more significant after seven days (FIG. 1(a)). Phenotyping of the cells resulted in MHC $II^+CD1^+CD11b/c^+$ $CD80/86^+$ which was consistent with other reports and thus recognized as MDDCs (id.). A sequence similarity search from the database of the Swine Genome Sequencing Project (SGSP, www.ncbi.nlm.nih.gov/sites/entrez?Db=genomeprj&cmd=ShowDetailView&TermToSearch=13421) in NCBI did not yield any sequences of porcine DC-SIGN homologues of the human DC-SIGN. In addition, other predicted DC-SIGN homologues from domestic animal species had not been released from the genome databases when the experimentation relating to the present invention had been started. Therefore, to identify a novel porcine DC-SIGN gene, a series of degenerate primers was first designed based on the conserved sequences based upon multiple alignments of the known human, non-human primates and mouse DC-SIGN related cDNAs (T. B. Geijtenbeek et al., "Identification of DC-SIGN, a novel dendritic cell-specific ICAM-3 receptor that supports primary immune responses," Cell 100:575-585 (2000); Bashirova et al., 2001, supra; F. Baribaud et al., "Functional and antigenic characterization of human, rhesus macaque, pigtailed macaque, and murine DC-SIGN," J. Virol. 75:10281-10289 (2001); Park et al., 2001, supra; A. A. Bashirova et al., "Novel member of the CD209 (DC-SIGN) gene family in primates," J. Virol. 77:217-27 (2003)). An approximately 210-bp product was first amplified by RT-PCR from total RNA of MDDCs with the primers NF-05 and NR-05 (FIG. 1(b)). A nested-PCR using the gel-purified fragment as the template with the same forward primer NF-05 and a new reverse primer NR-06 upstream to primer NR-05 also generated (i.e., amplified) a fragment with smaller size, indicating the specificity of the PCR. Sequence analysis showed that the sequence of this initial PCR fragment shares 62.6%, 61.2%, and 57.6% sequence identity, respectively, to the corresponding region of human DC-SIGN, human L-SIGN and mouse DC-SIGN (SIGNR5) cDNA sequences, which represents a region in the CRD of DC-SIGN.

Based upon this initial sequence, two gene-specific primers could be designed to amplify the 5'- and 3'-proximal regions of the cDNA by 5'- and 3'-RACE PCR, respectively. Since the reverse primer PDR-1 for 5'-RACE PCR is located downstream of the 3'-RACE PCR primer PDF-1, the amplified 5'-RACE and 3'-RACE PCR products were expected to have a 82-nt overlapping region, thus covering the full-length sequence of the cDNA. The resulting two PCR products, each with approximately 600 bp from the respective RACE PCR (FIG. 1(c)), were assembled into a full-length cDNA sequence. A BLAST search with this cDNA did not yield any homologue's sequence in Sus scrofa, indicting it is a novel porcine DC-SIGN equivalent (that is, a species homologue) which corresponds to the human DC-SIGN. The newly discovered cDNA was designated as porcine DC-SIGN (pDC-SIGN).

Characterization of porcine DC-SIGN cDNA and its deduced protein product: The 1069-bp pDC-SIGN cDNA encompassed an open reading frame (ORF) of 723 nucleotides from position 26 to 728 encoding a protein with 240 amino acids (FIGS. 2a-2b). Like other C-type lectins, the deduced pDC-SIGN product is predicted to be a type II transmembrane protein beginning from a putative 39-aa cytoplasmic tail (CT) followed by a putative 31-aa transmembrane domain (TMD). The extracellular domain consisted of a 38-aa neck region followed by a 132-aa CRD (FIGS. 2a-2b). An internalization motif, dileucine-based motif at aa position 27-28, was found within the CT. Since internalization motifs in the CT of the transmembrane receptors are important for the internalization of the ligand-receptor complex, it is likely that the porcine DC-SIGN is able to mediate endocytosis and transfer the potential bound pathogen into the cytoplasm of the DC. Human DC-SIGN, hL-SIGN, nonhuman primate DC-SIGN and mSIGNR1 contains variable repeated sequences within the neck region whereas the remaining mSIGNR members, except SIGNR2 and SIGNR6, do not have repeated sequence. The sequence in the neck region of pDC-SIGN was non-repeated and the length was closer to SIGNRs 3-5 but was highly related to mouse SIGNR7 and SIGNR8.

The CRD of pDC-SIGN had a similar size with all the other known DC-SIGN homologue proteins, although their overall sizes were quite different due to the variation of the neck region. The CRD was also the most conserved region shared by porcine and other non-porcine DC-SIGN homologue proteins, encompassing the key residues that form $Ca^{2+}$— and carbohydrate-binding sites. The CRD of hDC-SIGN has been shown to bind two calcium ions using two close but distinct sites (T. B. Geijtenbeek et al., "Identification of different binding sites in the dendritic cell-specific receptor DC-SIGN for intercellular adhesion molecule 3 and HIV-1," J. Biol. Chem. 277:11314-11320 (2002)). The $Ca^{2+}$ site 1 contains amino acid residues Asp176, Glu180, Asn203 and Asp208 that are essential for interaction of DC-SIGN with its ligands. All four of these residues were conserved in pDC-SIGN. Porcine DC-SIGN also had the common Glu-Pro-Asn sequence (EPN sequences, aa position 200-202) and Glu207 as well as Asn218 involved in the $Ca^{2+}$ site 2 that are critical for binding mannose-, fucose- or galactose-containing oligosaccharides. In addition, eight conserved cysteines predicted to form disulfide bonds were found in the CRD.

Since computer-predicted cDNAs encoding equine, opossum, canis and bovine DC-SIGN homologues are available in genome databases, the putative complete amino acid sequences of their encoding proteins, together with those from primates and mouse DC-SIGN related proteins, were included to perform phylogenetic analysis. Also included was the novel porcine LSECtin, a C-type lectin closely-related to, but distinct from, DC-SIGN, as an out-group to construct a neighbor-joining phylogenetic tree. The results showed that the porcine and bovine proteins are most closely related to each other than to others. A surprising finding was that mSIGNR7, mSIGNR8, canis and equine DC-SIGNs were clustered together with porcine and bovine proteins, forming an individual cluster (i.e., clade) different from the cluster containing other mouse and primates homologues. Pairwise sequence comparison of the complete pDC-SIGN protein with the DC-SIGN homologues from other species revealed that pDC-SIGN was more homologous to bovine, canis and equine proteins as well as to SIGNR7 and SIGNR8 (over 50%) than to other DC-SIGN homologues (less than 50%), which was consistent with the phylogenetic comparison of CRD sequences.

In vitro expression of porcine DC-SIGN protein: In order to determine if the pDC-SIGN is effectively translated and, if so, whether the translated product has the putative transmembrane property, a transfection experiment was conducted using BHK-21 cells. The full-length coding region of the pDC-SIGN gene with 720 bp was amplified by PCR from RNA extracts of porcine MDDCs, and was subsequently subcloned into a eukaryotic expression vector pCI-neo, to obtain plasmid pCI-DCS. BHK-21 cells were transfected with this construct or vector alone. The expression of pDC-SIGN protein was detected by IFA using a pDC-SIGN-specific anti-peptide antibody raised against two peptides in the CRD. The IFA results showed that most cells expressing pDC-SIGN had a spreading cytoplasmic and membrane staining (FIG. 3a). Some cells showed the fluorescent signals only localizing on the cell membrane (FIG. 3b). In contrast, cells transfected with pCI-neo vector did not have any positive IFA signals (FIG. 3c). It was concluded from these results that the cDNA encoding porcine DC-SIGN is effectively translated in vitro and that the resulting product is indeed a type II transmembrane protein, that is, the cDNA of pDC-SIGN encodes a type II transmembrane protein. While the results illustrated effective translation, the assay showed only an approximate 30% positive expression of pDC-SIGN by the transient transfection of the pCI-PDCS plasmid. The anti-pDC-SIGN antibody also detected a specific band of ~48 kDa in the lysate of cells transfected with pCI-PDCS but not in cells transfected with the empty vector control (FIG. 3d). The molecular size was larger than that predicted from the deduced amino acids sequence (28 kDa) probably due to glycosylation, as pDC-SIGN contains a putative N-linked glycosylation site (aa 102) in the neck region.

Characterization of full-length gene encoding porcine DC-SIGN protein: After cloning and sequencing the cDNA of the pDC-SIGN, the gene sequence of pDC-SIGN was then sought and obtained. By using one-step genomic PCR, a unique band of approximately 3.5 kb was amplified only when the annealing and extension steps of the PCR cycle were combined together at 68° C. (FIG. 4(a)). After cloning of the PCR product into the TA vector, five individual sequences determined by DNA sequencing using the respective sequencing primer that shared a tandem overlapping region were assembled into a contig that represented the genomic sequence encoding the pDC-SIGN gene (FIG. 4(b)). The consensus sequence of the pDC-SIGN gene with 3438 bp in length was determined by comparison of the sequences among three different independent clones. Sequence analysis and pairwise alignment with the cDNA sequence revealed that the pDC-SIGN gene was encoded by eight exons spanning the complete coding region of the gene in which exons 1 and 8 had undetermined sizes. Although extra nucleotide sequences at the both termini in the noncoding region of the determined porcine cDNA were not included in the gene, the sequence of all the eight exons was fully identical to that of the coding region and partial 3' end noncoding region of the cDNA, indicating the authenticity of the gene (FIGS. 5a-5d).

The intron sizes vary from 113 to 689 bp and all acceptor and donor sequences on the introns conform to the GT-AG rule. Additional alternatively spliced mRNA isoforms were not predicted by the computer software program ASPic, suggesting that the identified cDNA from porcine monocyte-derived dendritic cells is likely the only existing isoform of the pDC-SIGN expression, which is consistent with the RACE-PCR result described herein. The detailed sequence is displayed in FIGS. 5a-5d. The translation start site begins in exon 1. The 3' end of exon 1, the entire exon 2 and the 5' end of exon 3 encode the cytoplasmic tail (CT). The remaining part of exon 3 and the 5' end of exon 4 encode the transmembrane domain (TMD). The neck region follows the TMD sequence in exon 4, spans the entire exon 5 and the first 8 nucleotides of exon 6. The rest of exon 6, the entire exon 7 and the 5' end of exon 8 encode the carbohydrate recognition domain (CRD).

The pDC-SIGN gene shares a similar structure and size of eight exons with the predicted bovine, canis DC-SIGN gene and the identified mouse SIGNR8 gene, including the localization of the four domains to the corresponding exons. Pairwise comparison of the genomic sequences of pDC-SIGN with bovine DC-SIGN, canis DC-SIGN or mouse SIGNR8 revealed that the last three exons encoding the CRD have the highest sequence identity (70-85%). Overall identity of the pDC-SIGN genomic sequences with other species (bovine DC-SIGN>canis DC-SIGN>mouse SIGNR8) was also consistent with the result from the phylogenetic analysis of DC-SIGN proteins. Although limited sequence identity in the overall intron sequences was shown in the four genes, some of the intron regions adjacent to the exons were conserved, especially between the porcine and bovine DC-SIGN genes and the porcine and canis DC-SIGN genes. These conserved sequences may contain the common elements regulating the gene expression.

To further confirm that the porcine DC-SIGN gene is the first experimental identified gene among the non-primate large mammalian species, a porcine transcript and Unigene clusters alignment with human genome was performed by map viewer in NCBI website. Comparative mapping of DC-SIGN (CD209) between human and pig chromosomal segments including Ssc UniGene and Ssc RNA on pig genome was done using the regional display between 7,400K to 8,040K from NCBI Map Viewer Build 36.2. Human DC-SIGN gene is localized on chromosome 19p13.3 according to NCBI map viewer build 36.2. Based on the correspondence between human and pig chromosomal segments, the pDC-SIGN gene is predicted to assign on (localized on) pig chromosome 2 between SSC 2q1.1 to q2.1.

Tissue and cellular distribution of pDC-SIGN: Expression of pDC-SIGN mRNA was detected in both of the primary (thymus and bone marrow) and the secondary lymphoid organs (lymph node and spleen) as well as lung and skeletal muscles but not in duodenum, kidney, heart or liver of pig by RT-PCR (FIG. 6a). The expression level in lymph node and bone marrow was the highest. The detection of DC-SIGN expressed in muscles was intriguing, though mouse SIGNRs 7 and 8 were also found to express in skeletal muscle.

Taking pDC-SIGN expression in various lymphoid organs into account, it was speculates that pDC-SIGN may be also expressed by specific hematopoietic cell populations in addition to MDDCs. Hence, flow cytometry analysis was performed to detect the surface expression of pDC-SIGN protein on PBL, monocytes, MDDCs, MDMΦs and PAM (FIGS. 6b to 6d). Scatter profile of porcine PBMC clearly indicated two cell populations, PBL and monocytes, according to their morphology. Since CD14 molecule is the surface marker for porcine monocytes, these two cell populations could be separated by immunomagnetic labeling MACS system using anti-porcine CD14 monoclonal antibody. CD14+ monocytes were further used to develop MDDCs with the addition of rpGM-CSF and rpIL-4 or MDMΦs in the absence of the cytokines, respectively. PBL and the monocytes did not show any pDC-SIGN expression, which was somewhat expected since hDC-SIGN or L-SIGN is not expressed on lymphocytes or monocytes. Accordingly, there was no detectable pDC-SIGN expression on a porcine monocytic cell line 3D4/31 (FIGS. 6b to 6d). Upon differentiation of the monocytes into MDDCs in culture, the pDC-SIGN expression was up-regulated with an approximately 8-fold increase of median fluorescence intensity from day 3 to day 7. Porcine DC-SIGN expression was also found on MDMΦs. Compared to MDDCs, the majority of MDMΦs gave a pDC-SIGN phenotype. PAM's were dominated by a pDC-SIGN phenotype, but the expression level was lower than that on MDMΦs. In accordance with undetectable expression of pDC-SIGN mRNA in pig kidney, the protein was not expressed in an epithelial cell line PK15 derived from pig kidney (FIGS. 6b to 6d).

To further confirm whether pDC-SIGN protein was indeed expressed in particular cell populations of lymphoid tissues, IHC analysis on paraffin sections of pig lymph node and liver tissues was performed. It was found that pDC-SIGN protein showed a predominant sinusoidal pattern of expression in lymph nodes (FIG. 7(a)). However, there was no detectable expression in pig livers (FIG. 7(b)), which was consistent with the RT-PCR results (FIG. 6a). Most of the cells immunostained with pDC-SIGN-specific anti-peptide antibody in sinuses of lymph nodes were macrophage-like and dendritic-like cells (FIG. 7(c)). Endothelial cells in lymphatic vessel of parenchyma were also immunostained with pDC-SIGN-specific anti-peptide antibody (FIG. 7(d)). The expression pattern of pDC-SIGN protein in pig lymph nodes is analogous to that of hDC-SIGN in human lymph nodes where hDC-SIGN protein was identified not only on sinusoidal macrophages but also on endothelial cells by IHC. The absence of pDC-SIGN expression in pig livers supported that the cloned pDC-SIGN is not the L-SIGN homologue since the presumed porcine L-SIGN, if exists, should be strongly expressed on LSECs.

EXAMPLE 2

Generation of a Stable Cell Line Expressing Porcine DC-SIGN

Materials and Methods

Construction of a bicistronic expression vector harboring porcine DC-SIGN: The complete coding region (723 bp) of pDC-SIGN was amplified by PCR using primers Nco-DCS-5 (5'-ATACCATGGCAGAGATATG-3' (which corresponds to SEQ ID NO:25)) and Xho-DCS-3 (5'-AGTCTCGAGTCAGAGCATGGGGCAGGGAGA-3' (which corresponds to SEQ ID NO:26)) and subsequently cloned into a bicistronic expression vector pTriEx-1.1 Neo vector (commercially available from Novagen, Madison, Wis.) (the sequence and map of the pTriEx-1.1 Neo vector are shown at www.emdbiosciences.com/docs/docs/PROT/TB293.pdf) downstream of a hybrid promoter composed of the CMV immediate early enhancer fused to the chicken beta-actin promoter using Nco I and Xho I restriction sites. The construct, designated "pTriEx-PDCS," was sequenced to verify the identity and determined to be 7243 by in length (includes the backbone vector pTriEx-1.1 Neo (6664 bp) plus the insertion of the protein coding region of porcine DC-SIGN (723 bp) and the subtraction of the sequence between Nco I and Xho I on the vector (144 bp)). The pTriEx-PDCS construct was subsequently used to generate a stable cell line (BHK-21) stably expressing pDC-SIGN.

Transfection and stable cell line selection: BHK-21 cells were seeded at $2\times10^5$ cells per well onto a 6-well plate and were grown in complete growth medium (10% fetal bovine serum in DMEM) without antibiotics for approximately 24 hours until they reach 80%-90% confluency before transfection. Individual well of the cells was transfected with plasmid pTriEx-PDCS or empty vector pTriEx-1.1 Neo, respectively, using Lipofectamine 2000 (Invitrogen Corporation, Carlsbad, Calif.) according to the manufacturer's instruction. Briefly, 2 μg of plasmid DNA was mixed with 6 μL Lipofectamine 2000 and 500 μL of Opti-MEM (Invitrogen Corporation, Carlsbad, Calif.) at room temperature for 20 min and then added to the cells. The transfected cells were incubated for approximately 36 hours to allow expression of the target pDC-SIGN gene without the growth medium and then replaced with complete growth medium plus Geneticin® selective antibiotic (a G-418 reagent that is an aminoglycoside analog of neomycin sulfate related to Gentamicin that is commercially available from Invitrogen Corporation, Carlsbad, Calif.) at a concentration of 1 mg/mL. The Geneticin®-containing medium was changed every two days to remove dead or dying cells. After 12 days, the surviving cells were treated with trypsin and plated in 60-mm dishes at a dilution such that single cells would give rise to well-separated, individual colonies. The cells were grown for approximately two weeks until individual colonies of several hundred cells were present and isolated by cloning rings technique. The locations of colonies to be removed were marked and cloning rings were carefully placed to encircle the colonies. The cells in a cloning ring were trypsinized and then transferred into an individual well of a 24-well plate. When the transferred cells had grown to sufficient density, they were re-plated in T-25 flasks, grown until the cells reach 100% confluency and recognized as an engineered cell line.

Human ICAM-3 and ICAM-2 binding assay: Adhesion of human ICAM-3 or ICAM-2 to pDC-SIGN proteins was assessed with BHK-PDCS and BHK-21 cells by measuring detectable cells that bound the soluble immunoadhesins through FACS analysis. 3T3-HDCS cells were used as the positive control. Cells (1~3×10$^5$ per sample) were resuspended in 100 μL PBS containing 2% FBS and incubated for 60 min at 4° C. with 1 μg of recombinant human IgG$_1$ Fc (hFc), human ICAM-3-Fc (hICAM3-Fc) chimera or hICAM2-Fc chimera (R&D Systems, Minneapolis, Minn.) in the presence or absence of mannan (100 μg/mL) or ethylene glycol tetraacetic acid (EGTA, 10 mM). Cells were then washed twice and incubated for another 45 min at 4° C. with 0.5 μg of FITC-labeled anti-human IgG Fc antibody (KPL, Inc., Gaithersburg, Md.) in 100 μL PBS containing 2% FBS. Fluorescence was monitored using FACSAria (BD Biosciences, San Jose, Calif.).

Flow cytometry analyses: BHK, 3D4/31, PK15 and 3T3-HDCS cells used for surface staining were collected by trypsin treatment, counted and adjusted to 1×10$^6$ cells/mL in chilled washing buffer (PBS buffer containing 0.1% sodium azide and 0.2% BSA). For each of porcine PBL, PAM, MDDCs and MDMΦs, the cell concentration was adjusted to 2~5×10$^5$ cells/mL. After microcentrifugation and removal of the buffer, approximately 2~10×10$^5$ cells were incubated with 10 μL of the pDC-SIGN-specific antipeptide antibody to porcine DC-SIGN at optimal dilution (1:25 for BHK cells and 1:100 for porcine cells, though an earlier flow cytometry analysis performed at 1:50 dilution for porcine cells also worked fine) in PBS for 30 to 60 min. The cells were washed to remove unbound antibody and stained with 10 μL of FITC-labeled goat anti-rabbit IgG (KPL, Inc., Gaithersburg, Md.) at 1:100 dilution in PBS for 30 min. The two staining procedures were performed at 4° C. For detection of human DC-SIGN expressed on 3T3-HDCS, a mouse anti-hDC-SIGN mAb (clone 120507, NIH AIDS Research and Reference Reagent Program) and a FITC-labeled goat anti-mouse IgG (KPL, Inc., Gaithersburg, Md.) were used for staining. Fluorescence was monitored using FACSAria (BD Biosciences, San Jose, Calif.) or FACSCalibur (BD Biosciences, San Jose, Calif.) and the results were analyzed using FlowJo software (Tree Star, Ashland, Oreg.). The representative cell line expressing porcine DC-SIGN on the surface that was confirmed by flow cytometry analysis was designated "BHK-PDCS." To obtain a high level of pDC-SIGN expression, cell line BHK-PDCS was further sorted using the pDC-SIGN antibody by fluorescence-activated cell sorting (FACS).

Results and Discussion

Generation of a stable cell line expressing porcine DC-SIGN: The bicistronic expression vector pTriEx-1.1 Neo can be used to generate cell lines expressing target genes. The vector uses an internal ribosome entry site (IRES) derived from the encephalomyocarditis virus (ECMV), allowing the inserted target gene and the neomycin-resistance gene to be translated from a single mRNA. PCR amplicon encoding the complete coding region of pDC-SIGN was introduced into the downstream of a hybrid promoter as the first cistron that is cap dependent, while the neomycin-resistance gene is under the control of IRES as the second cistron. With this vector system, selection of stable cell lines transfected with pTriEx-PDCS is more efficiently accomplished than using pCI neo vector-derived construct (pCI-PDCS), presumably because of the linked expression of both genes.

A representative BHK-21 cell colony transfected with the pDC-SIGN expression plasmid pTriEx-PDCS was developed into a cell line under the selection of Geneticin® antibiotic (a G-418 reagent that is an aminoglycoside analog of neomycin sulfate related to Gentamicin that is commercially available from Invitrogen Corporation, Carlsbad, Calif.); and the cell line was designated BHK-PDCS. To determine whether pDC-SIGN can be expressed on the cell surface, cell lines BHK-PDCS and BHK-21 were stained with polyclonal pDC-SIGN antibody for flow cytometry analysis. Shown in FIG. 8a, no detectable staining with the antibodies was displayed on BHK-21 cells whereas the surface expression of pDC-SIGN protein on BHK-PDCS cells was detected, indicating that the BHK-PDCS cell line was able to synthesize pDC-SIGN proteins. The result also confirmed that pDC-SIGN belongs to a type II integral membrane protein family. BHK-PDCS was further enriched and sorted, to obtain a purer cell population with pDC-SIGN expression, by FACS and used for the subsequent binding experiments. In addition, 3T3-HDCS cell line stably expressing hDC-SIGN (described by L. Wu et al., "Functional evaluation of DC-SIGN monoclonal antibodies reveals DC-SIGN interactions with ICAM-3 do not promote human immunodeficiency virus type 1 transmission," J. Virol. 76:5905-14 (2002)) verified by staining with a hDC-SIGN specific mAb (FIG. 8a) was used for a positive control.

Binding of human ICAM-3 and ICAM-2 immunoadhesins to BHK cells stably expressing pDC-SIGN: Binding of soluble hFc, hICAM-3-Fc and hICAM-2-Fc in the presence or absence of either mannan or EGTA to pDC-SIGN-negative BHK-21 cells was not observed (FIGS. 8b-8e). However, a binding of either hICAM-3-Fc or hICAM-2-Fc to both of the DC-SIGN-positive cells was observed. Binding of hICAM-3-Fc to BHK-PDCS cells had a higher affinity than binding of hICAM-2-Fc to BHK-PDCS cells. The binding was specific since binding of hFc alone to BHK-PDCS or 3T3-HDCS was negative. Furthermore, the addition of mannan blocked the binding of both hICAM-3-Fc and hICAM-2-Fc, so did the presence of EGTA. Inhibition by EGTA was more efficient than that by mannan in both of the DC-SIGN-positive cells (FIGS. 8b-8e). The results indicated that pDC-SIGN is able to cross-react with human ICAM-3 or ICAM-2 and the interaction is dependent on $Ca^{2+}$ and is mediated by the CRD of pDC-SIGN.

EXAMPLE 3

Involvement of Porcine DC-SIGN on Transmission of or Infection by Porcine Reproductive and Respiratory Syndrome Virus (PRRSV)

Materials and Methods

Generation of PRRSV virus stocks: Two PRRSV strains from different genotypes were used in this study. The virus stocks of genotype 1 PRRSV expressing green fluorescent protein (GFP), designated "PGXG" for purposes of this study, was generated by transfection of MARC-145 cells capable of supporting PRRSV infection with a PRRSV infectious cDNA clone (a gift of Dr. Ying Fang, South Dakota State University). The infectious PRRSV cDNA clone was modified to be DNA-launched with much higher efficiency followed by two serial passages on MARC-145 cells. The virus stocks were PRRSV-containing supernatants without cell debris, which was removed by centrifugation. The virus titers of PGXG and a genotype 2 North American PRRSV strain VR2385 kept under storage conditions were determined by limiting dilution on MARC-145 cells through IFA and quantified as fluorescent focus-forming unit (FFU) per mL, respectively.

PRRSV binding assay: BHK-PDCS and BHK-21 cell monolayers were dispersed by incubation with cell dissociation buffer (an enzyme free PBS-based buffer commercially available from Invitrogen Corporation, Carlsbad, Calif.) and washed twice with PBS containing 2% FBS. A total of $5 \times 10^5$ cells in suspension were inoculated with a PRRSV strain VR2385 at a multiplicity of infection (M.O.I.) of 10 FFU per cell. After virus adsorption for 60 min at 4° C. and washing twice, cells were incubated with a PRRSV mAb SDOW17-A (Rural Technologies, Inc., Brookings, S.Dak.) at a 1:1000 dilution for 30 min at 4° C. Cells were subsequently washed twice to remove free antibody and then incubated with a FITC-labeled goat anti-mouse IgG (KPL, Inc., Gaithersburg, Md.) at a 1:50 dilution to determine the binding of PRRSV to the cells by FACS analysis. For the PRRSV-blocking ICAM-3 binding assay, BHK-PDCS cells were incubated with either PGXG or VR2385 (M.O.I.=10 FFU per cell) for 60 min at 4° C. before hICAM-3-Fc addition.

PRRSV capture and in trans transmission assay: BHK-PDCS, BHK-21 or MARC-145 donor cells ($2.5 \times 10^5$ cells for each) were incubated with either PGXG or PRRSV VR2385 virus at a M.O.I. of 0.5 FFU per cell in a volume of 500 µL for 3 hours to allow adsorption of the virus. Cells were then washed with PBS, mixed with MARC-145 target cells ($1.0 \times 10^5$) in 1 mL MEM supplemented with 2% FBS and seeded onto individual wells of 12-well plates. Three days post-infection, cells were scraped and the PRRSV viruses were recovered by three cycles of freeze-thaw. Virus titers were determined as described above.

Results and Discussion

Figure 9A:
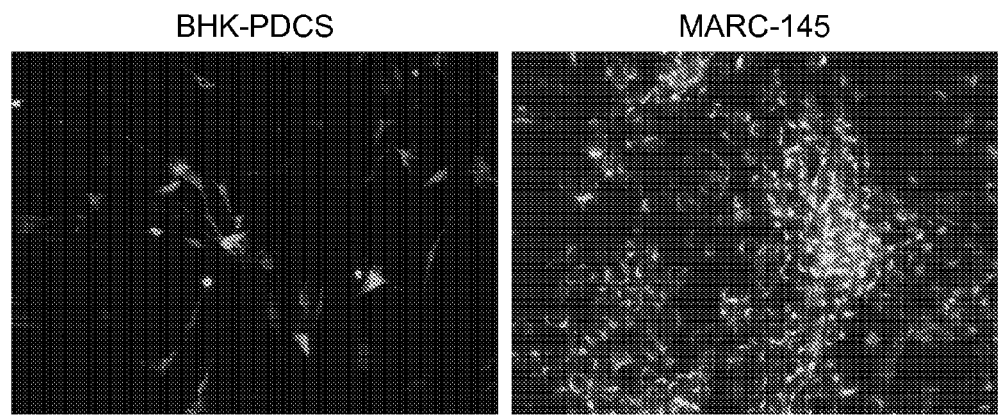
FIGS. 9a to 9d provide the infectious results of Porcine Reproductive and Respiratory Syndrome Virus (PRRSV) in BHK-PDCS cells.
Figure 9B:
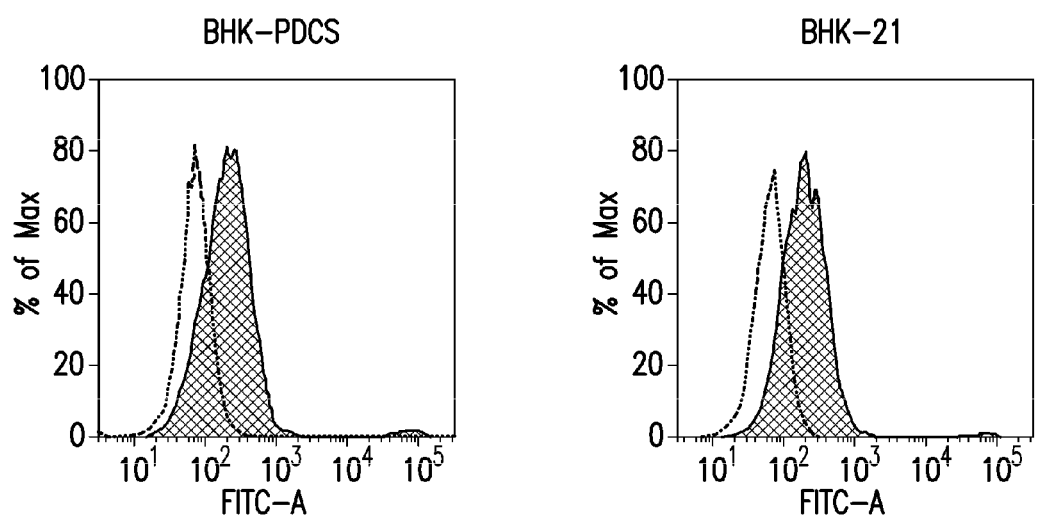
Figure 9C:
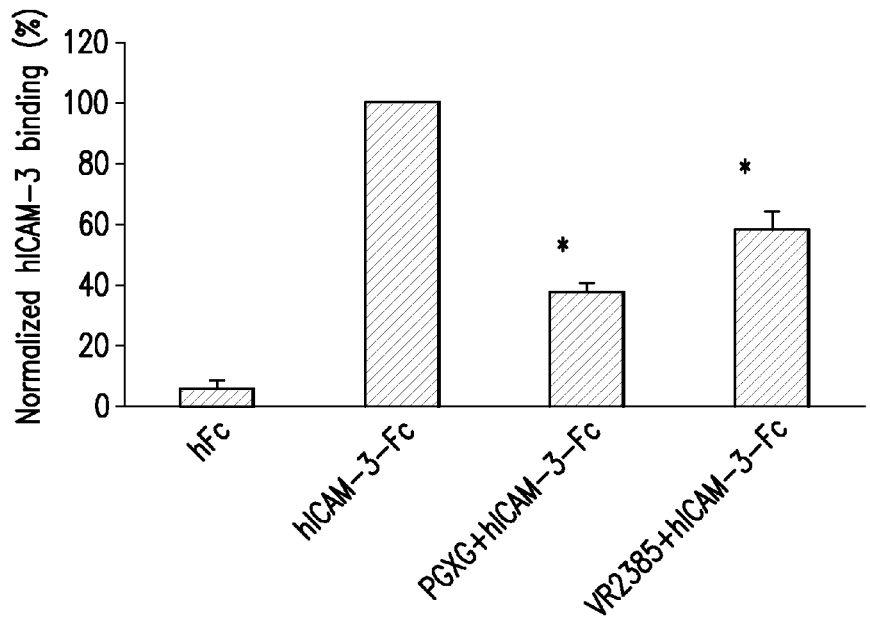

Porcine DC-SIGN expressed on the surface of BHK cells is not involved in the PRRSV virus entry but enhances PRRSV transmission to target MARC-145 cells in trans: BHK-21 was shown to support enveloped PRRSV replication inside the cell but not allow cell-to-cell spread of the virus (see earlier study of J. J. Meulenberg et al., "Infectious transcripts from cloned genome-length cDNA of porcine reproductive and respiratory syndrome virus," J. Virol. 72:380-7 (1998)). Since pDC-SIGN was expressed on PAM, the susceptible host cells for PRRSV which contains highly-glycosylated envelope viral proteins, it was important to see if pDC-SIGN expressed on the cell surface was involved in PRRSV attachment and entry. Transfection of BHK-PDCS cells with a genotype 1 PRRSV infectious cDNA clone could recover the virus with GFP expression that subsequently propagated in target MARC-145 cells (FIG. 9a). However, the virus (PGXG) released into the cell culture medium was unable to infect the untransfected BHK-PDCS cells, demonstrating that pDC-SIGN is not involved in PRRSV entry. Since BHK-21 cell line was also known to be susceptible for PRRSV binding (see, for example, D. Therrien et al., "Preliminary characterization of protein binding factor for porcine reproductive and respiratory syndrome virus on the surface of permissive and non-permissive cells," Arch. Virol. 145:1099-16 (2000)), a PRRSV specific binding assay was subsequently performed to compare the virus attachment on the cell surface between BHK-PDCS and BHK-21 cells. It was found that PRRSV indeed bound to both cell lines, although it was difficult to quantify the difference (FIG. 9b). To determine whether the attachment of PRRSV on BHK-PDCS cells could interfere with the pDC-SIGN-hICAM-3 interaction, cells were pretreated with either genotype 1 PRSV strain PGXG or genotype 2 PRRSV strain VR2385 before the hICAM-3-Fc binding. The results showed that both PRRSV strains blocked the hICAM-3 binding, suggesting an unexpected correlation between PRRSV attachment and expression of pDC-SIGN on the BHK cell surface (FIG. 9c).

Figure 9D:
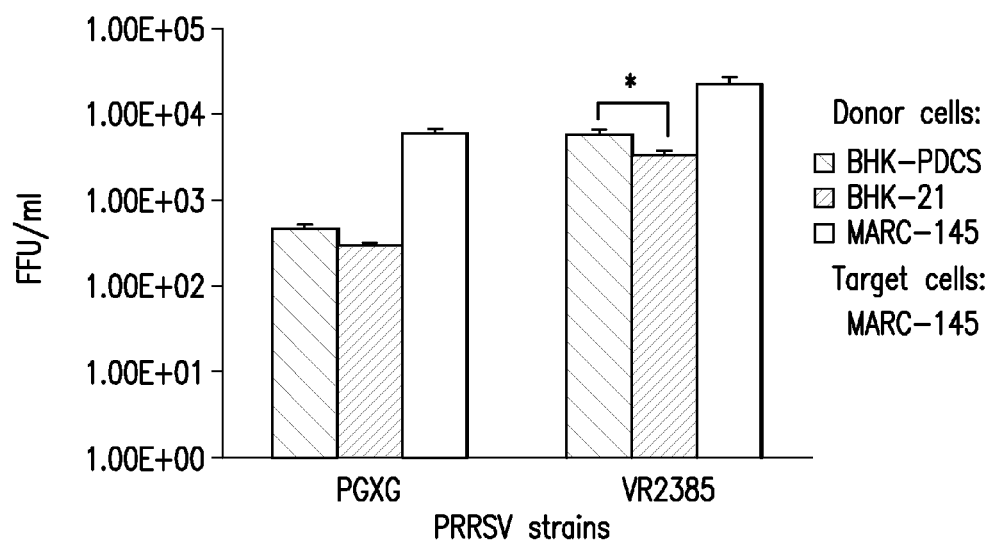

Furthermore, since hDC-SIGN has been shown to efficiently transmit viruses to target cells, whether pDC-SIGN has the analogous ability to facilitate PRRSV transmission through donor cell-to-target cell contacts in trans was in question. BHK-PDCS and BHK-21 cells were used as donor cells whereas the susceptible MARC-145 cells were used as the target cells (or donor cells in the control) in the PRRSV capture and transmission assay. The donor cells were incubated with culture medium (as a mock-incubation control), PRRSV PGXG strain and PRRSV VR2385 strain, respectively. Compared to the virus titers obtained from direct infection of MARC-145 cells with PRRSV at the same M.O.I. of 0.5 FFU per cell that could reach up to $1 \times 10^7$ FFU/mL, the virus titers of PRRSV grown in MARC-145 cells transmitted by three types of donor cells were much lower, ranging from $2.9 \times 10^2$ FFU/mL to $2.5 \times 10^4$ FFU/mL (FIG. 9d), indicating that the transmission of PRRSV could be quantified in spite of the low efficiency. PRRSV transmitted by MARC-145 cells was more efficient than that by the two BHK cells due to the presence of more cells (donor cells were also used as target cells). PRRSV transmission by BHK-PDCS was enhanced by 52% (p=0.07) for PRRSV PGXG strain and by 72% (p=0.02) for PRRSV VR2385 strain compared to that by BHK-21 cells, respectively (FIG. 9d), suggesting that pDC-SIGN is probably associated with PRRSV transmission in trans under these conditions.

EXAMPLE 4

Cloning and Characterization of Porcine ICAM-3 cDNA Isoforms

Materials and Methods

Pigs: Venous blood samples were collected from healthy crossbred conventional pigs of 3 to 7 weeks of age. Pigs were maintained in an isolated room under experimental conditions.

Preparation and culturing of CD14-positive monocytes from pigs: Heparinized blood collected from pigs was diluted 1:2 with phosphate-buffered saline (PBS) and centrifuged over Ficoll-Paque PREMIUM (GE Healthcare, Sweden) at 1000 g for 40 min at room temperature. The buffy coat layer containing peripheral blood mononuclear cells (PBMC) was isolated and washed three times with PBS at 250 g for 10 min at 4° C. CD14-positive monocytes on the surface in PBMC were sorted by immunomagnetic labeling MACS system of cells using anti-CD14 mAb (M-M9, VMRD Inc., Pullman, Wash., USA) and goat anti-mouse IgG1-magnetic microbeads (Miltenyi Biotec GmbH, Bergisch Gladbach, Germany). Purified monocytes were resuspended at 1×10⁵ cells/mL in Dulbecco's modified Eagle's medium (DMEM) supplemented with 10% heat-inactivated fetal bovine serum (FBS), 55 µmol/L of β-mercaptoethanol and antibiotics. The monocytes were then cultured in 6-well plates or 60-mm Petri dishes at 37° C. in the presence of 25 ng/mL of recombinant porcine granulocyte-macrophage colony stimulating factor (rpGM-CSF, R&D Systems, Minneapolis, Minn.) and 25 ng/mL recombinant porcine interleukin-4 (rpIL-4, Endogen, Rockford, Ill.). Half of the culture medium was replaced with fresh medium every 3 days.

RNA extraction: In vitro cultured porcine monocytes were harvested between the seventh and the tenth days, and used as porcine monocyte-derived dendritic cells (MDDCs). Total RNAs from porcine MDDCs were isolated using RNeasy mini kit (Qiagen Inc., Valencia, Calif.) according to the manufacturer's protocol.

5'-RACE, 3'-RACE and RT-PCR: RT and RACE-PCR were performed with a SMART RACE cDNA amplification kit and Advantage 2 PCR Enzyme Systems (Clontech, Palo Alto, Calif.) according to the manufacturer's manual. The gene-specific primers used for 5'-RACE and 3'-RACE were PIC54 (5'-GCGTCCAGGTTAAGACACGCCG-3' (which corresponds to SEQ ID NO:20)) and PIC51 (5'-TCCGCGAGCAGAGACGACCACG-3' (which corresponds to SEQ ID NO:21)), respectively, which were designed based on the sequence of known partial porcine ICAM-3 gene (GenBank accession no. AJ632303) (Leeb and Muller, 2004, supra). The RACE reaction products were sequenced directly with the respective primers and were subsequently cloned into pCR2.1 vector (Invitrogen Corporation, Carlsbad, Calif.) by TA cloning strategy and sequenced with M13 forward and reverse primers at the Virginia Bioinformatics Institute (Blacksburg, Va.).

To verify the integrity of two isoforms of full-length porcine ICAM-3, forward primer PIC5E (5'-CTGTGGGT-TCATGTGGGATCAGGGT-3' (which corresponds to SEQ ID NO:22)) and reverse primer PIC58 (5'-GGGGACAGCA-GAAACGGAACGTCA-3' (which corresponds to SEQ ID NO:23)) were used to amplify the full-length porcine ICAM-3 cDNA. The two resulting PCR products were subcloned into pCR2.1 vector respectively, sequenced and designated as pPIC3L and pPIC3S.

Genomic PCR: The QIAamp DNA blood Mini kit (Qiagen Inc., Valencia, Calif.) was used for isolation of DNA from porcine MDDCs, whole blood or PBMC. The primers used for the amplification of the porcine ICAM-3 genomic sequence were designed based on the full-length porcine ICAM-3 cDNA sequence identified from this study. Forward primer PIC53 (5'-CCCACGAGATTGTCTG-CAACGTGACC-3' (which corresponds to SEQ ID NO:24)) and reverse primer PIC58 are located in exon 4 and exon 7, respectively. KOD high fidelity DNA polymerase (Novagen, Madison, Wis.), TaKaRa LA Taq with GC Buffer (TaKaRa, Japan) or Advantage Genomic PCR Kit (Clontech, Palo Alto, Calif.) were used for the genomic PCR amplification according to the respective manufacturer's protocols. The PCR products of the porcine ICAM-3 genomic fragments were sequenced directly for both strands.

Sequence analyses: Analyses of the DNA and amino acid sequences were performed using Lasergene package (DNASTAR Inc., Madison, Wis.).

Results and Discussion

Generation of porcine MDDCs from cultured adherent PBMC: Adherent porcine CD14-positive PBMC cells were grown in medium supplemented with rpGM-CSF and rpIL-4. Single and aggregated veiled-shaped cells first appeared after one day of culture. Larger cells with irregular shape with long veils protruding from the cell body and cluster formation were apparent at day 7, indicating the generation of porcine MDDCs. Cultured cells without addition of rpGM-CSF and rpIL-4 did not show any morphological change or aggregation.

Cloning and characterization of two isoforms of porcine ICAM-3 cDNA: Although the partial porcine ICAM-3 gene is reported Leeb and Muller, 2004, supra), the cDNA of porcine ICAM-3 has not been identified to date. Based on the predicted partial porcine ICAM-3 coding region, two primers PIC54 and PIC51 were designed and 5'- and 3'-RACE PCRs were performed using total RNAs extracted from porcine MDDCs. Since the reverse primer PIC54 for 5'-RACE PCR is located downstream of 3'-RACE PCR primer PIC51, the amplified 5'-RACE and 3'-RACE PCR products have a 55-nt overlapping region, thus covering the full-length sequence of the porcine ICAM-3.

Figure 10:
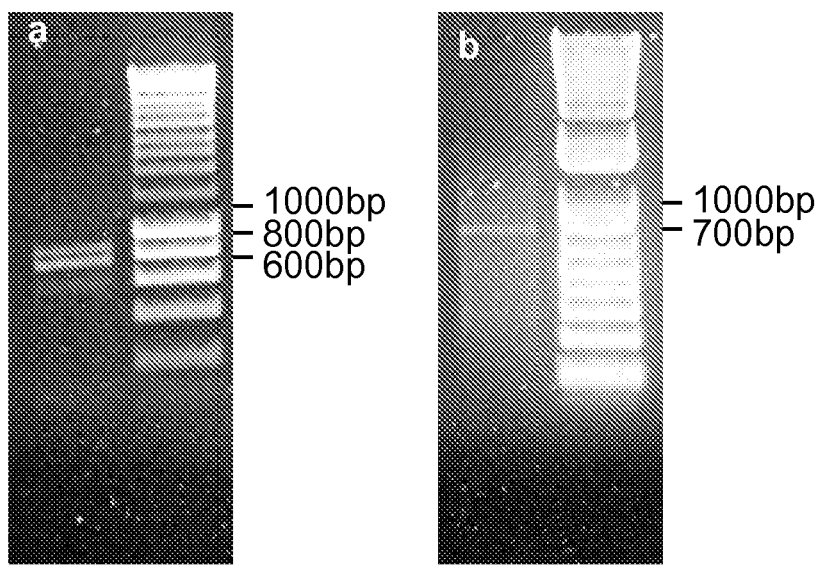

Two fragments with approximately 850 bp and 750 bp, respectively, were amplified from 5'-RACE PCR (FIG. 10(a)), whereas only one band of approximately 700 bp from the 3'-RACE PCR was visualized on a 1% agarose gel (FIG. 10(b)). Assembly and analyses of the resulting sequences identified two isoforms of porcine ICAM-3 cDNAs that are different at the 5'-end region. The full-length large and small isoforms of ICAM-3 were subsequently obtained by RT-PCR amplification using two primers complementary to both ends of the available sequence, respectively. Sequence analyses of the two isoform products verified the results from the assembly of 5'- and 3'-RACE products.

The large isoform (ICAM-3L) is 1,493 bp in length, with two open reading frames (ORFs) starting at nt position 13 or 258, respectively (FIGS. 11a and 11b). The first ORF encodes a 63-aa small peptide that does not overlap with the second ORF. The second ORF with 1,119 bp in length is predicted to encode the porcine ICAM-3, which is followed by 117 by 3' uncoding region, a polyadenylation signal at nt position 1452, and a poly(A) tail beginning at nt position 1469. The predicted ICAM-3 protein has a 34-aa putative signal peptide followed by 338 amino acids of the mature protein. The predicted 26-aa hydrophobic transmembrane domain, starting at aa position 321, is followed by a 26-aa putative cytoplasmic tail.

The small isoform (ICAM-3S) with 1,379 bp in length has 114-nt deletion beginning at nt position 145 when compared to the large isoform ICAM-3L (FIGS. 11a and 11b). The deletion starts in-frame from aa position 45 of the first ORF and precedes the ATG start codon of the second ORF, resulting in the fusion of the second ORF with the first truncated one. Therefore, the small isoform porcine ICAM-3S only encodes one ORF with 416 amino acids. Whether the small ORF in the large isoform porcine ICAM-3L is capable of expressing a functional peptide, or whether the single ORF in the small isoform ICAM-3S initiates at nt position 13, remain to be determined. Both isoforms share main coding region beginning from the putative signal peptide (FIGS. 11a and 11b).

Findings: The results show that the porcine ICAM-3 isoforms only consist of three Ig-like domains. Since the human, non-human primates and bovine ICAM-3s consist of five Ig-like domains that define them as a subfamily of the Ig gene superfamily, one would expect that porcine ICAM-3 should have the similar structure since, besides non-human primates, swine is the closest species to humans. Surprisingly, however, it was found that the cloned porcine ICAM-3 only encoded three extracellular Ig-like domains with intrachain disulfide bonds typical of Ig-like loops. Compared to the partial porcine ICAM-3 cDNA deduced from the reported partial gene, the existing three Ig-like domains are identical and recognized as domains 1-3. In addition, the highest sequence identity of each domain with the corresponding ones in porcine ICAM-1 and ICAM-2 also indicated that the cloned ICAM-3 harbors domains 1-3 (see Table 2 below) (C. J. Stocker et al., "Cloning of porcine intercellular adhesion molecule-1 and characterization of its induction on endothelial cells by cytokines," Transplantation 70:579-586 (2000); J. W. Godwin et al., "Characterization of pig intercellular adhesion molecule-2 and its interaction with human LFA-1," Am J Transplant. 4:515-525 (2004)). Similar to ICAM-1 and ICAM-2, the Ig-like domain 1 (D1) contains two putative disulfide bonds. Sequence comparisons between individual domains of porcine-human or porcine-bovine ICAM-3s revealed that both domain 2 (D2) and domain 3 (D3) are relatively conserved, 67% for D2 and 68.8% for D3 between porcine and human, and 71.4% for D2 and 66% for D3 between porcine and bovine. The D1 shows lower sequence identity between porcine and human as well as porcine and bovine. Interestingly, although bovine ICAM-3 consists of five Ig-like domains, its phylogenetic relationship with porcine ICAM-3 is closer than with primates, with 40.7% amino acid identity and forms an individual cluster from the primates ICAM-3s. This relationship suggests that bovine and porcine ICAM-3s evolved from a divergent pathway.

TABLE 2

Amino acid Sequence identities between porcine ICAM IgSF domains

| ICAM-3 | | Domain 1 | Domain 2 | Domain 3 |
| --- | --- | --- | --- | --- |
| ICAM-1 | Domain 1 | 24.4* | 8.2 | 8.5 |
| | Domain 2 | 5.6 | 59.2 | 16.0 |
| | Domain 3 | 12.2 | 15.3 | 31.9 |
| | Domain 4 | 12.2 | 18.4 | 13.8 |
| | Domain 5 | 6.7 | 9.2 | 12.8 |
| ICAM-2 | Domain 1 | 23.3 | 12.2 | 8.5 |
| | Domain 2 | 7.8 | 30.6 | 19.1 |
| ICAM-3 | Domain 1 | NA | 8.2 | 11.7 |
| | Domain 2 | NA | NA | 19.1 |
| | Domain 3 | NA | NA | NA |

*Percent amino acid sequence identities between Ig-like domains was calculated by Megalign program. Comparison of porcine ICAM-3 domains 1-3 with corresponding domains in porcine ICAM-1 or ICAM-2 was marked with bold.

Eight potential N-linked glycosylation sites are predicted to locate on the three domains (FIGS. 11a and 11b). The first site in D1 comprises conserved residues Asn57 and Ser59 identical to human ICAM-3 that were critical for LFA-1 binding (L. B. Klickstein et al., "Localization of the binding site on intercellular adhesion molecule-3 (ICAM-3) for lymphocyte function-associated antigen 1 (LFA-1)," J. Biol. Chem. 271:23920-23927 (1996)), implicating that the molecular interaction between LFA-1 and ICAM-3 in swine may have similar pattern with human ICAM-3.

The transmembrane domain (TMD) and cytoplasmic tail (CT) of porcine ICAM-3 show little conservation with those of porcine ICAM-1 and ICAM-2 or with human and bovine ICAM-3s. It is found that the serine residues in the CTs of human and bovine ICAM-3s are unique, and neither human, rat nor mouse ICAM-1 or ICAM-2 contain any serine residues in their CTs (F. Lozano et al., "Effect of protein kinase C activators on the phosphorylation and the surface expression of the CDw50 leukocyte antigen," Eur. J. Biochem. 203:321-326 (1992)). Interestingly, like human and bovine ICAM-3s, porcine ICAM-3 as well as porcine ICAM-1 and -2 all contain serine residues in their CTs. It has been shown that the serine residues on human ICAM-3 undergo transiently phosphorylation, leading to different intracellular signals and different roles in cell adhesion. Whether porcine ICAM members use phosphorylated serine residues for signal transduction like human ICAM-3 remain to be determined.

Figure 12A:
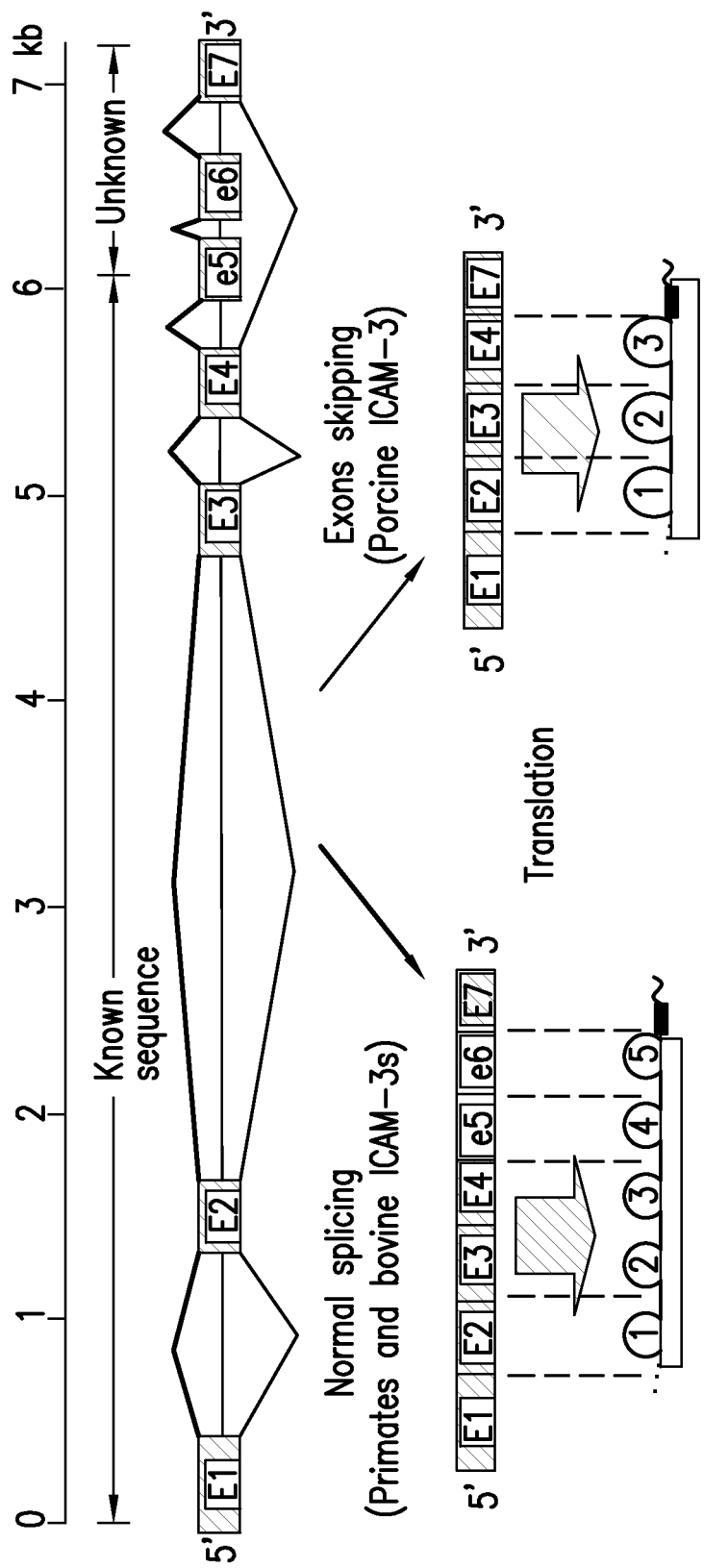
FIGS. 12a and 12b give the schematic representation of the proposed nonsense-associated altered splicing (NAS) of porcine ICAM-3 gene.

Each Ig-like domain of ICAM members is encoded by a distinct exon. In ICAM-1-deficient mice, complete exon skipping of murine ICAM-1 gene resulted in splicing variants with deletion of Ig-like domains 2, 3, and/or 4. However, the appearance of these variants may be due to pathological condition. The splicing isoforms of human ICAM-3 have not been reported, regardless of under pathological or normal physiological condition. Both human and bovine ICAM-3 genes have seven exons: exon 1 encodes the signal peptide, exons 2 through 6 encode D1 through D5, respectively, and exon 7 encodes TMD plus CT. The available sequence of porcine ICAM-3 gene is not complete and only contains region from exon 1 to partial exon 5. The porcine ICAM-3 isoforms identified from this study, with D4 and D5 deletion, are likely the results of continuous skipping of exons 5 and 6 of porcine ICAM-3 gene (FIG. 12a). Therefore, to better understand the splicing mechanism, cloning and sequencing the remaining unknown region of porcine ICAM-3 gene were undertaken.

Figure 12B:
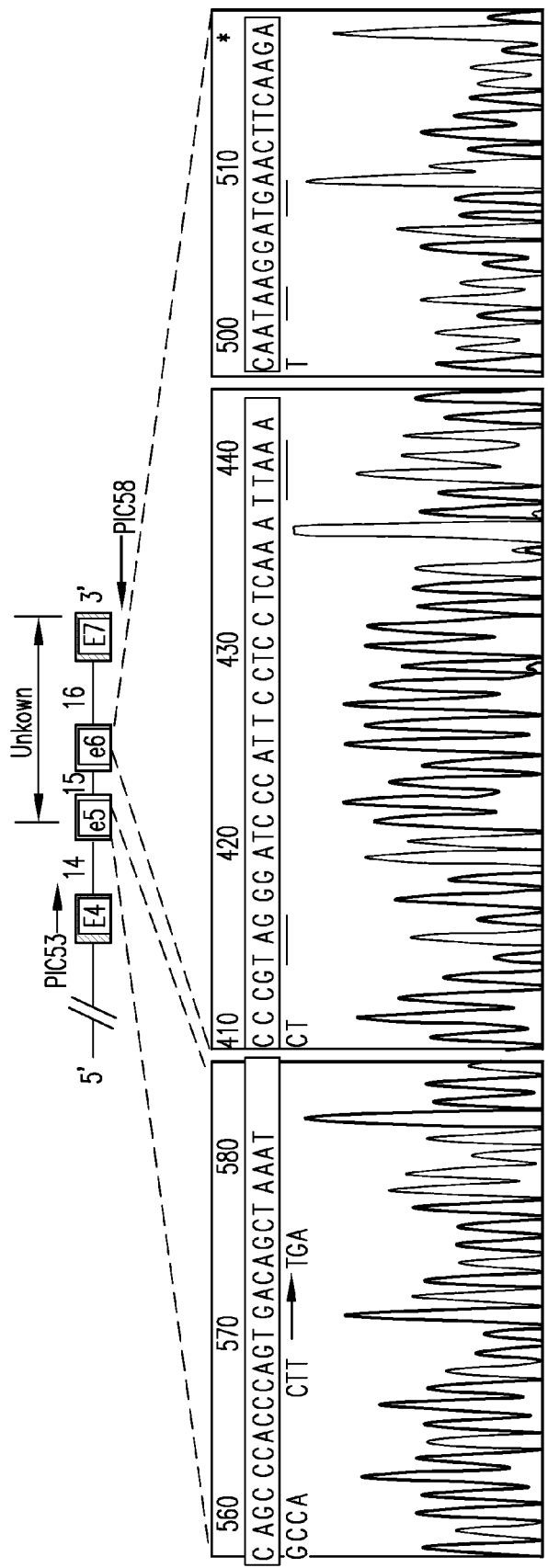

Cloning and characterization of the 3'-proximal region of porcine ICAM-3 gene: The TMD as well as the CT region of porcine ICAM-3 is presumably encoded by exon 7. The sequence of exon 7 was determined in this study from the porcine ICAM-3 cDNA, and thus was used to design a reverse primer for the genomic PCR in order to identify the unknown 3'-proximal region of the gene. To minimize unwanted mutations and to avoid any potential artificial deletion due to PCR amplification of the GC-rich region, three different commercial kits were used in the genomic PCR amplification. The resulting PCR products using all three PCR kits had the size of approximately 1.5 kb in length. Sequence analyses of these 1.5-kb PCR products revealed that they were all identical, and hence represents the 3'-proximal region of porcine ICAM-3 gene encompassing 72 bp of exon 4, all 273 bp of intron 4, all 255 by of exon 5, all 119 bp of intron 5, all 244 bp of exon 6, all 360 bp of intron 6, and 217 bp of exon 7 (FIG. 12b). When the previously reported partial porcine ICAM-3 gene was pieced together with the remaining sequence identified in this study, the organization of the complete porcine ICAM3 gene was showed as similar to that of human, non-human primates and bovine, which all contains seven putative exons spread over 7 kb. Exons 3 through 7 are clustered at the 3'-half of the gene.

The unknown boundary sequences of exons 5, 6 and 7 of porcine ICAM-3, respectively, were analyzed and the sequences compared with those in human and bovine (see Table 3 below). The boundary sequence of exon 7 including splice acceptor site (SAS) of intron 6 is similar to that in human. Exon 7 begins from two (GT) of the triplet (AGT) encoding the starting serine residue of TMD and CT region, which is consistent with the porcine ICAM-3 cDNA structure (FIGS. 11a and 11b). For exons 5 and 6, except for the splice donor site (SDS) of intron 6, other boundary sequences fulfill the consensus elements known to be involved in splicing and are conserved among the three species (Table 3, FIG. 12b).

Since most introns start from the sequence GT, the point mutation (G to A) at the putative SDS of intron 6 likely eliminates the splicing signal, and thus leading to the skipping of exon 6. Other alternative SDS was not found in the downstream sequence.

In the predicted coding region of exon 5, a significant 3-nt substitution, CTT to TGA, was observed at nt position 141 from the start sequence of the exon compared to the corresponding positions in human and bovine ICAM-3 genes. The mutation is in-frame but changes a leucine residue to a stop codon. The 255-bp size of the exon 5 in swine is the same as that in human and bovine.

The sequence of the putative exon 6 was more complicated. A 4-nt deletion and a 1-nt deletion were found at nt position 53 from the start sequence and nt position −7 from the end sequence of the exon, respectively. The 4-nt deletion results in a frame shift, and thus leading to four subsequent in-frame stop codons (FIG. 12b).

To make sure there is no missing RNA transcript encompassing exon 5 or 6, based on the obtained sequence information of exons 5 and 6, it was specifically attempted to amplify cDNA fragments with a forward primer PIC53 and several reverse primers complementary to the sequences of exon 5 or exon 6. No specific fragment was amplified, implying that the porcine ICAM-3 gene likely only produces mature mRNA in which the exons 5 and 6 had been skipped.

sion properties with porcine LFA-1 and DC-SIGN, thus playing similar roles in the corresponding porcine immune responses.

EXAMPLE 5

Cloning and Characterization of Porcine LSECtin cDNA and Gene

Materials and Methods

RNA extraction and reverse transcription PCR (RT-PCR): Healthy crossbred conventional pigs of 7 weeks of age were used for the collection of tissue samples. Pigs were maintained in an isolated room under experimental conditions. Total RNA was isolated from homogenized pig liver using the RNeasy mini kit (Qiagen Inc., Valencia, Calif.) followed by an RNase-free DNase I treatment. First-strand cDNA was synthesized from total RNA with SuperScript II reverse transcriptase (Invitrogen Corporation, Carlsbad, Calif.) using oligo-dT (Promega Corporation, Madison, Wis.) as the reverse primer. A pair of gene-specific primers, PLST-F (5'-TATGCCCAGAGCAGGGCACC-3' which corresponds to SEQ ID NO:31) and PLST-R (5'-GGGCTAGGTCAGCAGTTGTGC-3' which corresponds to SEQ ID NO:32), was designed for the amplification of

TABLE 3

Comparison of the intron/exon boundary sequence of exons 5-7 in human, bovine, and porcine ICAM-3 genes

| Specie | Exon 5 | | Exon 6 | | Exon 7 | |
|---|---|---|---|---|---|---|
| | SAS | SDS | SAS | SDS | SAS | SDS |
| Human | tttag/GCTTC CCTGT | /gtgag | cacag/ATGGT TGAGG | /gtgag | cacag/CTGGG | N/A |
| Bovine | tttag/GATTC CCTGT | /gtgag | cacag/ACGGC TCAAG | /gtgag | cacag/GTCGG | N/A |
| Porcine | attag/GCTTC CCTGT | /gtgag | cacag/ACGGC TCAAG | /ataag | cacag/GTCAG | N/A |

SAS: Splice Acceptor Site; SDS: Splice Donor Site; N/A: Not applicable
Intron sequences are represented by lowercase while exon sequences are represented by uppercase. Intron starting sequences "gt" and ending sequences "ag" are underlined. A point mutation (g to a) at the putative SDS of intron 6 in porcine ICAM-3 gene is indicated with bold italic letter.

The presence of in-frame stop codons or premature termination codons (PTC) in the exons 5 and 6 is linked to their exclusion from the mature mRNA of porcine ICAM-3. The phenomenon, known as nonsense-associated altered splicing (NAS), has been shown in a few disease-causing genes. However, on information and belief, species-associated NAS has never been reported previously. The porcine ICAM-3 isoforms lacking exons 5 and 6 identified from porcine MDDCs could be the native form of ICAM-3 RNA transcripts in porcine specie. The skipping of exon 5 is probably the consequence of a TGA nonsense mutation, whereas the skipping of exon 6 may come from four nonsense codons or a point mutation at the SDS of intron 6. Additional work which is not the scope of this study, such as mutagenesis analyses, is required to confirm NAS mechanism and to further identify the relevant splicing mechanism of porcine ICAM-3 gene.

The exact function of Ig-like domains 4 and 5 in human ICAM-3 protein has not been characterized. Domain 1, containing some critical residues including Asn57 and Ser59 in the first N-linked glycosylation site, is necessary and sufficient for LFA-1 binding. Domain 2 is believed to interact with human DC-SIGN. The cloned porcine ICAM-3 isoforms consist of both domains, which should retain the potential adhethe complete coding region of pLSECtin cDNA according to a porcine EST sequence with the GenBank accession number AK232603. PCR was performed in 50 µL reaction with an Advantage 2 PCR kit (Clontech, Palo Alto, Calif.) using the following PCR parameters: 94° C. for 2 min, 30 cycles at 94° C. for 15 sec, 60.0° C. for 30 sec and 72° C. for 90 sec, and a final incubation at 72° C. for 3 min. The obtained PCR products were individually excised, purified, and subsequently cloned into a pCR2.1 vector (Invitrogen Corporation, Carlsbad, Calif.) by TA cloning strategy followed by sequencing.

Genomic PCR and gene sequencing: The same primers PLST-F (SEQ ID NO:31) and PLST-R (SEQ ID NO:32) were used for one-step genomic PCR. Genomic PCR was performed with a Platinum PCR HiFi Supermix kit (Invitrogen Corporation, Carlsbad, Calif.) using 150 ng of the pig genomic DNA (purchased from Novagen, Madison, Wis.) in a total volume of 50 µL. The PCR condition was 35 cycles at 94° C. for 30 sec, 68° C. for 4 min with an initial denaturing of the template DNA at 94° C. for 2 min. The resulting fragment was cloned into a pCR2.1 vector (Invitrogen Corporation, Carlsbad, Calif.) by TA cloning strategy. The M13 forward and reverse primers together with a gene-specific primer PLST-E3F (5'-CAGGATCTACT-GAGGACAAACG-3' which corresponds to SEQ ID NO:33) were used for sequencing.

Tissue distribution of LSECtin detected by RT-PCR: Total RNA was isolated from ten homogenized pig tissues including spleen, duodenum, thymus, kidney, lung, lymph node, heart, bone marrow, liver and muscles using the RNeasy mini kit (Qiagen Inc., Valencia, Calif.) followed by an RNase-free DNase I treatment. cDNA was synthesized with SuperScript II reverse transcriptase (Invitrogen Corporation, Carlsbad, Calif.) using oligo-dT (Promega Corporation, Madison, Wis.) as the reverse primer. To avoid the contamination of genomic DNA, PCR was performed in 50 μL reactions with the Advantage 2 PCR kit (Clontech, Palo Alto, Calif.) using primer PLST-E67F (5'-GAGAGTCCGGTTCCAGAACAGCTCCT-3' which corresponds to SEQ ID NO:34) spanning the boundary between exon 6 and exon 7 and primer PLST-E89R (5'-TCCCCCAGATTCCAGTGGCTGAAG-3' which corresponds to SEQ ID NO:35) spanning the boundary of exon 8 and exon 9 of pLSECtin gene sequence that had been determined by genomic sequencing. The PCR parameters include 30 cycles at 95° C. for 20 sec, 68° C. for 1 min with an initial denaturing of the template DNA for 2 min. The house keeping gene, porcine glyceraldehyde 3-phosphate dehydrogenase (GAPDH), was also amplified using primers GAPDH5 (5'-GCTGAGTATGTCGTGGAGTC-3' which corresponds to SEQ ID NO:29) and GAPDH3 (5'-CTTCTGGGTGGCAGTGAT-3' which corresponds to SEQ ID NO:30) by PCR (95° C. for 1 min, 30 cycles at 95° C. for 20 sec, 55° C. for 20 sec, 68° C. for 40 sec and 72° C. for 3 min). The expected size of the PCR products was 303 bp for pLSECtin and 285 bp for porcine GAPDH, respectively.

Sequence and phylogenetic analyses: Analyses and alignment of DNA and amino acid sequences were performed using Lasergene package (DNASTAR Inc., Madison, Wis.).

Results and Discussion

Figure 13:
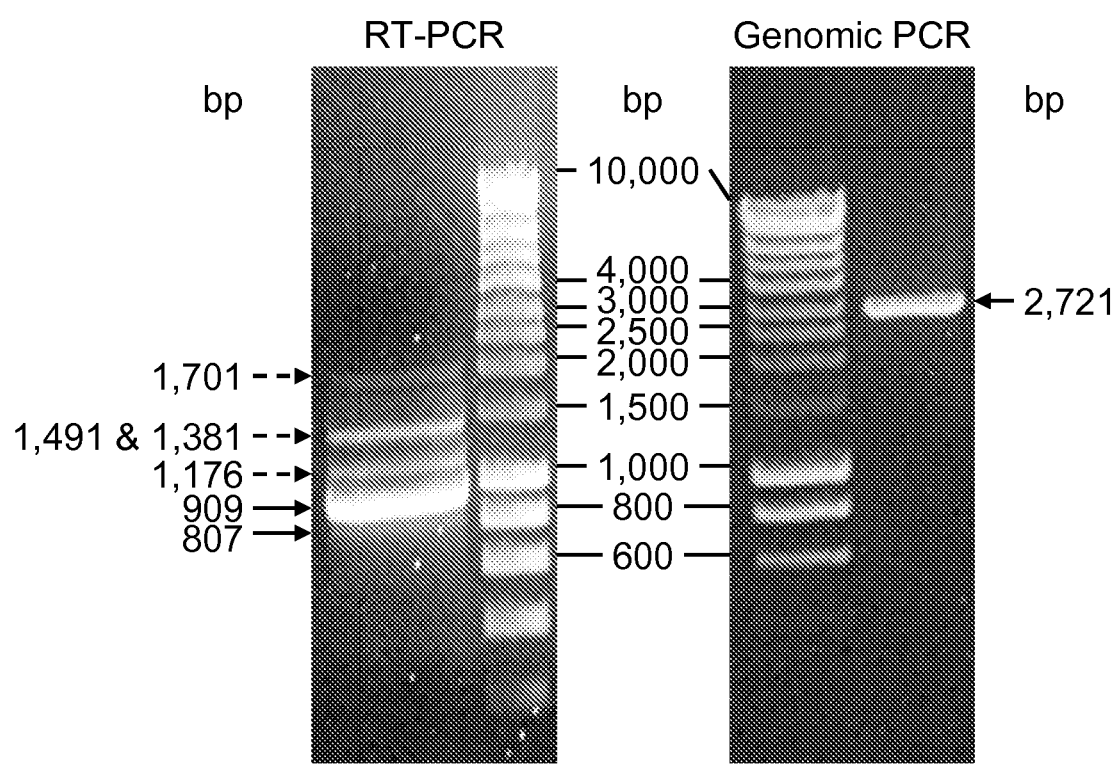
FIG. 13 depicts the amplification of the intermediate and final products (isoforms) of pLSECtin pre-mRNA during splicing from pig liver by RT-PCR and amplification of pLSECtin gene from pig genomic DNA by genomic PCR. Dashed-line arrows showed the spliced intermediate products; solid-line arrows indicated the isoforms and pLSECtin gene.

Molecular cloning and the structure of porcine LSECtin cDNA and gene: To find the porcine homologue of hLSECtin, a series of sequence similarity searches in the GenBank EST database was conducted. An EST sequence with the GenBank accession number AK232603 that shared significant homology with hLSECtin cDNA was found. Based on this sequence, we designed gene-specific primers and successfully amplified a 909-bp fragment containing the complete coding region of pLSECtin cDNA that is identical to the EST sequence from pig liver by RT-PCR (FIG. 13). A faint fragment represented another pLSECtin isoform lacking the transmembrane domain (807 bp) was also identified (FIG. 13). Besides these two isoforms, a series of higher-molecular-weight bands were amplified (FIG. 13), which would be recognized as the intermediate products of pLSECtin pre-mRNA during splicing (see discussion below). The pLSECtin gene (2721 bp) that had not been available on the public draft assembly of pig genome project was also cloned following the genomic PCR with the same pair of PCR primers (FIG. 13).

Figure 14A:
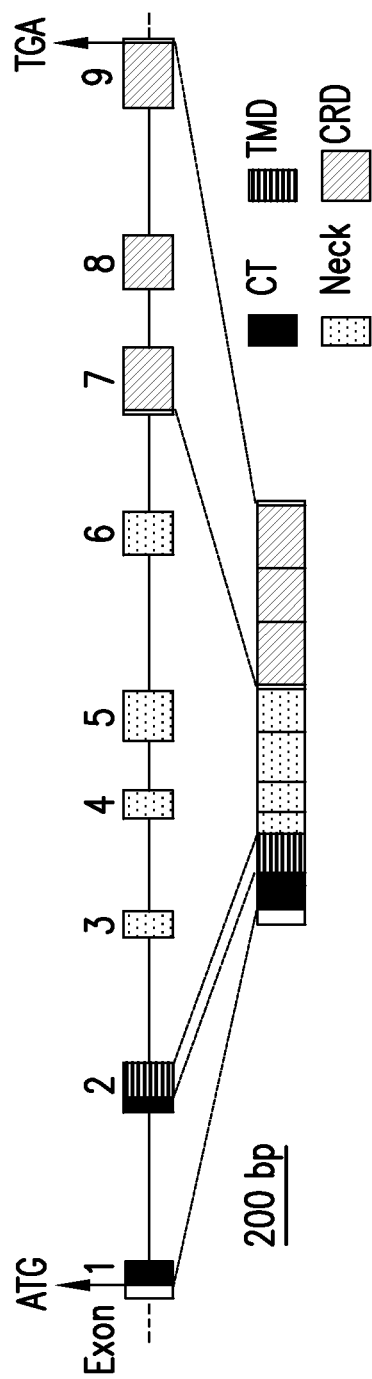

As illustrated in FIG. 14a, the pLSECtin gene was encoded by nine exons spanning the complete coding region of the gene in which exons 1 and 9 had undetermined sizes. The sequence of all the nine exons was fully identical to that of the cloned 909-bp cDNA as well as the pLSECtin EST, indicating the authenticity of the gene. The sizes of eight introns vary from 110 to 320 bp and all acceptor and donor sequences on the introns conform to the GT-AG rule. Like other type II C-type lectins, the putative coding region of pLSECtin encodes four domains, CT, TMD, neck and CRD, from the amino- to the carboxyl-terminus (FIGS. 14b and 14c). The 3' end of exon 1 and the 5' end of exon 2 encode the CT. The remaining part of exon 2 encodes the TMD. The neck region spans the entire exons 3 to 6 and the first 5 nucleotides of exon 7. The rest of exon 7, the entire exon 8 and the 5' end of exon 9 encode the CRD (FIG. 14a).

Figure 15A:
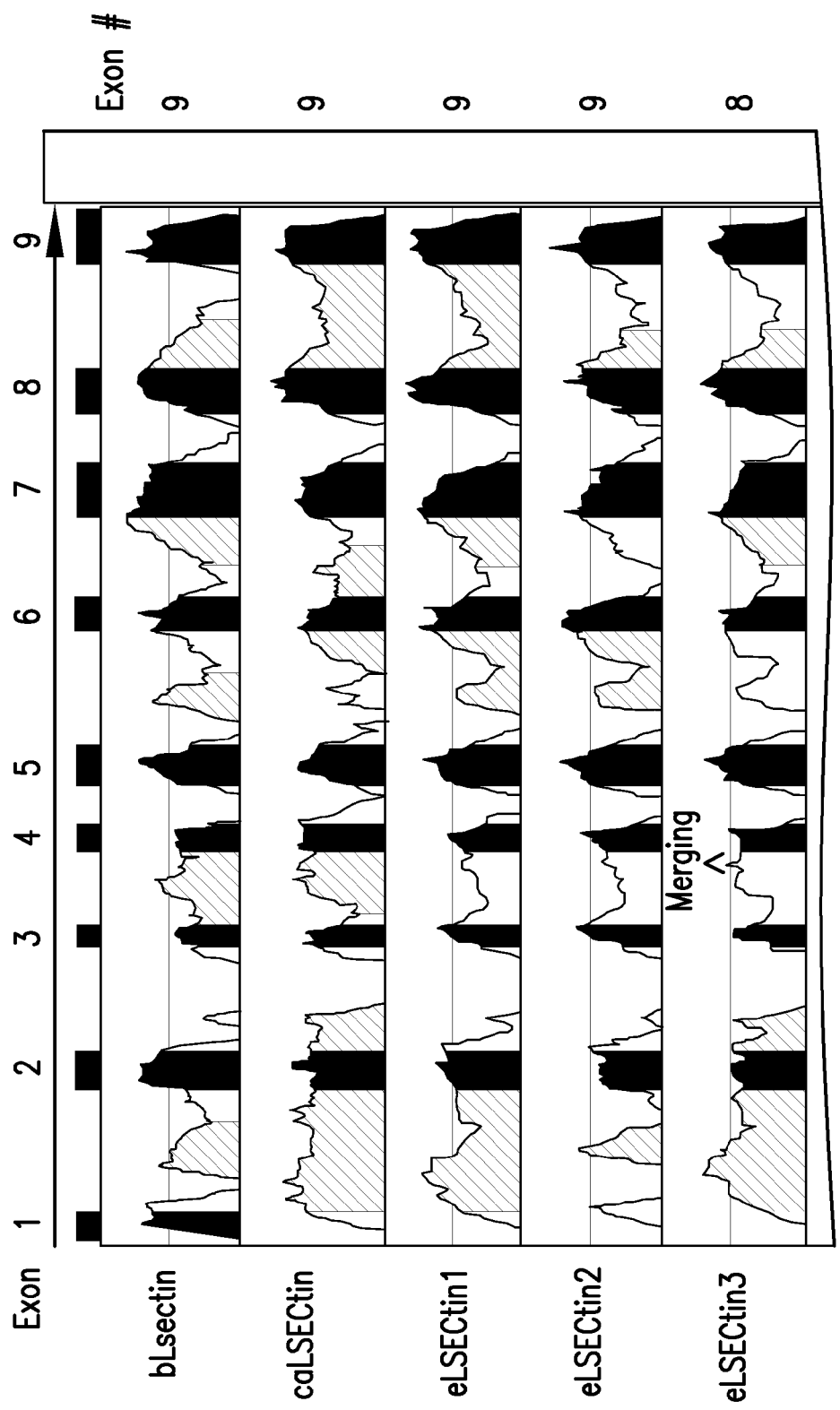
FIGS. 15a to 15c illustrate a comparison of the gene sequences and numbers of exons of pLSECtin gene with other LSECtin homologues as well as pDC-SIGN gene generated by the mVISTA program. Conserved regions between pairs of sequences are displayed as peaks of similarity (Y axis) relative to the positions of the gene sequence of pLSECtin (X axis). The dark boxes above the plots represent the nine exons of the pLSECtin gene. The peaks in the same dark shading indicate conserved regions within exons while the peaks shown by single hatching (also where it lacks any shading above the boxes) denote conserved regions within introns. The cutoff value of percent identity is set to 70%. The human and chimpanzee LSECtin pseudogenes lost their protein-coding ability due to a point mutation (G to A) at the proposed start codon. The two rhesus macaque LSECtin pseudogenes are unable to encode functional LSECtin proteins due to a 1-nt insertion or a 1-nt deletion leading to the frame shift. The exon 4 sequence of chimpanzee LSECtin gene is not available thus far. Abbreviations: porcine LSECtin (pLSECtin), bovine LSECtin (bLSECtin), canis LSECtin (caLSECtin), equine LSECtin (eLSECtin), human LSECtin (hLSECtin), human LSECtin pseudogene (hpLSECtin), chimpanzee LSECtin (chLSECtin), chimpanzee LSECtin pseudogene (chpLSECtin), rhesus macaque LSECtin pseudogene (rhpLSECtin), mouse LSECtin (mLSECtin), rat LSECtin (rLSECtin), opossum LSECtin (opLSECtin), platypus LSECtin (p1LSECtin), and porcine DC-SIGN (pDC-SIGN).
Figure 15B:
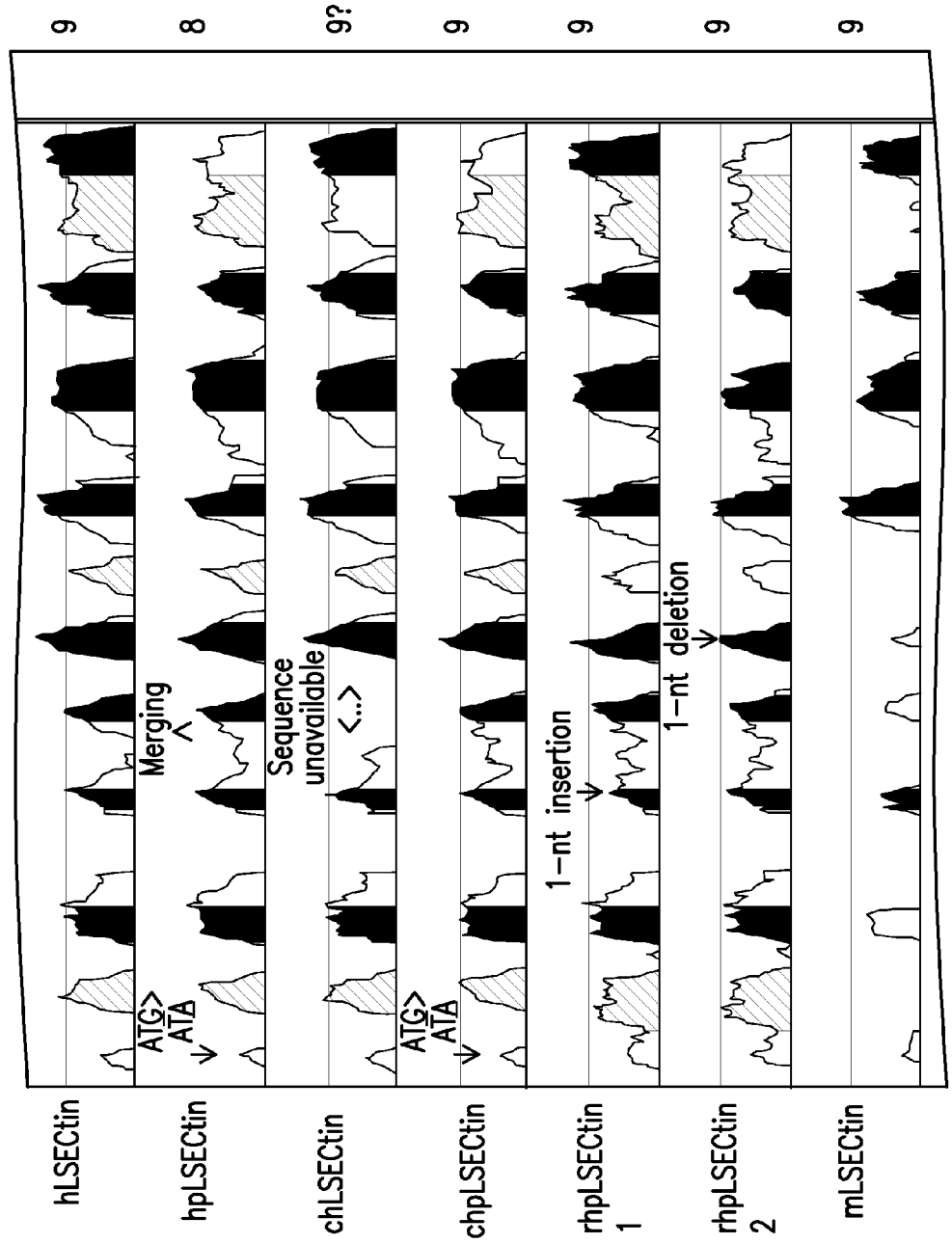
Figure 15C:
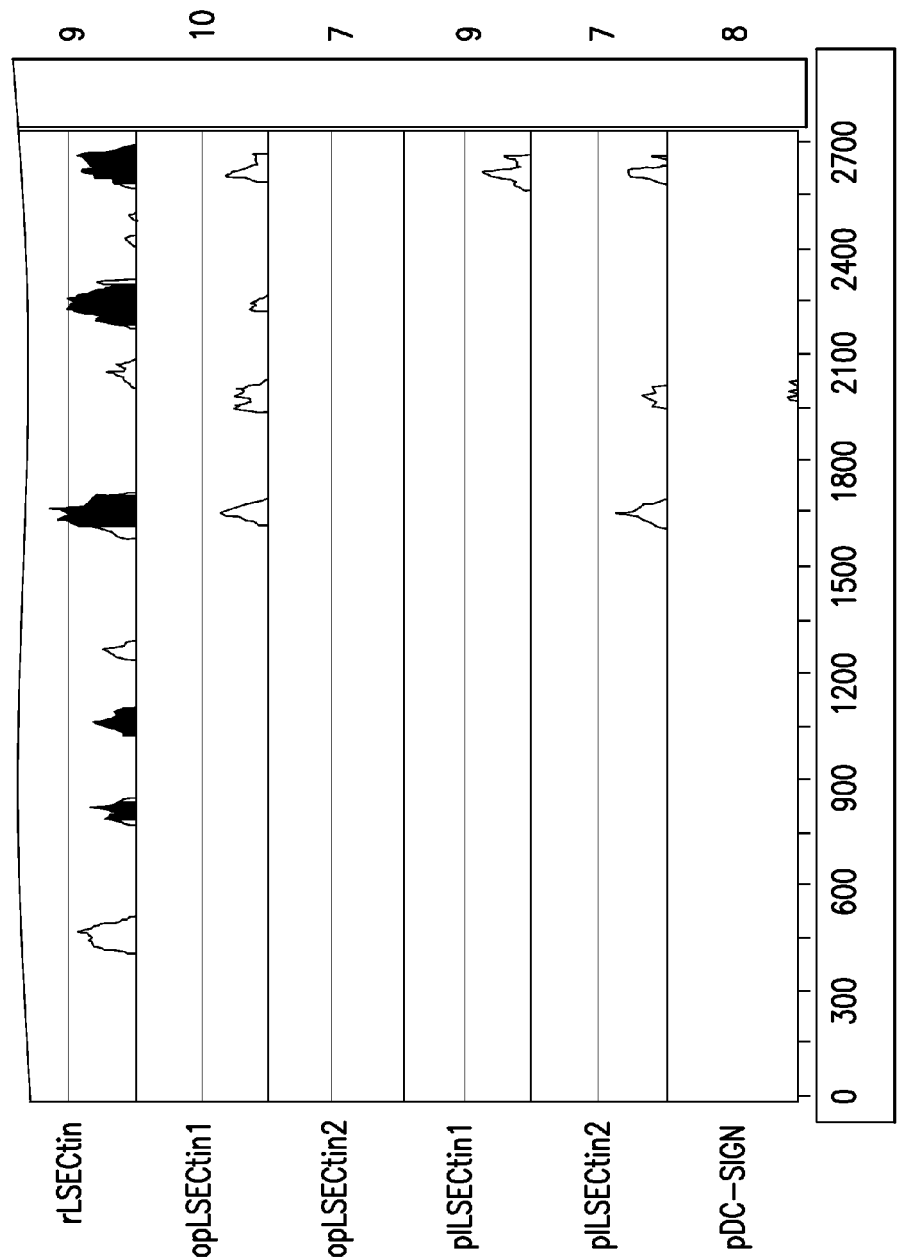

Comparison of the pLSECtin gene with other putative mammalian LSECtin homologues available from the genome databases: The pLSECtin gene shares a similar structure and size of nine exons including the localization of the four domains to the corresponding exons with the human as well as the predicted bovine, canis, mouse and rat LSECtin genes. Three LSECtin gene homologues, named as equine LSECtins 1 to 3 for purposes herein, were found in horse genome database. The equine LSECtin1 and LSECtin2 also have 9 exons with the same gene structure whereas equine LSECtin3 only contains 8 exons. The missing of one exon in equine LSECtin3 is caused by the fusion of two neck-domain-encoding exons (exons 3 and 4 corresponding to pLSECtin gene) of the canonical 9-exon-containing LSECtin gene into one. Similarly, the merging of exons 3 and 4 of the canonical 9-exon-containing LSECtin gene into one resulted in the total eight exons existing in the putative human LSECtin pseudogene. However, the lost of protein-coding ability of the human pseudogene, along with the chimpanzee LSECtin pseudogene, is due to a point mutation (G to A) at the proposed start codon ATG (FIGS. 15a-15c). Two rhesus macaque LSECtin homologues, LSECtin1 and LSECtin2 were predicted based upon the genomic sequencing data. However, in spite of the existence of nine exons, either of the homologue encodes a carboxyl terminus truncated protein product with CRD deletion due to a 1-nt insertion on exon 3 (for LSECtin1) or a 1-nt deletion on exon 5 (for LSECtin2), which are also recognized as the pseudogenes (FIGS. 15a-15c).

Except the two rhesus macaque LSECtin pseudogenes, all identified LSECtin homologues share an important structural feature in that the CRD always spans the last three exons. The DC-SIGN homologues in mammals identified so far have the same feature.

Pairwise comparison of the genomic sequences of pLSECtin with bovine, canis, equine, human, chimpanzee, rhesus macaque, mouse, rat, opossum or platypus using mVISTA program revealed that significant conservation in both exons (especially the last three exons encoding the CRD) and intron (especially introns 1, 3, 5, 6 and 8) sequences is present between pLSECtin and LSECtin homologues from domesticated animals and primates (FIGS. 15a-15c). Less conservation, presented mainly in exon sequences, was shown between pLSECtin and rodent LSECtin homologues while opossum and platypus LSECtins have the least conservation. No significant identity was found between pLSECtin and pDC-SIGN (FIGS. 15a-15c).

Sequence and phylogenetic analysis of pLSECtin encoding product with prediction of a multi-species-conserved microRNA target sequence at the 3'-untranslated region (3'-UTR) of LSECtin mRNAs: The 1,327-bp pLSECtin cDNA has two in-frame start codon ATG at nt position 10 or 37, respectively (FIGS. 14b and 14c). Compared to other LSECtin homologues without the first ATG at the corresponding position, the deduced pLSECtin protein is predicted to start at the second in-frame ATG and encompasses an open reading frame (ORF) of 873 nucleotides encoding a protein of 290 amino acids (FIGS. 14b and 14c). Porcine LSECtin protein is a putative type II transmembrane protein beginning from a 28-aa cytoplasmic tail followed by a predicted 22-aa TMD. The extracellular domain consists of a 111-aa neck region followed by a 129-aa CRD (FIGS. 14b and 14c). Two potential internalization motifs, YSKW and EE at aa position 6-9 and 14-15, were found within the CT, which are conserved in human, chimpanzee, bovine, ovine and canis LSECtins. Mutagenesis analysis has showed that the internalization ability of hLSECtin is dependent on the integrity of both motifs. Equine LSECtins 1 and 3, mouse, rat and two platypus LSECtin homologues also harbor the tyrosine-based motif as the potential internalization signal. The neck region of hLSECtin contains two potential N-linked glycosylation sites and has a typical heptad repeat pattern that is expected to form cc-helix coiled-coil structures. A recent study also revealed that hLSECtin exists as a disulfide-lined dimmer by two cysteine residues in the neck region (A. S. Powlesland et al., "A novel mechanism for LSECtin binding to Ebola virus surface glycoprotein through truncated glycans," J. Biol. Chem. 283(1):593-602 (2008)). All these features are identical in pLSECtin as well as other mammal LSECtins except equine LSECtin3, opossum and platypus LSECtins. It had been previously found that human DC-SIGN, L-SIGN, nonhuman primate DC-SIGN and mouse SIGNR1 contains variable repeated sequence within the neck region whereas the remaining mouse SIGNR members, except SIGNR2 and SIGNR6, together with porcine, bovine, ovine, canis and equine DC-SIGNs, do not have repeated sequence. The data suggested that the evolution of the neck region of LSECtin family members is less divergent than that of DC-SIGN family members.

The CRD of pLSECtin was the most conserved region shared by porcine and all the other LSECtin homologue proteins, containing the key residues that form $Ca^{2+}$— and carbohydrate-binding sites. Eight conserved cysteines predicted to form disulfide bonds were found in the CRD of all LSECtin homologues except opossum LSECtin1 that has an extra 119-aa tail. All LSECtin as well as DC-SIGN family members possesses five conserved amino acid residues, Glu260, Asn262, Asn268, Asn280 and Asp281 (aa position corresponding to pLSECtin), for calcium-binding site 2 and the common Glu-Pro-Asn sequence (EPN sequences; aa position 260-262) that are critical for binding mannose-, fucose- or galactose-containing oligosaccharides. However, three of the four residues (aa positions 233, 237, 263 and 269) forming calcium-binding site 1 are unique in LSECtin family members. All placental mammalian LSECtins share a unique Ala residue distinct from DC-SIGNs at aa 233 whereas the residue at aa 237 is variable among LSECtin homologues. All LSECtin members share the Asp residue instead of the conserved Asn residue at aa 263. The conserved Asp269 of C-type lectins is identical in most of the LSECtin proteins but is substituted by an Asn residue in human and chimpanzee LSECtin as well as opossum LSECtin1. In addition, there are 9 and 29 unique residues in the CRD shared by all mammalian LSECtin proteins and placental mammalian LSECtins, respectively. These unique substitutions suggested that the LSECtin family members would be expected to have different sugar-binding ability.

Recently, human LSECtin was shown to bind to a novel disaccharide, GlcNAcβ1-2Man, through the EPN motif and the two nearby residues Gly259 and Trp265 (Powlesland et al., 2008, supra). The contact between the GlcNAc residue and the side chain of Trp265 was predicted to be mediated by the packing of the indole ring of tryptophan against the methyl group of the N-acetyl substituent of GlcNAc (id.). However, although the Gly259 is conserved in all LSECtin proteins, only chimpanzee LSECtin shares the Trp265 with hLSECtin. The residue at this position is variable among other LSECtin proteins: Leu in pLSECtin, Met in bovine, ovine and canis LSECtins and Gln in three equine LSECtins.

MicroRNAs (miRNAs) are a class of small (~22 nt long) endogenous noncoding RNAs that bind to imperfectly complementary sits in the 3'-UTR of target mRNAs and thus repress mRNA expression (D. P. Bartel, "MicroRNAs: genomics, biogenesis, mechanism, and function," Cell 116 (2):281-97 (2004); B. R. Cullen, "Transcription and processing of human microRNA precursors," Mol. Cell 16(6):861-5 (2004)). Thousands of different miRNAs from multicellular organisms and some viruses have been identified and shown to have both tissue-specific and development-stage-specific expression, which is thought to regulate almost every biological process. It has been estimated that more than one third of human genes could be controlled by microRNAs (id.). MiRNA-mediated repression often requires perfect base pairing of the miRNA seed region (nt 2-7 from the miRNA 5'-end) to the 3'-UTR of an mRNA target sequence (Bartel, 2004, supra; Cullen, 2004, supra). Both miRNAs and their 3'-UTR binding sites are evolutionary conserved in many cases. Thus far, functional C-type lectin expression has not been linked to miRNA regulation. With the available information of 3'-UTR sequences from different mammalian LSECtin genes, an experiment was devised to see whether miRNA target sequences that are conserved across multiple mammalian species exist.

Using TargetScan program, a unique site located 27-nt upstream of the polyadenylation signal (AAUAAA) was found in the putative canis LSECtin mRNA that was predicted to be the target of a dog miRNA cfa-miR-350. The 7-nt sequence UUUGUGA on this site was fully conserved among porcine, bovine and ovine LSECtins as well as two equine homologues LSECtin1 and 3. Other conserved sequences at the 3'-UTR were observed to be less than 6-nt, which did not fulfill the proposed perfect base pairing of the miRNA seed region. Although the miR-350 homologues in pig, cattle, sheep and horse have not been available from miRBase, they should have the identical sequence due to the evolutionary conservation. Interestingly, an 8-nt sequence AACUGGAA at the same position in hLSECtin mRNA was also targeted by a human miRNA has-miR-145. This unique sequence was shared by chimpanzee LSECtin and equine LSECtin2 but not the other primate pseudogenes. No specific miRNAs recognizing the same site were found in rodent and non-placental LSECtin members, probably due to the limiting data of miRNAs in these species available from miRBase. The computer-based identification of a position-conserved and multi-species-conserved miRNA target sequence in LSECtin members from domesticated animals and primates are useful towards understanding the mechanism of potential miRNA-mediated regulation of LSECtin.

Phylogenetic analysis of the full-length encoding protein of all the available DC-SIGN, LSECtin and CD23 family members in mammalian species was thus performed to determine their divergence level and evolution relationship. They were divided into three individual clusters in which LSECtin family is more closely related to DC-SIGN family than to CD23 family. The LSECtins of domesticated animals including porcine, bovine, ovine, equine and canis were clustered together, which is similar to the evolutionary relationships of their DC-SIGN and CD23 proteins.

Figure 16:
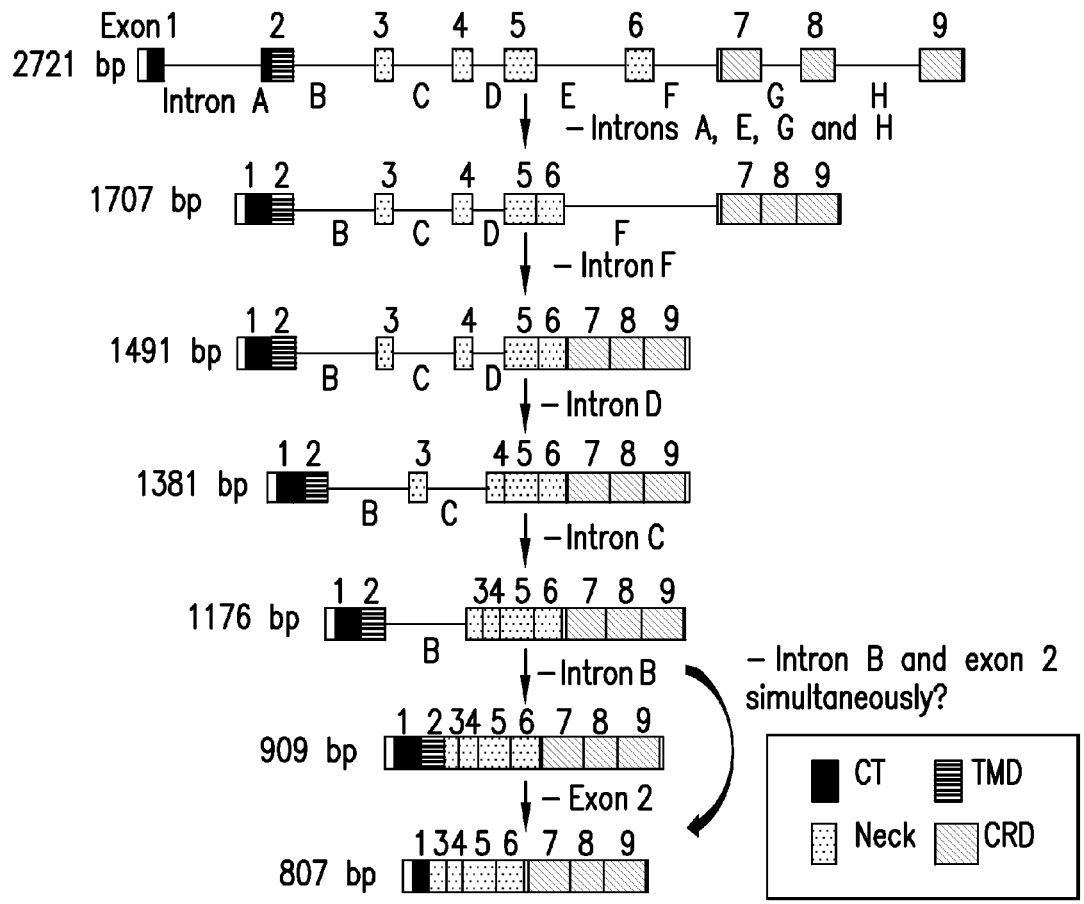
FIG. 16 shows a proposed order of intron removal from porcine LSECtin pre-mRNA. Boxes with numbers 1 to 9 represent the nine pLSECtin exon sequences. The eight intron sequences, letters A to H, are indicated by the black lines between the exons. The arrows show the splicing pathway. The gene, splicing intermediate products and isoforms detected by RT-PCR are indicated with their respective sizes shown on the left.

Identification of splicing intermediate products and proposed order of intron removal of pLSECtin pre-mRNA: When the coding region of pLSECtin cDNA from pig liver was amplified, the possible processing of pLSECtin pre-mRNA characterized by the appearance of a series of high-molecular-weight fragments in addition to the expected mature mRNA was observed (FIG. 13). Each of these fragments was excised and T-A cloned to determine the respective sequence. It turned out that these transcripts were splicing intermediate products of pLSECtin mRNA precursors with the sizes of 1707, 1491, 1381 and 1176 bp, respectively, which retained various introns compared to the determined pLSECtin gene (2721 bp). Based on the intron removals of these splicing intermediate products, a temporal order of the splicing pathway of pLSECtin pre-mRNA was proposed (FIG. 16). First, introns A, E, G and H seemed to be removed either simultaneously or in an order that could not be predicted from the RT-PCR result to yield an intermediate product of 1707 bp, leading to the integrities of the CRD encoded by the last three exons as well as the CT encoded by the first two exons. Further processing of the 1707-bp intermediate produces a 1491-bp pre-mRNA by splicing of intron F. Subsequent removal of intron D yields an mRNA that is 1381 bp. Intron C appears to be spliced at this point to yield the 1176-bp pre-mRNA that retains only intron B. The mature pLSECtin mRNA, detected as a 909-bp product, would be produced by removal of intron B. The processing of pLSECtin exons encoding the neck region appears to follow a strictly temporal and positional order by splicing of the relevant introns one-by-one, from 3' exon E to 5' exon B. Furthermore, exon 2 is removed from the mature mRNA product to yield an 807-bp isoform lacking the TMD. Alternatively, since exon 2 and intron B are linked together, the isoform may be generated by simultaneous splicing of them from the 1176-bp pre-mRNA (FIG. 16).

The temporal order of the splicing pathway was proposed based upon the fact that the amounts of the splicing intermediate products reached to the level that could be detected by RT-PCR, thus indicating that they occupied the majority in all the intermediate products. The detection was conducted in the liver to accurately reflect the processing pathways of these pre-mRNAs in vivo. Whether the processing of the exons encoding CRD and CT domain prior to the TMD and neck region observed here could also be present in other C-type lectins such as DC-SIGN and L-SIGN remains to be determined. The known DC-SIGN/L-SIGN mRNA as well as hLSECtin isoforms identified thus far exist as TMD-lacking or partial-tandem-neck-repeats-lacking variants due to the skipping of the exon encoding the TMD and/or the presence of cryptic splicing sites on exon encoding the neck region (A. Dominguez-Soto et al., "The DC-SIGN-related lectin LSECtin mediates antigen capture and pathogen binding by human myeloid cells," Blood 109(12):5337-45 (2007); S. Mummidi et al., "Extensive repertoire of membrane-bound and soluble dendritic cell-specific ICAM-3-grabbing nonintegrin 1 (DC-SIGN1) and DC-SIGN2 isoforms. Inter-individual variation in expression of DC-SIGN transcripts," J. Biol. Chem. 276 (35):33196-212 (2001)). This may be linked to the temporal order of the splicing in that different patterns of aberrant splicing occur during the later splicing events. Moreover, the variant neck-region tandem repeats of L-SIGN have been associated with the susceptibility of several infectious diseases such as SARS-CoV, HIV-1, HCV and *Mycobacterium tuberculosis* (U. S. Khoo et al., "DC-SIGN and L-SIGN: the SIGNs for infection," J. Mol. Med. 86(8):861-74 (2008)). Other factors including the "quality" of the donor/acceptor sites, splice enhancers or suppressors, the RNA secondary structures or the size of introns and exons may also contribute to controlling the order of intron removal (A. L. Lear et al., "Hierarchy for 5' splice site preference determined in vivo," J. Mol. Biol. 211(1):103-15 (1990); B. L. Robberson et al., "Exon definition may facilitate splice site selection in RNAs with multiple exons," Mol. Cell Biol. 10(1):84-94 (1990); A. J. McCullough and S. M. Berget, "G triplets located throughout a class of small vertebrate introns enforce intron borders and regulate splice site selection," Mol. Cell Biol. 17(8): 4562-71 (1997)). The identification of sequential splicing intermediate products of pLSECtin pre-mRNA in vivo may provide a good model to study how the splicing machinery selects the correct pairs of splice sites to ensure orderly intron removal in C-type lectins, and whether these could be linked to the interactions with the pathogens.

Figure 17:
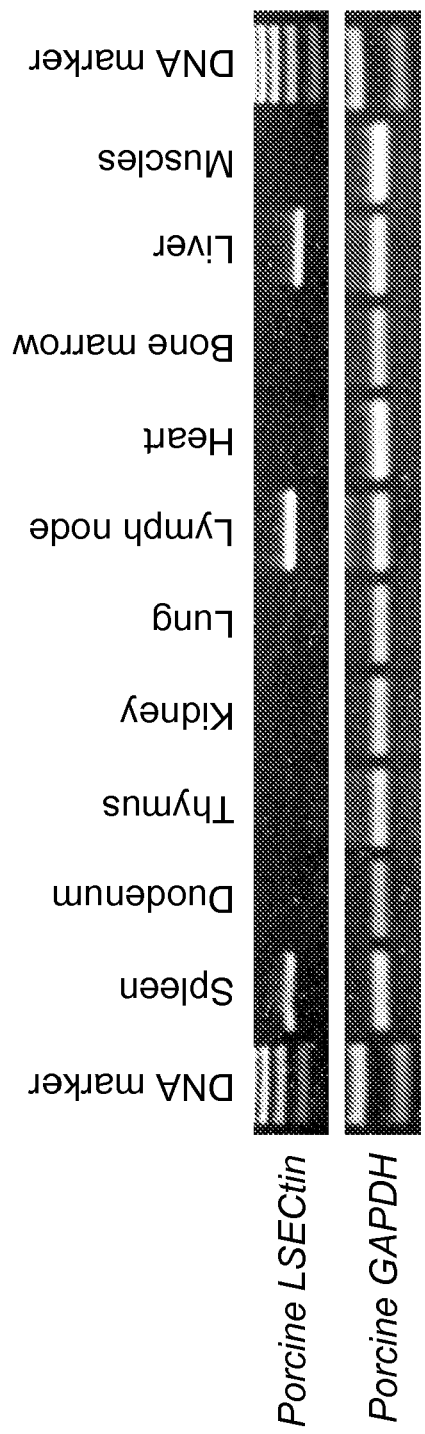
FIG. 17 demonstrates the detection of pLSECtin mRNA expression in selected pig tissues by RT-PCR. Pig tissue cDNA were used as templates in PCR reactions with primers PLST-E67F/PLST-E89R or porcine GAPDH-specific primers.

Tissue distribution of pLSECtin: Expression of pLSECtin mRNA was detected in spleen, lymph node and liver but not in duodenum, thymus, kidney, lung, heart, bone marrow or skeletal muscles of pig by RT-PCR (FIG. 17). The expression level in lymph node was the highest. It has been reported that hLSECtin is expressed not only on LSECs but also on monocyte-derived macrophages and dendritic cells (W. Liu et al., "Characterization of a novel C-type lectin-like gene, LSECtin: demonstration of carbohydrate binding and expression in sinusoidal endothelial cells of liver and lymph node," J. Biol. Chem. 279(18):18748-58 (2004); Dominguez-Soto et al., 2007, supra), lymph node and bone marrow sinusoids (T. Gramberg et al., "Interactions of LSECtin and DC-SIGN/DC-SIGNR with viral ligands: Differential pH dependence, internalization and virion binding," Virology 373(1):189-201 (2008)). However, the hLSECtin expression was not found on peripheral blood lymphocytes, NK cells, CD34+-derived endothelial-like cells (Dominguez-Soto et al., 2007, supra), liver Kupffer cells, thymus or placenta (Gramberg et al., 2008, supra). It was presently observed that the pLSECtin expression shares an analogous pattern with hLSECtin.

In the foregoing, there has been provided a detailed description of particular embodiments of the present invention for purpose of illustration and not limitation. It is to be understood that all other modifications, ramifications and equivalents obvious to those having skill in the art based on this disclosure are intended to be included within the scope of the invention as claimed.

SEQUENCE LISTING

<160> NUMBER OF SEQ ID NOS: 42

<210> SEQ ID NO 1
<211> LENGTH: 1069
<212> TYPE: DNA
<213> ORGANISM: Sus scrofa

```
<220> FEATURE:
<221> NAME/KEY: misc_structure
<222> LOCATION: (1)..(1069)
<223> OTHER INFORMATION: Nucleotide sequence of pDC-SIGN cDNA

<400> SEQUENCE: 1
ggagaggaac agagaggaga gaaggatggc agagatatgt gaccccaagg agccagagga      60
gaagacatgg acggggccag tattggttga gcgagatctt ggactactgc gcagattaag     120
gaactcacca gggtgtctga cttggcccct ccttctgctg ctgctcttcg tctcattggg     180
tttcttcatg ctcctggtga ccaccctggt tcaagtttcc aggatccacc agtctctgca     240
gagagagaga gagaccagca ggagacccac agcccaggag aagatacaat caagcctgga     300
taagttcctg cagcagatga cctggatgaa tgccaccctg ctggcctgt gccatccctg      360 cccctggcat tgggaattct tccagggaag atgctactta ttctcccaga cccagagtga     420
ctggaaatcc tctctctccg cctgtaagga cattggggcc cagctggtta tcatcaatag     480
cactgcggag cagaaattcc tgaagtcttg gtatgtcaga tataataaag ccacctggat     540
tggcctcagt gatgacacca atgaaggttc ctggcaatgg gtggacaaca gccccctcca     600
actcagcttc tggaaagaag gagaacccaa caatcacgga gatgaagact gtgcagaatt     660
gcacaacgat ggctggaatg atagcaaatg tacggtagaa aacgcctgga tctgtgagaa     720
gccctcgtct ccctgcccca tgctctgagg gccactgccc agcctcctac tccccatcag     780
cagagaatag gcaacaggcc ctcagctggt ttcccttttgg ctccaccctc ttccatcttt    840 acccttttggt gaattcccat ccccttcttg aacgacggtc ttttagatcc tacgagagat    900
tctgaaaccc ccttatcctc gaacccctcc ttccataggc tacaaaccct ctctcttcat     960
ctgcagatgg tctcagcagc ccctccgccc cgcccccccc atgacatccc cttaataaag    1020
tcacattgca ttatgtgttc caaaaaaaaa aaaaaaaaa aaaaaaaa                   1069

<210> SEQ ID NO 2
<211> LENGTH: 240
<212> TYPE: PRT
<213> ORGANISM: Sus scrofa
<220> FEATURE:
<221> NAME/KEY: MISC_FEATURE
<222> LOCATION: (1)..(240)
<223> OTHER INFORMATION: Deduced amino acid sequence of pDC-SIGN cDNA

<400> SEQUENCE: 2

Met Ala Glu Ile Cys Asp Pro Lys Glu Pro Glu Lys Thr Trp Thr
1               5                   10                  15

Gly Pro Val Leu Val Glu Arg Asp Leu Gly Leu Leu Arg Arg Leu Arg
            20                  25                  30

Asn Ser Pro Gly Cys Leu Thr Trp Pro Leu Leu Leu Leu Leu Phe
        35                  40                  45

Val Ser Leu Gly Phe Phe Met Leu Leu Val Thr Thr Leu Val Gln Val
    50                  55                  60

Ser Arg Ile His Gln Ser Leu Gln Arg Glu Arg Glu Thr Ser Arg Arg
65                  70                  75                  80

Pro Thr Ala Gln Glu Lys Ile Gln Ser Ser Leu Asp Lys Phe Leu Gln
                85                  90                  95

Gln Met Thr Trp Met Asn Ala Thr Leu Ala Gly Leu Cys His Pro Cys
            100                 105                 110

Pro Trp His Trp Glu Phe Phe Gln Gly Arg Cys Tyr Leu Phe Ser Gln
        115                 120                 125
```

```
Thr Gln Ser Asp Trp Lys Ser Ser Leu Ser Ala Cys Lys Asp Ile Gly
        130                 135                 140

Ala Gln Leu Val Ile Ile Asn Ser Thr Ala Glu Gln Lys Phe Leu Lys
145                 150                 155                 160

Ser Trp Tyr Val Arg Tyr Asn Lys Ala Thr Trp Ile Gly Leu Ser Asp
                165                 170                 175

Asp Thr Asn Glu Gly Ser Trp Gln Trp Val Asp Asn Ser Pro Leu Gln
            180                 185                 190

Leu Ser Phe Trp Lys Glu Gly Glu Pro Asn Asn His Gly Asp Glu Asp
        195                 200                 205

Cys Ala Glu Leu His Asn Asp Gly Trp Asn Asp Ser Lys Cys Thr Val
    210                 215                 220

Glu Asn Ala Trp Ile Cys Glu Lys Pro Ser Ser Pro Cys Pro Met Leu
225                 230                 235                 240

<210> SEQ ID NO 3
<211> LENGTH: 3438
<212> TYPE: DNA
<213> ORGANISM: Sus scrofa
<220> FEATURE:
<221> NAME/KEY: misc_feature
<222> LOCATION: (1)..(3069)
<223> OTHER INFORMATION: Nucleotide sequence of porcine DC-SIGN gene

<400> SEQUENCE: 3
gatggcagag atatgtgacc ccaaggagcc aggtagcccc agtgagggtg accccccatt      60
ctgggagtga tgatggggga ggacagggct cctgggtcct gaggggacgc gaggggggcct    120 agcatccagc ttgcaatcct gagagcaggg cccagcagtc ttccaagttc aaatgaatat    180
gctctgtcct attcagagga gaagacatgg acggggccag tattggttga gcgagatctt    240
ggactactgc gcagattaag gaactcacca ggtactaggg tggctggttc aggagtaggc    300
cactggggaa gggggtggta gggggtaggg tgggcaggg  tctgcctctg agcccctagc    360
gctgcccatc tgctggtcct gcagggtgtc tgacttggcc cctccttctg ctgctgctct    420
tcgtctcatt gggtttcttc atgctcctgg tgaccaccct ggttcaaggt gagtcagggg    480
ttgggggctt cgagtcctgg gtcccgttgg gttttctctc tgggatggtt tttgaccttt    540
tccctagtcc tgaaacctac tggggctggg gcatttggac tctgtgttgc ccctctgtgt    600
gactgggggc cagttactcc ccttctctgg acctgtttcc ttatgtgaaa tgtagctcat    660
cctcccctgt ggggagctta ggctgcactt gaaaatgaac ttgggagttc ccgttgtggc    720
acagtggtta cgaatccga ctaggaacca tgaggtttcg ggttcggtcc ctgcccttgc    780
tcagtgggtt aacgatcccg cgttgctgtg agctgtggtg tagattgcag atgcggctcg    840
gatcccgcgt tgctgtgggt ctggcatagg ccagtggcta cagctccaat tccacccta     900 acctgggaac ctccatatgc caccggagcg gcccaaagaa atagtaaaaa gacaaaaaaa    960
aaaaaaaaaa aagaaaaaa gaaatgaac ttggtgcagg cagagagttg gtgctcataa    1020
agggggaatt ttctgctctg ttgtagtttc caggatccac cagtctctgc agagagagag    1080
agagaccagc aggagaccca cagcccaggt gaaggatttg gaggacagct tctggagggg    1140
agagtgggag ggagctctga ggctgcatga ccttggacga gccaccacca caggagtgag    1200
ggcaggagta ggggagggga ccggatcccct gcatgaggtc ctggagactg gcaatgttgg    1260
gcaagtcact tttgaagcct cagttttctc gttcgtgtaa tgggctctcc aggtcacagt    1320
gagatccata cataatgttc tcatggggcc ctcactgtgc caagcacaca gtaggtgctt    1380
```

```
aataattgaa gtcctctccc tccacttgat gttgcacagg agaagataca atcaagcctg   1440
gataagttcc tgcagcagat gacctggatg aatgccaccc tgggtaatgg tcccacccca   1500
aggtcaagag gaagtcacgg gattgtggat ggggctggga cccacctttt gtagctgcca   1560
tactcaggag ggcagggcag agaggggtc ttttgagtgg gtttcttggg gccttgggga    1620
ctgggctgac agttggtccc tgggttccca agatctgatg cagggatctg ggctgggga    1680
gccaagtggc cgctctgtcc caacccctc cctcctcccc agctggcctg tgccatccct    1740
gcccctggca ttgggaattc ttccagggaa gatgctactt attctcccag acccagagtg   1800
actggaaatc ctctctctcc gcctgtaagg acattggggc ccagctggtt atcatcaata   1860
gcactgcgga gcaggtagac cgggcagggt tcctgttggg gctgggtcat agggctggtc   1920
aacaaagagc cttctgccac cctcctctgc cccctgagag atggaggtcc agtggatagc   1980
tggagatggg agggtaatgc agtcagggaa ggcttcctgg aggaggaacc ataacggact   2040
caggaaggtc acatgagaga agaaccagga tgggaggagc ccatatatgg atagaaaagg   2100
aactcaagaa tgccctcgaa gagttcccgt cctggctcag cagtgaacta atctgactct   2160
catccatgag gatgcaggtt cgattcctgg ccttgctctg tgggttaagg atccgacatt   2220
gctgtggtat aggacagcag ctacagctct gattcagtcc ctagcctggg aacctctata   2280
tgtggctggt cctaagaagc aagaaaaaaa agaatgccct tggaaccatc cataacgtag   2340
ggtcaactgg agatacaagt taacatatcc acacatgtat gggtacgaat acacattcac   2400
agcctacttg cacatgtgaa catacacaac ttgagtagag gctatggact agactgcaga   2460
aggaactttt gtgagaggca ggggacagag ggaacgtggg aagacatgtg acagatgtca   2520
ttgagggaat cttcccctaa tgcccttct caccccaccc cagaaattcc tgaagtcttg    2580
gtatgtcaga tataataaag ccacctggat tggcctcagt gatgacacca atgaaggttc   2640
ctggcaatgg gtggacaaca gcccctcca actcaggtga cctcccagtg acaatggccc    2700
aggaaggggt gggcagggaa aaacccacc tttcccaaac caggggtgct cagattctgg    2760
gactgaaaag taccacctga agagcttggt gaagatgcag cgtcccgcct ccacgctgct   2820
gttggggac ggggaggggg tctgagtcag tacgggccca ggaacctgca tttttacttt    2880
gccagagctg attctgatgg aggtggtatt tgagcccaca ttttgaaacc accacccct    2940
ggctggtacc tggcaatcaa ctgccacagc ctagggacag cttctccaag gggggtggg    3000
gtggaggggt gggttctggg tagagtaggg gtcccagagc tctgatgggg ttcacagctt   3060
ctggaaagaa ggagaaccca acaatcacgg agatgaagac tgtgcagaat tgcacaacga   3120
tggctggaat gatagcaaat gtacggtaga aaacgcctgg atctgtgaga agccctcgtc   3180
tccctgcccc atgctctgag ggccactgcc cagcctccta ctccccatca gcagagaata   3240
ggcaacaggc cctcagctgg tttcccttg gctccaccct cttccatctt taccctttgg    3300
tgaattccca tccccttctt gaacgacggt cttttagatc ctacgagaga ttctgaaacc   3360
cccttatcct cgaaccctc cttccatagg ctacaaaccc tctctcttca tctgcagatg    3420
gtctcagcag cccctccg                                                 3438

<210> SEQ ID NO 4
<211> LENGTH: 1493
<212> TYPE: DNA
<213> ORGANISM: Sus scrofa
<220> FEATURE:
<221> NAME/KEY: misc_feature
<222> LOCATION: (1)..(1493)
<223> OTHER INFORMATION: Nucleotide sequence of porcine ICAM-3 cDNA
```

-continued

```
<400> SEQUENCE: 4
gcctgtgggt tcatgtggga tcagggttta actgaggtct gccctctcag aggcttgcca      60
gagccttcca ccccattggg cccccaact  cggaaccccg ggggggacag agtatcccct     120
gcccctcccc aggactggac aaggtgcggc cctggactg  cagccttcgt aactgcagtg     180
actgtgcttc cttccctgg  gtgactcgct tgctccgtgg tagccagcac ctcattaagg     240
caacttcctc ctgcaggatg ccaccatgg  tgccatcgtg gctgccgtcc ggggcctact     300
ggattttcct catctctctg cttctagttg cctgtctact accccaggt  gctcaggggc     360
aggagttcca gatgagagtg gagctgcagc ccccagcagt gcttcctgga gagtctgtct     420
tggtaaactg cagtacagat tgcctccatg ctaaactcat ctccgtagag acgtacctac     480
tctgggagcc ggtgggcagt ggccggggct gggcagcctt ccaactcaac aatgtgactg     540
gtgacaccca gttcttctgc tttggcctct gcgatgactt ccagatagta agatcctcta     600
acatcaccat ctaccggttc ccagagcgcg tggaactggc ccctctgccc ccctggcacc     660
ccttggacaa gcccctcctc ctgagttgcc tcttgtctgg cggagctccc agggcccacc     720
tcacggtggc gctgttcaag ggggaggaag agctgggccg gcagccagca gcaaaggggg     780
agcccaccga agtcacggtc acagtgtccg cgagcagaga cgaccacggc gccaatttct     840
cttgccgcac agaattggac ctgcggtctc aagggctggg actgttccag aacagttctg     900
cccccagaaa gctccaaacc ttcgccatgc ccgtgacccc tcctcggcta gttgtcccac     960
agttttcgga agtggaaacg ttgtggcccg tggagtgcac cctggatggg gtcttcccag    1020
cctcggaagc ccaagtccaa ctggcgctgg ggaaccagag tctgaatccc gcagtcgtga    1080
gccacgggga caggctcacg gccacagcca ccgcgaaggc agagcagaaa ggcgcccacg    1140
agattgtctg caacatgacc ttaggtggca agaccctgga gacccgggag aacgtgacga    1200
tccaaagtca gaatcccctc gccatcacca ttagcctggg ggtgttagcg atcctgggtt    1260
tggtgattat cgctgcggcc ttaatgtgtg tcttccgggt gcagaagcag agtgacactt    1320
atcaagtgaa ccaaacgagt cctaggcaac ccaaagaggc tgcggcagca gagtgatcct    1380
gagcctcgga ccctcgggat actgcaaggc aaagacgaca ggggcttggc ggtatccccg    1440
aattccgcac taataaaggc tttaaaatca aaaaaaaaaa aaaaaaaaaa aaa           1493
```

<210> SEQ ID NO 5
<211> LENGTH: 372
<212> TYPE: PRT
<213> ORGANISM: Sus scrofa
<220> FEATURE:
<221> NAME/KEY: MISC_FEATURE
<222> LOCATION: (1)..(372)
<223> OTHER INFORMATION: Predicted protein sequence of porcine ICAM-3 cDNA

<400> SEQUENCE: 5

Met Ala Thr Met Val Pro Ser Trp Leu Pro Ser Gly Ala Tyr Trp Ile
1               5                   10                  15

Phe Leu Ile Ser Leu Leu Val Ala Cys Leu Leu Pro Gly Ala
            20                  25                  30

Gln Gly Gln Glu Phe Gln Met Arg Val Glu Leu Gln Pro Pro Ala Val
            35                  40                  45

Leu Pro Gly Glu Ser Val Leu Val Asn Cys Ser Thr Asp Cys Leu His
        50                  55                  60

Ala Lys Leu Ile Ser Val Glu Thr Tyr Leu Leu Trp Glu Pro Val Gly
65                  70                  75                  80

```
Ser Gly Arg Gly Trp Ala Ala Phe Gln Leu Asn Asn Val Thr Gly Asp
                85                  90                  95

Thr Gln Phe Phe Cys Phe Gly Leu Cys Asp Asp Phe Gln Ile Val Arg
            100                 105                 110

Ser Ser Asn Ile Thr Ile Tyr Arg Phe Pro Glu Arg Val Glu Leu Ala
            115                 120                 125

Pro Leu Pro Pro Trp His Pro Leu Asp Lys Pro Leu Leu Leu Ser Cys
            130                 135                 140

Leu Leu Ser Gly Gly Ala Pro Arg Ala His Leu Thr Val Ala Leu Phe
145                 150                 155                 160

Lys Gly Glu Glu Glu Leu Gly Arg Gln Pro Ala Ala Lys Gly Glu Pro
                165                 170                 175

Thr Glu Val Thr Val Thr Val Ser Ala Ser Arg Asp Asp His Gly Ala
            180                 185                 190

Asn Phe Ser Cys Arg Thr Glu Leu Asp Leu Arg Ser Gln Gly Leu Gly
            195                 200                 205

Leu Phe Gln Asn Ser Ser Ala Pro Arg Lys Leu Gln Thr Phe Ala Met
            210                 215                 220

Pro Val Thr Pro Pro Arg Leu Val Val Pro Gln Phe Ser Glu Val Glu
225                 230                 235                 240

Thr Leu Trp Pro Val Glu Cys Thr Leu Asp Gly Val Phe Pro Ala Ser
                245                 250                 255

Glu Ala Gln Val Gln Leu Ala Leu Gly Asn Gln Ser Leu Asn Pro Ala
            260                 265                 270

Val Val Ser His Gly Asp Arg Leu Thr Ala Thr Ala Thr Ala Lys Ala
            275                 280                 285

Glu Gln Lys Gly Ala His Glu Ile Val Cys Asn Met Thr Leu Gly Gly
            290                 295                 300

Lys Thr Leu Glu Thr Arg Glu Asn Val Thr Ile Gln Ser Gln Asn Pro
305                 310                 315                 320

Leu Ala Ile Thr Ile Ser Leu Gly Val Leu Ala Ile Leu Gly Leu Val
                325                 330                 335

Ile Ile Ala Ala Ala Leu Met Cys Val Phe Arg Val Gln Lys Gln Ser
            340                 345                 350

Asp Thr Tyr Gln Val Asn Gln Thr Ser Pro Arg Gln Pro Lys Glu Ala
            355                 360                 365

Ala Ala Ala Glu
    370

<210> SEQ ID NO 6
<211> LENGTH: 22
<212> TYPE: DNA
<213> ORGANISM: Sus scrofa
<220> FEATURE:
<221> NAME/KEY: misc_feature
<222> LOCATION: (1)..(22)
<223> OTHER INFORMATION: Oligonucleotide primer NF-05 used for detection
      of pDC-SIGN in pig tissues in which mixed base "s" is C + G and
      mixed base "m" is A + C

<400> SEQUENCE: 6
atcaaaastg mtgaggagca ga                                              22

<210> SEQ ID NO 7
<211> LENGTH: 20
<212> TYPE: DNA
<213> ORGANISM: Sus scrofa
```

```
<220> FEATURE:
<221> NAME/KEY: misc_feature
<222> LOCATION: (1)..(20)
<223> OTHER INFORMATION: Oligonucleotide primer NR-05 used for detection
      of pDC-SIGN in pig tissues in which mixed base "r" is A + G

<400> SEQUENCE: 7
catttgtcrt crttccagcc                                                   20

<210> SEQ ID NO 8
<211> LENGTH: 20
<212> TYPE: DNA
<213> ORGANISM: Sus scrofa
<220> FEATURE:
<221> NAME/KEY: misc_feature
<222> LOCATION: (1)..(20)
<223> OTHER INFORMATION: Oligonucleotide primer NR-06 used for detection
      of pDC-SIGN in pig tissues

<400> SEQUENCE: 8
aaccgcttca cctggatggg                                                   20

<210> SEQ ID NO 9
<211> LENGTH: 24
<212> TYPE: DNA
<213> ORGANISM: Sus scrofa
<220> FEATURE:
<221> NAME/KEY: misc_feature
<222> LOCATION: (1)..(24)
<223> OTHER INFORMATION: Oligonucleotide primer 5'-RACE PDR-1 used for
      detection of pDC-SIGN in pig tissues

<400> SEQUENCE: 9
cagaagctga gttggagggg gctg                                              24

<210> SEQ ID NO 10
<211> LENGTH: 25
<212> TYPE: DNA
<213> ORGANISM: Sus scrofa
<220> FEATURE:
<221> NAME/KEY: misc_feature
<222> LOCATION: (1)..(25)
<223> OTHER INFORMATION: Oligonucleotide primer 3'-RACE PDF-1 used for
      detection of pDC-SIGN in pig tissues

<400> SEQUENCE: 10
gccacctgga ttggcctcag tgatg                                             25

<210> SEQ ID NO 11
<211> LENGTH: 30
<212> TYPE: DNA
<213> ORGANISM: Sus scrofa
<220> FEATURE:
<221> NAME/KEY: misc_feature
<222> LOCATION: (1)..(30)
<223> OTHER INFORMATION: Oligonucleotide primer PCI-XHO used for
      detection of pDC-SIGN in pig tissues

<400> SEQUENCE: 11
agtctcgagc gccaccatgg cagagatatg                                        30

<210> SEQ ID NO 12
<211> LENGTH: 29
<212> TYPE: DNA
<213> ORGANISM: Sus scrofa
<220> FEATURE:
<221> NAME/KEY: misc_feature
<222> LOCATION: (1)..(29)
<223> OTHER INFORMATION: Oligonucleotide primer DCS3 used for detection
      of pDC-SIGN in pig tissues
```

-continued

```
<400> SEQUENCE: 12
tatctagatc agagcatggg gcagggaga                                            29

<210> SEQ ID NO 13
<211> LENGTH: 21
<212> TYPE: PRT
<213> ORGANISM: Sus scrofa
<220> FEATURE:
<221> NAME/KEY: MISC_FEATURE
<222> LOCATION: (1)..(21)
<223> OTHER INFORMATION: Peptide corresponding to regions within the CRD
      of porcine DC-SIGN

<400> SEQUENCE: 13

Val Asp Asn Ser Pro Leu Gln Leu Ser Phe Trp Lys Glu Gly Glu Pro
1               5                   10                  15

Asn Asn His Gly Cys
            20

<210> SEQ ID NO 14
<211> LENGTH: 16
<212> TYPE: PRT
<213> ORGANISM: Sus scrofa
<220> FEATURE:
<221> NAME/KEY: MISC_FEATURE
<222> LOCATION: (1)..(16)
<223> OTHER INFORMATION: Peptide corresponding to regions within the CRD
      of porcine DC-SIGN

<400> SEQUENCE: 14

Ala Glu Gln Lys Phe Leu Lys Ser Trp Tyr Arg Tyr Asn Lys Ala Cys
1               5                   10                  15

<210> SEQ ID NO 15
<211> LENGTH: 27
<212> TYPE: DNA
<213> ORGANISM: Sus scrofa
<220> FEATURE:
<221> NAME/KEY: misc_feature
<222> LOCATION: (1)..(27)
<223> OTHER INFORMATION: Oligonucleotide primer 1F used for detection of
      pDC-SIGN in pig tissues

<400> SEQUENCE: 15
gatggcagag atatgtgacc ccaagga                                              27

<210> SEQ ID NO 16
<211> LENGTH: 22
<212> TYPE: DNA
<213> ORGANISM: Sus scrofa
<220> FEATURE:
<221> NAME/KEY: misc_feature
<222> LOCATION: (1)..(22)
<223> OTHER INFORMATION: Oligonucleotide primer 4R used for detection of
      pDC-SIGN in pig tissues

<400> SEQUENCE: 16
cggaggggct gctgagacca tc                                                   22

<210> SEQ ID NO 17
<211> LENGTH: 27
<212> TYPE: DNA
<213> ORGANISM: Sus scrofa
<220> FEATURE:
<221> NAME/KEY: misc_feature
<222> LOCATION: (1)..(27)
<223> OTHER INFORMATION: Oligonucleotide primer 2F used for detection of
      pDC-SIGN in pig tissues
```

<400> SEQUENCE: 17
tcgtctcatt gggtttcttc atgctcc                                              27

<210> SEQ ID NO 18
<211> LENGTH: 28
<212> TYPE: DNA
<213> ORGANISM: Sus scrofa
<220> FEATURE:
<221> NAME/KEY: misc_feature
<222> LOCATION: (1)..(28)
<223> OTHER INFORMATION: Oligonucleotide primer 3F used for detection of
      pDC-SIGN in pig tissues

<400> SEQUENCE: 18
ctgcagagag agagagagac cagcagga                                             28

<210> SEQ ID NO 19
<211> LENGTH: 23
<212> TYPE: DNA
<213> ORGANISM: Sus scrofa
<220> FEATURE:
<221> NAME/KEY: misc_feature
<222> LOCATION: (1)..(23)
<223> OTHER INFORMATION: Oligonucleotide primer 4F used for detection of
      pDC-SIGN in pig tissues

<400> SEQUENCE: 19
tgcccctggc attgggaatt ctt                                                  23

<210> SEQ ID NO 20
<211> LENGTH: 22
<212> TYPE: DNA
<213> ORGANISM: Sus scrofa
<220> FEATURE:
<221> NAME/KEY: misc_feature
<222> LOCATION: (1)..(22)
<223> OTHER INFORMATION: Gene-specific primer PIC54 used for design
      based on sequence of partial porcine ICAM-3 gene

<400> SEQUENCE: 20
gcgtccaggt taagacacgc cg                                                   22

<210> SEQ ID NO 21
<211> LENGTH: 22
<212> TYPE: DNA
<213> ORGANISM: Sus scrofa
<220> FEATURE:
<221> NAME/KEY: misc_feature
<222> LOCATION: (1)..(22)
<223> OTHER INFORMATION: Gene-specific primer PIC51 used for design
      based on sequence of partial porcine ICAM-3 gene

<400> SEQUENCE: 21
tccgcgagca gagacgacca cg                                                   22

<210> SEQ ID NO 22
<211> LENGTH: 25
<212> TYPE: DNA
<213> ORGANISM: Sus scrofa
<220> FEATURE:
<221> NAME/KEY: misc_feature
<222> LOCATION: (1)..(25)
<223> OTHER INFORMATION: Forward primer PIC5E, used to obtain isoform of
      full-length porcine ICAM-3

<400> SEQUENCE: 22
ctgtgggttc atgtgggatc agggt                                                25

```
<210> SEQ ID NO 23
<211> LENGTH: 24
<212> TYPE: DNA
<213> ORGANISM: Sus scrofa
<220> FEATURE:
<221> NAME/KEY: misc_feature
<222> LOCATION: (1)..(24)
<223> OTHER INFORMATION: Reverse primer PIC58, used to obtain isoform of
      full-length porcine ICAM-3

<400> SEQUENCE: 23 gggacagca gaaacggaac gtca                                           24

<210> SEQ ID NO 24
<211> LENGTH: 26
<212> TYPE: DNA
<213> ORGANISM: Sus scrofa
<220> FEATURE:
<221> NAME/KEY: misc_feature
<222> LOCATION: (1)..(26)
<223> OTHER INFORMATION: Forward primer PIC53 designed based on the
      full-length porcine ICAM-3 cDNA sequence

<400> SEQUENCE: 24
cccacgagat tgtctgcaac gtgacc                                        26

<210> SEQ ID NO 25
<211> LENGTH: 19
<212> TYPE: DNA
<213> ORGANISM: Sus scrofa
<220> FEATURE:
<221> NAME/KEY: misc_feature
<222> LOCATION: (1)..(19)
<223> OTHER INFORMATION: Oligonucleotide primer Nco-DCS-5 used for
      detection of pDC-SIGN in pig tissues

<400> SEQUENCE: 25
ataccatggc agagatatg                                                19

<210> SEQ ID NO 26
<211> LENGTH: 30
<212> TYPE: DNA
<213> ORGANISM: Sus scrofa
<220> FEATURE:
<221> NAME/KEY: misc_feature
<222> LOCATION: (1)..(30)
<223> OTHER INFORMATION: Oligonucleotide primer Xho-DCS-3 used for
      detection of pDC-SIGN in pig tissues

<400> SEQUENCE: 26
agtctcgagt cagagcatgg ggcagggaga                                    30

<210> SEQ ID NO 27
<211> LENGTH: 21
<212> TYPE: DNA
<213> ORGANISM: Sus scrofa
<220> FEATURE:
<221> NAME/KEY: misc_feature
<222> LOCATION: (1)..(21)
<223> OTHER INFORMATION: Oligonucleotide primer PDCS-E56F used for
      detection of pDC-SIGN in pig tissues

<400> SEQUENCE: 27
gaatgccacc ctggctggcc t                                             21

<210> SEQ ID NO 28
<211> LENGTH: 29
<212> TYPE: DNA
<213> ORGANISM: Sus scrofa
```

```
<220> FEATURE:
<221> NAME/KEY: misc_feature
<222> LOCATION: (1)..(29)
<223> OTHER INFORMATION: Oligonucleotide primer PDCS-E78R used for
      detection of pDC-SIGN in pig tissues

<400> SEQUENCE: 28
gggttctcct tctttccaga agctgagtt                                        29

<210> SEQ ID NO 29
<211> LENGTH: 20
<212> TYPE: DNA
<213> ORGANISM: Sus scrofa
<220> FEATURE:
<221> NAME/KEY: misc_feature
<222> LOCATION: (1)..(20)
<223> OTHER INFORMATION: Primer GAPDH5 for amplifying porcine
      glyceraldehyde 3-phosphate dehydrogenase gene

<400> SEQUENCE: 29
gctgagtatg tcgtggagtc                                                  20

<210> SEQ ID NO 30
<211> LENGTH: 18
<212> TYPE: DNA
<213> ORGANISM: Sus scrofa
<220> FEATURE:
<221> NAME/KEY: misc_feature
<222> LOCATION: (1)..(18)
<223> OTHER INFORMATION: Primer GAPDH3 for amplifying porcine
      glyceraldehyde 3-phosphate dehydrogenase gene

<400> SEQUENCE: 30
cttctgggtg gcagtgat                                                    18

<210> SEQ ID NO 31
<211> LENGTH: 20
<212> TYPE: DNA
<213> ORGANISM: Sus scrofa
<220> FEATURE:
<221> NAME/KEY: misc_feature
<222> LOCATION: (1)..(20)
<223> OTHER INFORMATION: Gene specific primer PLST-F for amplifying
      coding region of pLSECtin cDNA

<400> SEQUENCE: 31
tatgcccaga gcagggcacc                                                  20

<210> SEQ ID NO 32
<211> LENGTH: 21
<212> TYPE: DNA
<213> ORGANISM: Sus scrofa
<220> FEATURE:
<221> NAME/KEY: misc_feature
<222> LOCATION: (1)..(21)
<223> OTHER INFORMATION: Gene-specific primer PLST-R for amplifying
      coding region of pLSECtin cDNA

<400> SEQUENCE: 32
gggctaggtc agcagttgtg c                                                21

<210> SEQ ID NO 33
<211> LENGTH: 22
<212> TYPE: DNA
<213> ORGANISM: Sus scrofa
<220> FEATURE:
<221> NAME/KEY: misc_feature
<222> LOCATION: (1)..(22)
<223> OTHER INFORMATION: Gene-specific primer PLST-E3F for porcine
      LSECtin cDNA
```

```
<400> SEQUENCE: 33
caggatctac tgaggacaaa cg                                              22

<210> SEQ ID NO 34
<211> LENGTH: 26
<212> TYPE: DNA
<213> ORGANISM: Sus scrofa
<220> FEATURE:
<221> NAME/KEY: misc_feature
<222> LOCATION: (1)..(26)
<223> OTHER INFORMATION: Primer PLST-E67F of pLSECtin gene sequence

<400> SEQUENCE: 34
gagagtccgg ttccagaaca gctcct                                          26

<210> SEQ ID NO 35
<211> LENGTH: 24
<212> TYPE: DNA
<213> ORGANISM: Sus scrofa
<220> FEATURE:
<221> NAME/KEY: misc_feature
<222> LOCATION: (1)..(24)
<223> OTHER INFORMATION: Primer PLST-E89R of pLSECtin gene sequence

<400> SEQUENCE: 35
tcccccagat tccagtggct gaag                                            24

<210> SEQ ID NO 36
<211> LENGTH: 1327
<212> TYPE: DNA
<213> ORGANISM: Sus scrofa
<220> FEATURE:
<221> NAME/KEY: misc_feature
<222> LOCATION: (1)..(1327)
<223> OTHER INFORMATION: Nucleotide sequence of pLSECtin cDNA

<400> SEQUENCE: 36
tttatatcta tgcccagagc agggcacctg cttaccatgg acactgccgg gtacagcaag      60
tgggacaaca agctggagga ggtccctgga gggcactggg acactgggga acagagatcc     120
ctcctcctgg cctttggtct ggtggtcgtc acagtcctgt gggccctcgt tctgagcatc     180
ctattttcca aggcctccac agagcgcggg gcgctgcttg ccaccaggga tctactgagg     240
acaaacgcct cgaagcagac ggcgactctg aaggtcttga aggaggaggt ccgagcctgc     300
aacagctgct gcctgggggt gcaggcgcag ctgcagacgg tgcacaccca gcttggagag     360
gcaaaggcga agctgttgga gcaggagagc gccctgaagg aactgagcga gcgcgtgacc     420
cagggcttgg ctgaagccgg tagggaccgt gagaacatcc gcagtgagct cttccgggag     480
ctggagagag tccggttcca gaacagctcc tgcgagcagt gccccaagtc gtggctgcca     540
ttccagggct cttgttactt tttctcggcg caaggggcca cgtgggtgga ggctcagagc     600
cactgcgagg gtgcgggcgc gcacctggtg attgttgggg gctggaggga gcagggcttc     660
ctgagtcgga atactgccgg ccgcggctac tggctgggcc tgagggctgt gcgcagggcg     720
cgcaaaatcc agagctacca gtgggtggat ggagtcccac tcagcttcag ccactggaat     780
ctgggggaac ccaatgactc tctggggcgc gaggactgca tcatgatgct acggacgggg     840
atgtggaatg acgcaccgtg caacagcaaa gacgacagct ggatctgcga agaggcac       900 aactgctgac ctagcccagt gcccagagc caagcccact ggcacttgtc caatcgcctg      960
agctgcttac tgccctggct ccgcccacca ctataatccc tcccactgct tccagcaaaa    1020
acaccccttc acccagagcc taggccaata actggacctc agctccaacc ccgctgcatc    1080
```

```
ccctcacccc atgagcctaa tgtatctaca ttcgctccaa atctgagct cctctgccct    1140 gtgatctggc cccatcaccc tccctaacca aggtcagtca cctcagggat ggagctgttt    1200
ggtttgcttg cttttacccc cagaagggg gcctcaaga tagagatttt gtgagctttc    1260
ttcacagccc tagggagcat caataaatga gaaatgaatc ttgaaaaaaa aaaaaaaaa    1320 aaaaaaa                                                              1327

<210> SEQ ID NO 37
<211> LENGTH: 299
<212> TYPE: PRT
<213> ORGANISM: Sus scrofa
<220> FEATURE:
<221> NAME/KEY: MISC_FEATURE
<222> LOCATION: (1)..(299)
<223> OTHER INFORMATION: Deduced amino acid sequence of pLSECtin cDNA

<400> SEQUENCE: 37

Met Pro Arg Ala Gly His Leu Leu Thr Met Asp Thr Ala Gly Tyr Ser
1               5                   10                  15

Lys Trp Asp Asn Lys Leu Glu Glu Val Pro Gly Gly His Trp Gly His
                20                  25                  30

Trp Gly Gln Arg Ser Leu Leu Ala Phe Gly Leu Val Val Thr
            35                  40                  45

Val Leu Trp Ala Leu Val Leu Ser Ile Leu Phe Ser Lys Ala Ser Thr
    50                  55                  60

Glu Arg Gly Ala Leu Leu Gly His Gln Asp Leu Leu Arg Thr Asn Ala
65                  70                  75                  80

Ser Lys Gln Thr Ala Thr Leu Lys Val Leu Lys Glu Val Arg Ala
                85                  90                  95

Cys Asn Ser Cys Cys Leu Gly Val Gln Ala Gln Leu Gln Thr Val His
            100                 105                 110

Thr Gln Leu Gly Glu Ala Lys Ala Lys Leu Leu Glu Gln Glu Ser Ala
        115                 120                 125

Leu Lys Glu Leu Ser Glu Arg Val Thr Gln Gly Leu Ala Glu Ala Gly
130                 135                 140

Arg Asp Arg Glu Asn Ile Arg Ser Glu Leu Phe Arg Glu Leu Glu Arg
145                 150                 155                 160

Val Arg Phe Gln Asn Ser Ser Cys Glu Gln Cys Pro Lys Ser Trp Leu
                165                 170                 175

Pro Phe Gln Gly Ser Cys Tyr Phe Phe Ser Ala Gln Gly Ala Thr Trp
            180                 185                 190

Val Glu Ala Gln Ser His Cys Glu Gly Ala Gly Ala His Leu Val Ile
        195                 200                 205

Val Gly Gly Leu Glu Glu Gln Gly Phe Leu Ser Arg Asn Thr Ala Gly
210                 215                 220

Arg Gly Tyr Trp Leu Gly Leu Arg Ala Val Arg Arg Ala Arg Lys Ile
225                 230                 235                 240

Gln Ser Tyr Gln Trp Val Asp Gly Val Pro Leu Ser Phe Ser His Trp
                245                 250                 255

Asn Leu Gly Glu Pro Asn Asp Ser Leu Gly Arg Glu Asp Cys Ile Met
            260                 265                 270

Met Leu Arg Thr Gly Met Trp Asn Asp Ala Pro Cys Asn Ser Lys Asp
        275                 280                 285

Asp Ser Trp Ile Cys Glu Lys Arg His Asn Cys
290                 295
```

```
<210> SEQ ID NO 38
<211> LENGTH: 63
<212> TYPE: PRT
<213> ORGANISM: Sus scrofa
<220> FEATURE:
<221> NAME/KEY: MISC_FEATURE
<222> LOCATION: (1)..(63)
<223> OTHER INFORMATION: Peptide encoded by porcine ICAM-3 cDNA

<400> SEQUENCE: 38

Met Trp Asp Gln Gly Leu Thr Glu Val Cys Pro Leu Arg Gly Leu Pro
1               5                   10                  15

Glu Pro Ser Thr Pro Leu Gly Pro Pro Thr Arg Asn Pro Gly Gly Asp
            20                  25                  30

Arg Val Ser Pro Ala Pro Pro Gln Asp Trp Thr Arg Cys Gly Pro Trp
        35                  40                  45

Thr Ala Ala Phe Val Thr Ala Val Thr Val Leu Pro Ser Pro Gly
    50                  55                  60

<210> SEQ ID NO 39
<211> LENGTH: 113
<212> TYPE: DNA
<213> ORGANISM: Sus scrofa
<220> FEATURE:
<221> NAME/KEY: misc_feature
<222> LOCATION: (1)..(113)
<223> OTHER INFORMATION: Nucleotide sequence of porcine ICAM-3 cDNA

<400> SEQUENCE: 39
tgcggcccct ggactgcagc cttcgtaact gcagtgactg tgcttccttc ccctgggtga      60
ctcgcttgct ccgtggtagc cagcacctca ttaaggcaac ttcctcctgc agg           113

<210> SEQ ID NO 40
<211> LENGTH: 28
<212> TYPE: DNA
<213> ORGANISM: Sus scrofa
<220> FEATURE:
<221> NAME/KEY: misc_feature
<222> LOCATION: (1)..(28)
<223> OTHER INFORMATION: Nucleotide sequence of porcine ICAM-3 gene

<400> SEQUENCE: 40
cagcccaccc agtgacagct aaatgcca                                         28

<210> SEQ ID NO 41
<211> LENGTH: 34
<212> TYPE: DNA
<213> ORGANISM: Sus scrofa
<220> FEATURE:
<221> NAME/KEY: misc_feature
<222> LOCATION: (1)..(34)
<223> OTHER INFORMATION: Nucleotide sequence of porcine ICAM-3 gene

<400> SEQUENCE: 41
cccgtaggga tcccattcct cctcaaatta aact                                  34

<210> SEQ ID NO 42
<211> LENGTH: 22
<212> TYPE: DNA
<213> ORGANISM: Sus scrofa
<220> FEATURE:
<221> NAME/KEY: misc_feature
<222> LOCATION: (1)..(22)
<223> OTHER INFORMATION: Nucleotide sequence of porcine ICAM-3 gene
```

```
<400> SEQUENCE: 42
caataaggat gaacttcaag at                                          22
```

What is claimed is:

1. An isolated nucleic acid molecule comprising:
   a) a nucleotide sequence encoding a fusion protein, wherein the fusion protein comprises pDC-SIGN protein or the carbohydrate recognition domain thereof linked to pLSECtin protein or the carbohydrate recognition domain thereof; or
   b) a complement of the nucleotide sequence of a).

2. The nucleic acid molecule according to claim 1, wherein the fusion protein comprises at least two proteins in which pLSECtin is linked to pDC-SIGN or to the carbohydrate recognition domain thereof.

3. The nucleic acid molecule according to claim 1, wherein the fusion protein further comprises at least one protein selected from the group consisting of
   (a) hDC-SIGN, (b) hL-SIGN, (c) hLSECtin, (d) the cytoplasmic tail of hDC-SIGN, hL-SIGN or hLSECtin, (e) the transmembrane domain of hDC-SIGN, hL-SIGN or hLSECtin, (f) the repeat neck region of hDC-SIGN, hL-SIGN or hLSECtin, and (g) a combination thereof.

4. The nucleic acid molecule according to claim 2, wherein the fusion protein further comprises at least one protein selected from the group consisting of
   (a) hDC-SIGN, (b) hL-SIGN, (c) hLSECtin, (d) the cytoplasmic tail of hDC-SIGN, hL-SIGN or hLSECtin, (e) the transmembrane domain of hDC-SIGN, hL-SIGN or hLSECtin, (f) the repeat neck region of hDC-SIGN, hL-SIGN or hLSECtin, and (g) a combination thereof.

5. The nucleic acid molecule according to claim 3, wherein the fusion protein contains the carbohydrate recognition domain of pDC-SIGN or pLSECtin and the cytoplasmic tail, the transmembrane domain or the repeat neck region of hDC-SIGN, hL-SIGN, hLSECtin or a combination thereof.

6. An isolated nucleic acid molecule comprising a nucleotide sequence encoding pDC-SIGN, wherein the nucleotide sequence comprises SEQ ID NO:1 or its complementary strand.

7. A plasmid or viral vector containing the nucleic acid molecule according to claim 1.

8. The plasmid or viral vector according to claim 7, wherein the vector is pTriEx-1.1 Neo.

9. An isolated, transfected cell or cell line expressing at least one or more proteins selected from the group consisting of pDC-SIGN, the carbohydrate recognition domain of pDC-SIGN, pLSECtin and the carbohydrate recognition domain of pLSECtin.

10. The cell or cell line according to claim 9, wherein the cell or cell line expresses a fusion protein.

11. The cell or cell line according to claim 10, wherein the fusion protein comprises at least two proteins in which pLSECtin is linked to pDC-SIGN or to the carbohydrate recognition domain thereof.

12. The cell or cell line according to claim 10, wherein the fusion protein further comprises at least one protein selected from the group consisting of
   (a) hDC-SIGN, (b) hL-SIGN, (c) hLSECtin, (d) the cytoplasmic tail of hDC-SIGN, hL-SIGN or hLSECtin, (e) the transmembrane domain of hDC-SIGN, hL-SIGN or hLSECtin, (f) the repeat neck region of hDC-SIGN, hL-SIGN or hLSECtin, and (g) a combination thereof.

13. The cell or cell line according to claim 11, wherein the fusion protein further comprises at least one protein selected from the group consisting of
   (a) hDC-SIGN, (b) hL-SIGN, (c) hLSECtin, (d) the cytoplasmic tail of hDC-SIGN, hL-SIGN or hLSECtin, (e) the transmembrane domain of hDC-SIGN, hL-SIGN or hLSECtin, (f) the repeat neck region of hDC-SIGN, hL-SIGN or hLSECtin, and (g) a combination thereof.

14. The cell or cell line according to claim 12, wherein the fusion protein contains the carbohydrate recognition domain of pDC-SIGN or pLSECtin and the cytoplasmic tail, the transmembrane domain or the repeat neck region of hDC-SIGN, hL-SIGN, hLSECtin or a combination thereof.

15. The cell or cell line according to claim 9, wherein the cell or cell line is selected from the group consisting of dendritic, macrophagic, monocytic, lymphocytic and trophoblastic cells.

16. The cell or cell line according to claim 9, wherein the cell or cell line is selected from the group consisting of BHK-21, MARC-145, PK-15, COS-7, VERO, CV-1, LLC-MK2, MDCK, MDBK, Raji B, CHO-K1, 3D4/31, IPEC-J2, THP-1, RAW 264.7, MA-104, 293T and ST cells.

17. A process for the production of a protein product, said process comprising: growing, under suitable nutrient conditions, prokaryotic or eucaryotic cells transfected with the nucleic acid molecule according to claim 1 in a manner allowing expression of said protein product, and isolating the desired protein product of the expression of said nucleic acid molecule.

18. A method for propagating a virus comprising:
   (a) providing a transfected cell or cell line according to claim 9;
   (b) growing the transfected cell or cell line in growth medium to form a culture;
   (c) inoculating said culture with the virus; and
   (d) incubating the inoculated culture under conditions effective to propagate the virus in the culture.

19. The method according to claim 18, further comprising lysing the inoculated culture to release intracellular virions and harvesting virus antigen.

20. The method according to claim 18, wherein step (a) provides a transfected cell or cell line expressing a fusion protein.

21. The method according to claim 20, wherein the fusion protein in step (a) comprises at least two proteins in which pLSECtin is linked to pDC-SIGN or to the carbohydrate recognition domain thereof.

22. The method according to claim 20, wherein the fusion protein in step (a) further comprises at least one protein selected from the group consisting of
   (a) hDC-SIGN, (b) hL-SIGN, (c) hLSECtin, (d) the cytoplasmic tail of hDC-SIGN, hL-SIGN or hLSECtin, (e) the transmembrane domain of hDC-SIGN, hL-SIGN or hLSECtin, (f) the repeat neck region of hDC-SIGN, hL-SIGN or hLSECtin, and (g) a combination thereof.

23. The method according to claim 21, wherein the fusion protein in step (a) further comprises at least one protein selected from the group consisting of
   (a) hDC-SIGN, (b) hL-SIGN, (c) hLSECtin, (d) the cytoplasmic tail of hDC-SIGN, hL-SIGN or hLSECtin, (e)

the transmembrane domain of hDC-SIGN, hL-SIGN or hLSECtin, (f) the repeat neck region of hDC-SIGN, hL-SIGN or hLSECtin, and (g) a combination thereof.

24. The method according to claim 22, wherein the fusion protein in step (a) contains the carbohydrate recognition domain of pDC-SIGN or pLSECtin and the cytoplasmic tail, the transmembrane domain or the repeat neck region of hDC-SIGN, hL-SIGN, hLSECtin or a combination thereof.

25. The method according to claim 18, wherein step (a) provides a transfected cell or cell line selected from the group consisting of dendritic, macrophagic, monocytic, lymphocytic and trophoblastic cells.

26. The method according to claim 18, wherein step (a) provides a transfected cell or cell line selected from the group consisting of BHK-21, MARC-145, PK-15, COS-7, VERO, CV-1, LLC-MK2, MDCK, MDBK, Raji B, CHO-K1, 3D4/31, IPEC-J2, THP-1, RAW 264.7, MA-104, 293T and ST cells.

27. The method according to claim 18, wherein the virus is selected from the group consisting of porcine reproductive and respiratory syndrome virus, porcine respiratory coronavirus, porcine epidemic diarrhea virus, porcine endogenous retroviruses, porcine hemagglutinating encephalomyelitis virus, transmissible gastroenteritis virus, Japanese encephalitis virus, human immunodeficiency virus, Dengue virus, West Nile virus, Ebola virus, Marburg virus, severe acute respiratory syndrome coronavirus, feline coronavirus, human cytomegalovirus, porcine cytomegalovirus, hepatitis C virus, simian immunodeficiency virus, feline immunodeficiency virus, Sindbis virus, herpes simplex virus, type A influenza virus, type B influenza virus, type C influenza virus, swine influenza virus, Nipah virus, Hendra virus, African swine fever virus, classical swine fever virus, bovine viral diarrhoea virus, pseudorabies virus, swine poxvirus, vesicular stomatitis virus, rabies virus, Eastern equine encephalitis virus equine arteritis virus, hepatitis E virus and porcine circovirus type 2.

28. A plasmid or viral vector containing the nucleic acid molecule according to claim 3.

29. A plasmid or viral vector containing the nucleic acid molecule according to claim 6.

30. A process for the production of a protein product, said process comprising: growing, under suitable nutrient conditions, prokaryotic or eucaryotic cells transfected with the nucleic acid molecule according to claim 3 in a manner allowing expression of said protein product, and isolating the desired protein product of the expression of said nucleic acid molecule.

31. A process for the production of a protein product, said process comprising: growing, under suitable nutrient conditions, prokaryotic or eucaryotic cells transfected with the nucleic acid molecule according to claim 6 in a manner allowing expression of said protein product, and isolating the desired protein product of the expression of said nucleic acid molecule.

* * * * *